(12) United States Patent
Tyavanagimatt et al.

(10) Patent No.: US 11,890,270 B2
(45) Date of Patent: *Feb. 6, 2024

(54) POLYMORPHIC FORMS OF ST-246 AND METHODS OF PREPARATION

(71) Applicant: Siga Technologies, Inc., Corvallis, OR (US)

(72) Inventors: Shanthakumar R. Tyavanagimatt, Sammamish, WA (US); Melialani A. C. L. S. Anderson, Corvallis, OR (US); William C. Weimers, Corvallis, OR (US); Dylan Nelson, Corvallis, OR (US); Tove' C. Bolken, Keizer, OR (US); Dennis E. Hruby, Albany, OR (US); Michael H. O'Neill, Painesville, OH (US); Gary Sweetapple, Madison, OH (US); Kelley A. McCloughan, South Haven, MI (US)

(73) Assignee: Siga Technologies, Inc., Corvallis, OR (US)

(*) Notice: Subject to any disclaimer, the term of this patent is extended or adjusted under 35 U.S.C. 154(b) by 504 days.

This patent is subject to a terminal disclaimer.

(21) Appl. No.: 17/136,674

(22) Filed: Dec. 29, 2020

(65) Prior Publication Data

US 2021/0137885 A1    May 13, 2021

Related U.S. Application Data

(62) Division of application No. 16/520,897, filed on Jul. 24, 2019, now Pat. No. 10,933,050, which is a
(Continued)

(51) Int. Cl.
*A61K 31/404* (2006.01)
*A61K 39/275* (2006.01)
(Continued)

(52) U.S. Cl.
CPC .......... *A61K 31/404* (2013.01); *A61K 9/1652* (2013.01); *A61K 9/4866* (2013.01);
(Continued)

(58) Field of Classification Search
CPC ........................... A61K 31/404; C07D 209/70
(Continued)

(56) References Cited

U.S. PATENT DOCUMENTS

| 4,029,666 A | 6/1977 | Weber et al. |
| 4,061,763 A | 12/1977 | Shepard et al. |

(Continued)

FOREIGN PATENT DOCUMENTS

| CN | 101445478 A | 6/2009 |
| EP | 1364643 A1 | 11/2003 |

(Continued)

OTHER PUBLICATIONS

International Search Report and Written Opinion of the International Searching Authority, issued in corresponding PCT Application No. PCT/US2011/29576, dated Jun. 10, 2011.
(Continued)

*Primary Examiner* — Craig D Ricci
*Assistant Examiner* — Janet L Coppins
(74) *Attorney, Agent, or Firm* — Charles C. Achkar; Ostrolenk Faber LLP.

(57) ABSTRACT

Polymorph forms of 4-trifluoromethyl-N-(3,3a,4,4a,5,5a,6,6a-octahydro-1,3-dioxo-4,6-ethenocycloprop[f]isoindol-2(1H)-yl)-benzamide are disclosed as well as their methods of synthesis and pharmaceutical compositions.

8 Claims, 24 Drawing Sheets

Related U.S. Application Data division of application No. 16/025,057, filed on Jul. 2, 2018, now Pat. No. 10,406,137, which is a division of application No. 15/661,194, filed on Jul. 27, 2017, now Pat. No. 10,045,964, which is a division of application No. 14/959,180, filed on Dec. 4, 2015, now Pat. No. 9,744,154, which is a division of application No. 13/069,813, filed on Mar. 23, 2011, now Pat. No. 9,339,466.

(60) Provisional application No. 61/316,747, filed on Mar. 23, 2010, provisional application No. 61/373,031, filed on Aug. 12, 2010.

(51) Int. Cl.
| | | |
|---|---|---|
| *C07D 209/76* | (2006.01) | |
| *A61K 9/16* | (2006.01) | |
| *A61K 9/48* | (2006.01) | |
| *C07D 209/70* | (2006.01) | |

(52) U.S. Cl.
CPC .......... *A61K 39/275* (2013.01); *C07D 209/70* (2013.01); *C07D 209/76* (2013.01)

(58) Field of Classification Search
USPC ...................................................... 514/411
See application file for complete search history.

(56) References Cited

U.S. PATENT DOCUMENTS

| | | | |
|---|---|---|---|
| 4,173,646 | A | 11/1979 | Shepard et al. |
| 5,068,356 | A | 11/1991 | Wicher |
| 6,433,016 | B1 | 8/2002 | Georgiev |
| 6,596,771 | B2 | 7/2003 | Georgiev |
| 7,687,641 | B2 | 3/2010 | Jordan et al. |
| 7,737,168 | B2 | 6/2010 | Jordan et al. |
| 7,872,037 | B2 | 1/2011 | Jordan et al. |
| 7,956,197 | B2 | 6/2011 | Jordan et al. |
| 8,039,504 | B2 | 10/2011 | Jordan et al. |
| 8,124,643 | B2 | 2/2012 | Jordan et al. |
| 9,339,466 | B2 * | 5/2016 | Tyavanagimatt .... C07D 209/70 |
| 2007/0003516 | A1 | 1/2007 | Almond et al. |
| 2008/0004452 | A1 | 1/2008 | Jordan et al. |
| 2012/0020922 | A1 | 1/2012 | Jordan et al. |
| 2012/0041044 | A1 | 2/2012 | Trepat Guixer et al. |

FOREIGN PATENT DOCUMENTS

| | | |
|---|---|---|
| EP | 1698349 A1 | 6/2006 |
| JP | 1964-012931 B | 4/1964 |
| JP | H09-506899 | 7/1997 |
| WO | WO-1995/17168 A1 | 6/1995 |
| WO | WO-2002/43704 A1 | 6/2002 |
| WO | WO-2002/067939 A1 | 9/2002 |
| WO | WO-2004-112718 A2 | 12/2004 |
| WO | WO-2005/065715 A1 | 7/2005 |
| WO | WO-2008-079159 A2 | 7/2008 |
| WO | WO-2008-130348 A1 | 10/2008 |

OTHER PUBLICATIONS

European Search Report Application No. 07755857.5, dated Nov. 15, 2010.

U.S. Office Action from U.S. Appl. No. 11/785,998, dated Nov. 5, 2010.

Henderson et al., Smallpox as a Biological Weapon, JAMA 281:2127-2137 American Medical Association, (1999).

Downie et al., "The Antibody Response in Man Following Infection With Viruses of the PDX Group," J. Hyg. 58:479-487 (1958).

Moss, "Poxyirdae and Their Replication," Virology. Chapter 74:2079-2111, (1990) Raven Press, Ltd, NY.

Modlin, "Vaccinia (Smallpox) Vaccine, Recommendations of the Advisory Committee on Immunization Practices (ACP)", 2001, MMWR (Morb Mart Wkly Rep) 50:1-25 (2001).

Engler at al. "Smallpox vaccination: Risk considerations for patients with atopic dermatitis,". J. Allergy Clin Immunol. 110(3):367-366 (2002).

Jackson et al., "Expression of Mouse Interleukin-4 by a Recombinant Extromelia Virus Suppresses Cytolytic Lymphocyte Responses and Overcomes Genetic Resistance to Mousepox," Journal of Virology, 75(3):125-1210, American Society for Microbiology (2001).

Bronson et al., "(S)-1-(3-Hydroxy-20(phosphonylmethoxy)propyl)cytosine (HPMPC): a Potent Antiherpesvirus Agent," Adv. Exp.-Med. Bid. 278:277-283 (1990).

De Clercq et al., "Antiviral activity of phosphonylmethoxyalklyl derivatives of purine and pyrimidines," Antiviral Research, 8:261-272, Elsevier Science Publishers B.V. (1987).

De Oliveria et al., "Evaluation of Cidofovir (HPMPC, GS-504) against adenovirus type 5 infection in vitro and in a New Zealand rabbit ocular model, "Antiviral Research 31:186-172, Elsevier Science B.V. (1996).

Snoeck et al. "Phase II Double-011nd, Placebo-Controlled Study of the Safety and Efficacy of Cidofovir Topical Gel for the Treatment of Patients with Human Papillomavirus infection," CID 33:597-602 (2001).

Smee et al., "Characterization of Wild-Type and Cidofovir-Resistant Strains of Camelpox., cowpox, Monkeypox, and Vaccinia Viruses," Antimicrobial Agents Chemotherapy 46(5):1329-1335 (2002).

Lalezari et al., "Intravenous Cidofovir for Peripheral Cytomegalovirus Retinitis In Patients with AIDS," Ann. Intern. Med. 126(4)157-283 (1097).

De Clercq et al., "Vaccinia Virus Inhibitors as a Paradigm for the Chemotherapy of Poxvirus infections," Clinical Microbiology Review, 12(2):382-397 (2001).

Bauer et al., "Prophylaxis of Smallpdx With Methisazone" American Journal of Epidemiology. 90(2):130-145 (1969).

De Clercq et al., "Carboxylic Adenosine Analogues as S-Adenosylhomocysteine Hydrolase Inhibitors and Antiviral Agents: Recent Advances," Nucleosides Nucleotides 17(1-3):625-634 (1998).

Coulombe et al.; Pharmacokinetics of the antiviral agent 3-dexaneplanocin A, European Journal of Drug Metabolism Pharmacokinetics 20(3):197-202 (1995).

Obara et al., "New Naplanocin Analogues. 7. Synthesis and Antiviral Activity of 2-Halo Derivatives of neplanocin A," J. Med. Chem. 39:3847-3852 (1996).

CAS RN 492455-97-7 STN Entry Date Feb. 20, 2003.
CAS RN 492426-98-9 STN Entry Date Feb. 20, 2003.
CAS RN 488821-91-6 STN Entry Date Feb. 12, 2003.
CAS RN 432022-17-8 STN Entry Date Jun. 19, 2002.
CAS RN 432022-16-7 STN Entry Date Jun. 19, 2002.
CAS RN 340982-60-7 STN Entry Date Jun. 14, 2001.
CAS RN 331632-70-3 STN Entry Date Apr. 17, 2001.
CAS RN 329912-01-8 STN Entry Date Apr. 4, 2001.
CAS RN 329775-41-9 STN Entry Date Apr. 3, 2001.
CAS RN 329717-02-4 STN Entry Date Apr. 2, 2001.
CAS RN 329368-29-8 STN Entry Date Apr. 1, 2001.
CAS RN 329362-05-2 STN Entry Date Apr. 1, 2001.
CAS RN 316383-22-9 STN Entry Date Jan. 24, 2001.

Kohler, E.P. et al."The preparation of cyclic ketones by ring enlargement", Journal of the American Chemical Society, vol. 16, pp. 1057-10611939.

Ishitobi et al. "Re-examination of the Cycloaddition of Cycloheptatriene with Maleic Anhydride", Bulletin of the Chemical Society of Japan, 1971, vol. 44, pp. 2993-3000.

Kurtz, D.W. et al., "A valence isomer trapping procedure for introductory organic laboratory", Journal of Chemical Education, 1989, vol. 66, pp. 873-874.

Schueler, P.E. et al., "Synthesis and relative stereochemical assignment of the four isomeric cyclopropane-bridged tricycle [3.2.2.0214-nonan-6-0ls", Journal of Organic Chemistry, 1974, vol. 39, pp. 2063-2069.

(56) References Cited

OTHER PUBLICATIONS

Blumel, J. et al., "Metallated bicyclo[3.2.2]nona-2,6,8-trienes, their rearrangement to barbaralenes, and a short syntheseis of the bicyclo[3.2.2]nona-2,6,8-trien-4-y1 anion", Chemische Berichte, 1993, vol. 12, pp. 1283-1290.
Supplementary European Search Report EP Application No. 04776765, dated Jul. 30, 2008.
Shiva Mohan Verma: "restricted rotations in configurational assignments: the diels-alder adduct of 1,3,5-cycloheptatriene and maleic anhydride." Recueil Des Travaux Chimiques Despays-Bas., vol. 97, No. 9, 1978 (Sep. 1978),pp. 238-241, XP002490138 Nlelsevier Science Publishers. Amsterdam. p. 238-239.
Chemical Abstracts, vol. 62, No. 37, 1965 Columbus, Ohio, US; abstract No. 529g, col. 1, XP002490139.
Office Action dated Sep. 14, 2009, U.S. Appl. No. 10/561,153, filed Apr. 6, 2006, Inventor Jordan et al.
Office Action dated May 6, 2009, U.S. Appl. No. 11/785,997, filed Apr. 23, 2007, Inventor Jordan et al.
Indian Journal of Chemistry, S.M. Verma & C. Koteswara Rao, 1975, 13(12), 1278-1281.
Journal of the Royal Netherlands Chemical Society, 1978, 97(9), 238-248.
Japanese Laid-Open Patent Publication No. S39-12931.
Japanese Laid-Open Patent Publication No. S52-47844.
Indian Journal of Chemistry, Hawaldar Maurya & S.M. Verma, Section B, 1986, 25B(5), 542-544.
Chem. Pharm. Bull., Masao Ishikawa, et al., Intermolecular Hydrazides and Hydroxamates II. Synthesis of 2-Amino-cis-Perhydroisoindolin-1,3-dione Homologues, 1968, 16(4), 618-621.
Japanese Laid-Open Patent Publication No. H05-140100.
Indian Journal of Chemistry Section B, 1977, 15B(8), 700-702.
Japanese Laid-Open Patent Publication No. S64-83065.
Fenner et al., The Epidemiology of Smallpox. In: Smallpox and its Eradication. Switzerland: World Health Organization 1988.
Jezek et al., Human Monkey pox. In: Melnick JL ed. Monographs in Virology. vol. 17. Basel, Switzerland: S. Karger AG. 1988:81-102.
Quenelle et al. 2007. Efficacy of Delayed Treatment with ST-246 Given Orally Against Systemic Orthopoxvirus Infections in Mice. Antimicrobial Agents and Chemotherapy Feb. 51(2): 689-95.
Smee et al. 2008. Progress in the Discovery of Compounds Inhibiting Orthopoxviruses in Animals Models, Antiviral Chemistry and Chemotherapy. 19 (3): 115-24.
Vora et al., 2008, Severe Eczema Vaccinatum in a Household Contact of a Smallpox Vaccine. Clinical Infections Disease 15; 46(10): 1555-61.
European Search Report 07867085.8, dated May 14, 2012.
Chinese Office Action for Chinese Application No. 2013-501426 dated Dec. 22, 2014 (English Translation Only).
Israeli Office Action from Israeli Application No. 221991 dated Mar. 30, 2015.
Dekker, Marcel et al. "Polymorphism in Pharmaceutical Solid" (Chapter 1) p. 1-10 and (Chapter 5) p. 183-226 (1999).
Bryn, Stephen, et al. "Pharmaceutical Solids: A Strategic Approach to Regulatory Considerations" Pharmaceutical Research, vol. 12, No. 7. p. 945-954 (1995).
Japanese Office Action for Japanese Application No. 2013-501426 dated Aug. 10, 2015 (with English Translation).
Yamano, Mitsuhisa "Novel Drug Process Research and Crystal Polymorphism Phenomenon," Pharmacia, 2009, vol. 45, No. 4, p. 327-332.
Takada, Noriyuki "Drug Substance Form Screening and Selection in Drug Discovery Stage," Pharm Stage, 2007, vol. 6, No. 10, p. 20-25 (with English Language Abstract).
Ashizawa, Kazuhide et al., "Importance of Property Evaluation in Drug Discovery Stage," Pharm Stage, 2009 vol. 9, No. 6, p. 72-79 (with English Language Abstract).
Kokima, Takashi, et al., "Efficient Selection of Crystalline Form in Pharmaceutical Development—Application of Raman Spectroscopic Method in Salt/Crystal Polymorph Screening," Pharm Tech Japan, 2007, vol. 23, No. 12, p. 173 (2461)-181(2469) (with English Language Abstract).
Stahly, Patrick, "The Importance of Salt Selection and Polymorph Screening for the Drug Product," Journal of Pharmaceutical Science and Technology, 2006, vol. 66, No. 6, p. 435-439 (with English Language Abstract).
"Pharmaceutical Residual Solvent Guidelines," Notification No. 307 of the Pharmaceutical Affairs Bureau, 1998. (with English Language Abstract).
Korean Office Action issued in Korean Application No. 10-2016-7004585, dated Jun. 9, 2016. (With English Language Translation).
Chinese Office Action and translation thereof issued in Counterpart Application No. 201510445962.2, dated Aug. 6, 2018.
Caira M R, "Crystalline Polymorphism of Organic Compounds", Topics in Current Chemistry, Springer, Berlin, DE, (Jan. 1, 1998), vol. 198, doi:10.1007/3-540-69178-2_5, ISSN 0340-1022, pp. 163-208, XP001156954.
Argentine Office Action and translation thereof issued in Counterpart Application No. 20110102672, dated Sep. 3, 2019.

\* cited by examiner

POLYMORPHIC FORMS OF ST-246 AND METHODS OF PREPARATION

CROSS REFERENCE TO RELATED APPLICATIONS

The present application is a divisional application of U.S. patent application Ser. No. 16/520,897, filed Jul. 24, 2019 which is a divisional of U.S. patent application Ser. No. 16/025,057 filed Jul. 2, 2018, now U.S. Pat. No. 10,406,137, which is a divisional application of U.S. patent application Ser. No. 15/661,194 filed Jul. 27, 2017, now U.S. Pat. No. 10,045,964, which is a divisional application of U.S. patent application Ser. No. 14/959,180, filed on Dec. 4, 2015, now U.S. Pat. No. 9,744,154, which is a divisional application of U.S. patent application Ser. No. 13/069,813, filed on Mar. 23, 2011, now U.S. Pat. No. 9,339,466 which claims benefit of U.S. Provisional Application No. 61/316,747, filed on Mar. 23, 2010 and U.S. Provisional Application No. 61/373,031, filed on Aug. 12, 2010, the subject matter of each of which is incorporated by reference in their entirety.

STATEMENT REGARDING FEDERALLY SPONSORED RESEARCH OR DEVELOPMENT

This invention was made with U.S. government support under Contract No. HHSN266200600014C awarded by the National Institutes of Health (NIH). The US government has certain rights in this invention.

FIELD OF THE INVENTION

The present invention relates to particular crystalline forms of a pharmaceutical compound, 4-trifluoromethyl-N-(3,3a,4,4a,5,5a,6,6a-octahydro-1,3-dioxo-4,6-ethenocycloprop[f]isoindol-2(1H)-yl)-benzamide, named ST-246, to processes for their preparation, pharmaceutical composition comprising different crystalline forms and its use in therapy.

BACKGROUND OF THE INVENTION

Throughout this application, various publications are referenced within the text. The disclosure of these publications in their entireties are hereby incorporated by reference into this application in order to more fully describe the state of the art as known to those skilled in therein as of the date of the invention described and claimed herein.

Following the eradication of smallpox (Fenner et al., The epidemiology of smallpox. In: Smallpox and its eradication. Switzerland: World Health Organization; 1988) and the subsequent cessation of routine childhood vaccinations for smallpox, the number of people susceptible to infection with variola virus (VARV), the etiologic agent that causes smallpox, has dramatically increased worldwide. In addition, encroachment into wildlife habitats, the trade of exotic pets, and the trade of bush meat increase the risk for zoonotic infection with other orthopoxviruses, such as monkeypox virus (MPXV), for which vaccination against smallpox provides some cross protection (Jezek et al., Human monkey pox. In: Melnick J L ed. Monographs in virology. Vol. 17. Basel, Switzerland: S Karger AG. 1988:81-102).

Given that a large proportion of the worldwide population is susceptible to smallpox, the emergence of MPXV in the United States in 2003, and the continued concern over the intentional release of VARV, there is renewed interest in the development of safer smallpox and other orthopoxvirus vaccines and antiviral therapeutics.

One recently discovered antiviral compound is ST-246, a specific and potent inhibitor of an orthopoxvirus protein critical for virus maturation. Several studies evaluating ST-246 for activity against orthopoxviruses have demonstrated excellent in vitro and in vivo efficacy (Quenelle et al. 2007. Efficacy of delayed treatment with ST-246 given orally against systemic orthopoxvirus infections in mice. Antimicrobial Agents and Chemotherapy Feb; 51(2):689-95, Smee et al, 2008. Progress in the discovery of compounds inhibiting orthopoxviruses in animal models. Antiviral Chemistry and Chemotherapy 19(3):115-24). When evaluated in vitro against vaccinia virus (VV), cowpox virus (CV), ectromelia virus (ECTV), monkeypox, camelpox, and variola viruses, ST-246 inhibited virus replication by 50% (50% effective concentration [$EC_{50}$]) at a concentration of ≤0.07 μM. With animal models using lethal infections with ECTV, VV, or CV, ST-246 was reported to be nontoxic and highly effective in preventing or reducing mortality even when treatments were delayed up to 72 h post-viral inoculation (Quenelle et al., 2007. Efficacy of delayed treatment with ST-246 given orally against systemic orthopoxvirus infections in mice. Antimicrobial Agents and Chemotherapy Feb; 51(2):689-95, Smee et al. 2008. Progress in the discovery of compounds inhibiting orthopoxviruses in animal models. Antiviral Chemistry and Chemotherapy 19(3):115-24). ST-246 was also evaluated with the nonlethal mouse tail lesion model using intravenous VV. When ST-246 was administered orally twice a day at 15 or 50 mg/kg of body weight for 5 days, the tail lesions were significantly reduced (Smee et al., 2008. Progress in the discovery of compounds inhibiting orthopoxviruses in animal models. Antiviral Chemistry and Chemotherapy 19(3):115-24). Most recently, an infant was given ST-246 as an FDA-authorized emergency treatment for eczema vaccinatum which developed after exposure to the parent's predeployment military smallpox immunization (Vora et al., 2008, Severe eczema vaccinatum in a household contact of a smallpox vaccine. Clinical Infectious Disease 15; 46(10):1555-61).

ST-246 was disclosed in WO 2008/130348, WO 2004/112718 and WO 2008/079159 as one of the tetracyclic acylhydrazide compounds for treatment or prophylaxis of viral infections and diseases associated herewith, particularly those viral infections and associated diseases caused by the orthopoxvirus. These publications disclose a process for the preparation of ST-246 but do not disclose what polymorphic form is made. Nonetheless, the disclosed process yields ST-246 hemihydrate, the polymorphic Form V as discussed herein below.

The process of making a monohydrate of ST-246 was disclosed in CN 101445478A. The data shown in this publication corresponds to polymorphic Form III according to the present classification of polymorphs of ST-246.

It has now been unexpectedly discovered that ST-246 can exist in many different polymorphic forms. A particular crystalline form of a compound may have physical properties that differ from those of other polymorphic forms and such properties may influence markedly the physico-chemical and pharmaceutical processing of the compound, particularly when the compound is prepared or used on a commercial scale. Such differences may alter the mechanical handling properties of the compound (such as the flow characteristics of the solid material) and the compression characteristics of the compound. Further, the discovery of new polymorphic forms of such pharmaceutically important compound as ST-246, provides a new opportunity to improve the performance characteristics of a pharmaceutical end product and enlarges the repertoire of materials that a formulation scientist has available for designing, for example, a pharmaceutical dosage form of a drug with targeted release profile or other desired physico-chemical properties.

Further, given that new polymorphic forms of a drug substance may display different melting point, hygroscopicity, stability, solubility and/or dissolution rate, crystallinity, crystal properties, bioavailability, toxicity and formulation handling characteristics, which are among the numerous properties that need to be considered in preparing medicament that can be effectively administered. Furthermore, regulatory agencies require a definitive knowledge, characterization and control of the polymorphic form of the active component in solid pharmaceutical dosage forms. Thus, there is a need in the art for crystallization and characterization of new polymorphic forms of ST-246.

SUMMARY OF THE INVENTION

The present invention provides a polymorph Form I of ST-246 which shows an X-ray powder diffraction pattern having characteristic peaks of about 7.63, 10.04, 11.47, 14.73, 15.21, 15.47, 16.06, 16.67, 16.98, 18.93, 19.96, 20.52, 20.79, 22.80, 25.16, 26.53, 27.20, 27.60, 29.60, 30.23, 30.49, 30.68, 31.14, 33.65, 34.33, 35.29, 35.56, 36.30, 37.36, 38.42, 38.66 degrees.

The present invention also provides a polymorph Form II of ST-246 which shows a X-ray powder diffraction pattern having characteristic according to FIG. 2.

The present invention further provides a polymorph Form III of ST-246 which shows an X-ray powder diffraction pattern having characteristic peaks of about 6.71, 9.05, 12.49, 13.03, 13.79, 14.87, 15.72, 16.26, 16.74, 18.10, 18.43, 19.94, 21.04, 21.51, 23.15, 23.51, 25.32, 26.24, 26.87, 27.32, 27.72, 28.55, 29.08, 29.50, 29.84, 31.27, 33.48, 35.36, 39.56 degrees.

The present invention also provides a polymorph Form IV of ST-246 which shows an X-ray powder diffraction pattern having characteristic as shown in FIG. 4.

The present invention further provides a polymorph Form VI ST-246 which shows an X-ray powder diffraction pattern having characteristic peaks as shown in FIG. 6.

The present invention also provides pharmaceutical compositions comprising each of the ST-246 polymorphs Forms I-VI and further comprising one or more pharmaceutically acceptable carriers, excipients, diluents, additives, fillers, lubricants or binders.

The present invention further provides methods of treating orthopoxvirus infections or eczema vaccinatum comprising administering to a subject animal or human in need thereof a therapeutically effective amount of each of the ST-246 polymorphs Forms I-VI.

The present invention also provides methods for the synthesis of each of the ST-246 polymorphs Forms I-VI.

The present invention also provides a dosage unit form for oral administration, wherein ST-246 has a D90% particle size diameter of up to about 300 microns. In some embodiments, ST-246, polymorph I, II, III, IV and VI has a D90% particle size diameter of about 5 microns, in other embodiments, the D90% particle size diameter is about 16.6 microns, in yet another embodiment, a D90% particle diameter is about 26.6 microns and in yet another embodiment, the D90% particle diameter is about 75 microns.

In another aspect of the invention, a unit dosage form for oral administration comprising 200 mg of ST-246, wherein ST-246 is selected from a group consisting of ST-246 polymorph Form II, ST-246 polymorph Form III, ST-246 polymorph Form IV and ST-246 polymorph Form VI and further comprising 33.15 mg of lactose monohydrate; 42.90 mg of croscarmellose sodium; 1.95 mg of colloidal silicon dioxide; 13.65 mg of hypromellose, 7.8 mg of sodium lauryl sulfate; 1.95 mg of magnesium stearate; and a quantity of microcrystalline cellulose up to 88.60 mg such that the total weight of the dosage form, including any impurities, water and residual solvents, is 390 mg.

DETAILED DESCRIPTION OF THE INVENTION

Definitions

Figure 1:
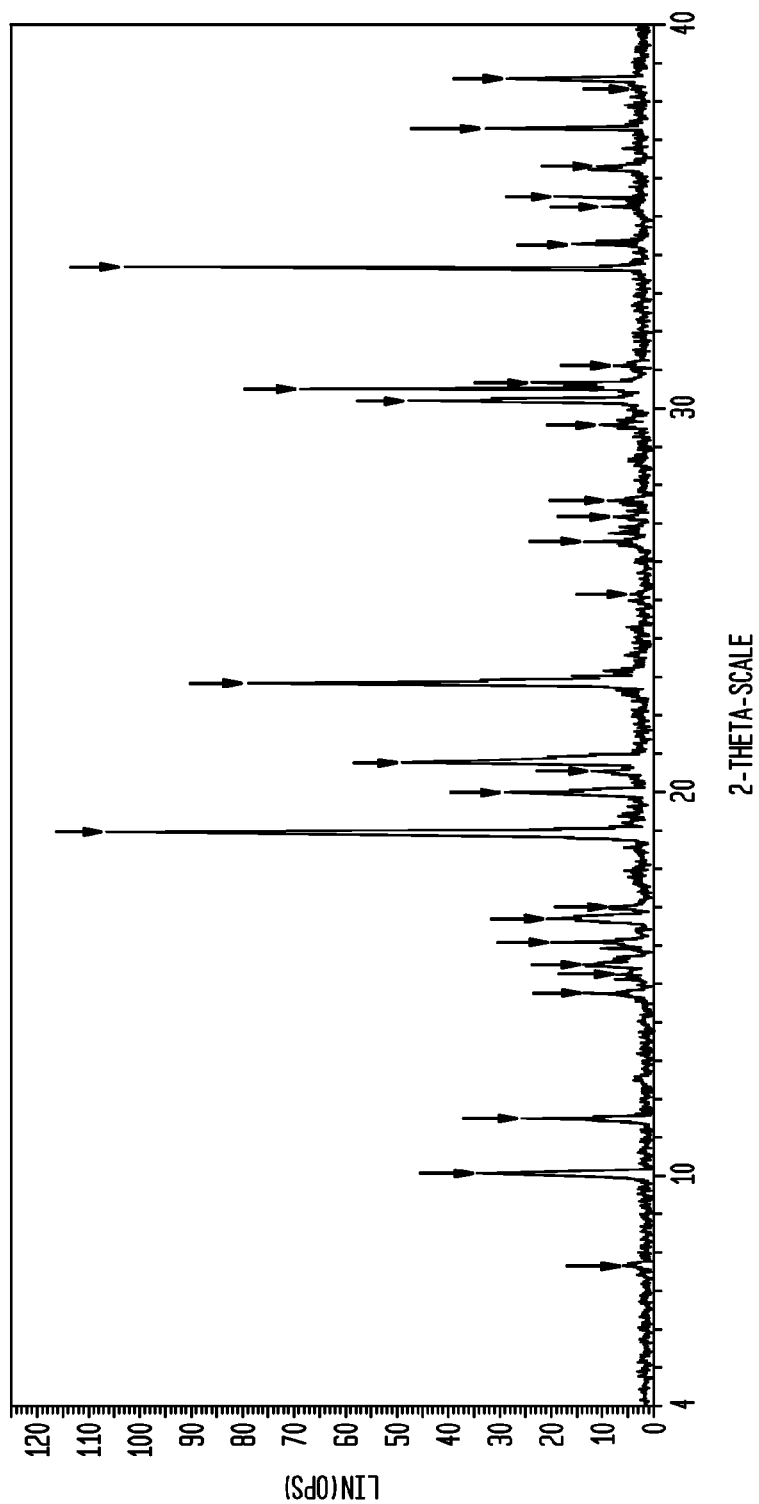
FIG. 1 shows an X-ray powder diffraction (XRPD) pattern of Form I.

In accordance with this detailed description, the following abbreviations and definitions apply. It must be noted that as used herein, the singular forms "a," "an," and "the" include plural referents unless the context clearly dictates otherwise.

The term "polymorphic form, polymorph, polymorph form, crystalline form, physical form or crystalline polymorph" of ST-246 in the present invention refers to a crystal modification of ST-246, which can be characterized by analytical methods such as X-ray powder diffraction pattern, (XRPD), differential scanning calorimetry (DSC), by its melting point analysis or Infrared Spectroscopy (FTIR).

The term "hydrate" as used herein means a compound of the invention or a salt thereof that further includes a stoichiometric or non-stoichiometric amount of water bound by non-covalent intermolecular forces. Hydrates are formed by the combination of one or more molecules of water with one molecule of the substances in which the water retains its molecular state as $H_2O$, such combination being able to form one or more hydrate. The term "hemihydrate" as used herein refers to a solid with 0.5 molecule of $H_2O$ per molecule of the substance.

The term "pharmaceutical composition" or "pharmaceutical formulation" is intended to encompass a drug product including the active ingredient(s), pharmaceutically acceptable excipients that make up the carrier, as well as any product which results, directly or indirectly, from combination, complexation or aggregation of any two or more of the ingredients. Accordingly, the pharmaceutical compositions of the present invention encompass any composition made by admixing the active ingredient, active ingredient dispersion or composite, additional active ingredient(s), and pharmaceutically acceptable excipients.

The particle size distribution (PSD) of a powder, or granular material, or particles dispersed in fluid, is a list of values or a mathematical function that defines the relative amounts of particles present, sorted according to size. PSD is also known as grain size distribution. Since particle size for a complex media is a distribution of diameters, statistics can be used to convey the results. A common method is to use d10, d50 and d90 values based on volume distribution. That is to say that 10%, 50% and 90%, respectively, of the particle size distribution is smaller than the stated diameter.

The term "dosage unit" refers to a single unit of the dosage form that is to be administered to the patient. The dosage unit will be typically formulated to include an amount of drug sufficient to achieve a therapeutic effect with a single administration of the dosage unit although where the size of the dosage form is at issue, more than one dosage unit may be necessary to achieve the desired therapeutic effect. For example, a single dosage unit of a drug is typically, one tablet, one capsule, or one tablespoon of liquid. More than one dosage unit may be necessary to administer sufficient drug to achieve a therapeutic effect where the amount of drug causes physical constraints on the size of the dosage form.

The term "half-life" is a pharmacokinetic term used to indicate the length of time necessary to eliminate 50% of the remaining amount of drug present in the body.

The term "AUC" (i.e., "area under the curve," "area under the concentration curve," or "area under the concentration-time curve") is a pharmacokinetic term used to refer a method of measurement of bioavailability or extent of absorption of a drug based on a plot of an individual or pool of individual's blood plasma concentrations sampled at frequent intervals; the AUC is directly proportional to the total amount of unaltered drug in the patient's blood plasma. For example, a linear curve for a plot of the AUC versus dose (i.e., straight ascending line) indicates that the drug is being released slowly into the blood stream and is providing a steady amount of drug to the patient; if the AUC versus dose is a linear relationship this generally represents optimal delivery of the drug into the patient's blood stream. By contrast, a non-linear AUC versus dose curve indicates rapid release of drug such that some of the drug is not absorbed, or the drug is metabolized before entering the blood stream.

The term "$C_{max}$" (i.e., "maximum concentration") is a pharmacokinetic term used to indicate the peak concentration of a particular drug in the blood plasma of a patient.

The term "$T_{max}$" (i.e., "time of maximum concentration" or "time of $C_{max}$") is a pharmacokinetic term used to indicate the time at which the $C_{max}$ is observed during the time course of a drug administration. As would be expected, a dosage form that would include an immediate release as well as a gastric retentive component would have a $T_{max}$ that is higher than the $C_{max}$ for an immediate release dosage form, but lower than the $T_{max}$ for a purely gastric retentive dosage form.

It has now been surprisingly discovered that ST-246 exists in different crystalline forms denominated Form I, Form II, Form III, Form IV, Form V, and Form VI.

All forms have been fully characterized and comparability data have been generated. All the forms are as characterized hereinafter inter alia by the following methodology:

Physical Experimental Methodology
X-Ray Powder Diffraction (XRPD)

Diffraction patterns were collected using a Bruker D8 Discovery diffractometer configured with an XYZ stage, laser video microscope for positioning, and HiStar area detector. Collection times were nominally 60 seconds. A Cu Ka radiation 1.5406 tube was operated at 40 kV and 40 mA was used to irradiate samples. The X-ray optics consists of a Gobel mirror coupled with a pinhole collimator of 0.5 mm. Theta-theta continuous scans were employed with a sample-detector distance of 15 cm, which gives an effective 2θ range of 4-40°. Samples were mounted in low background quartz plates. A variable temperature hot stage was used to manipulate sample temperature for some experiments.

The polymorphs of ST-246 are characterized by their X-ray powder diffraction patterns (XRPD) and/or their Raman spectroscopy peaks. With respect to X-ray powder diffraction, the relative intensities of the X-ray powder diffraction peaks of a given polymorph may vary depending upon the crystal size of the polymorph used to determine the pattern. This is a phenomenon of preferred orientation. Preferred orientation is caused by the morphology of crystals. In this case, the XRPD analysis may be carried out with the sample spinning in the sample holder during XRPD analysis to reduce the preferred orientation effects. For the XRPD analysis, the pattern is given in terms of the "degree of 2θ (two theta)" angles of the peaks.

With respect to the percent value of relative intensity (I/Io), Io represents the value of the maximum peak determined by XRPD for the sample for all "degree 2θ." angles and I represents the value for the intensity of a peak measured at a given "degree 2θ" angle".

The angle "2θ degree" is a diffraction angle which is the angle between the incident X-rays and the diffracted X-rays. The values for the relative intensities for a given peak set forth in percent and the "degree.2θ" angles are calculated. However, there are key major peaks at given angles in these X-ray powder diffraction patterns which are unique to each given polymorph form. These peaks are present in the XRPD patterns of each of the polymorph forms having a crystal size of about 10 to 40 microns. Any of these major peaks, either alone or in any distinguishing combination, are sufficient to distinguish one of the polymorph forms from the other present polymorphic forms.

Infrared Spectroscopy (FTIR)

Infrared spectra were obtained with a Nicolet 510 M-O Fourier transform infrared spectrometer, equipped with a Harrick Splitpeam™ attenuated total reflectance device. Spectra were acquired from 4000-400 $cm^{-1}$ with a resolution of 4 $cm^{-1}$ and 128 scans were collected for each analysis.

Preparation of the Crystalline Forms

The present invention provides a method of producing polymorphic Form I of ST-246, comprising the steps of:
   a) dissolving ST-246 in at least one organic solvent and an amount of water to make a solution;
   b) cooling said solution to a temperature that causes the preferential crystallization of said ST-246 polymorphic Form I; and
   c) optionally drying the formed crystals of ST-246,
   wherein said organic solvent is selected from a group consisting of isopropyl alcohol (IPA), ethyl acetate, ethanol, methanol, acetone, isopropyl acetate and tetrahydrofuran (THF).

Preferably, the method further comprises adding seed crystals of polymorphic Form I ST-246 during step (b). Also preferably, the cooling step takes place over at least 15 minutes, more preferably over at least 2 hours and most preferably over at least 5 hours.

Also preferably, the organic solvent is ethyl acetate and the water content is about 40% by volume of total solvent volume, more preferably about 5% by volume of total solvent volume, more preferably about 3% by volume of total solvent volume and most preferably about 2% by volume of total solvent volume. Also preferably, the organic solvent is isopropyl alcohol and the water content is about 5% by volume of total solvent volume.

The present invention also provides a method of producing crystal polymorphic Form II of ST-246, comprising the steps of:
   a) dissolving ST-246 in at least one solvent to make a solution;
   b) cooling said solution to a temperature that causes the preferential crystallization of said ST-246 polymorphic Form II; and
   c) optionally drying the formed crystals of ST-246,
   wherein said solvent is selected from the group consisting of ethyl acetate, chloroform, 1-propanol, isopropyl alcohol (IPA) ethanol, acetone, acetonitrile, toluene, isopropyl acetate and dimethylformamide (DMF).

Preferably, the method further comprises adding seed crystals of polymorphic Form II ST-246 during step (b). Also preferably, the solvent does not contain water and is selected from the group consisting of ethyl acetate and chloroform.

The present invention further provides a method of producing crystal polymorphic Form II of ST-246, comprising the steps of:
   a) dissolving ST-246 in ethanol and water to make a solution;
   b) cooling said solution to a temperature that causes the preferential crystallization of said ST-246 polymorphic Form II; and
   c) optionally drying the formed crystals of ST-246.

Preferably, the method further comprises adding seed crystals of polymorphic Form II ST-246 during step (b). Also preferably, the volume ratio of ethanol:water is about 1:1.

The present invention also provides a method of producing crystal polymorphic Form III of ST-246, comprising the steps of:
   a) dissolving ST-246 in at least one organic solvent and water to make a solution;
   b) cooling said solution to a temperature that causes the preferential crystallization of said ST-246 polymorphic Form IIII: and
   c) optionally drying the formed crystals of ST-246,
   wherein the organic solvent is selected from the group consisting of isopropyl alcohol (IPA), ethyl acetate and ethanol.

Preferably, the method further comprises adding seed crystals of polymorphic Form III ST-246 during step (b). Also preferably, the cooling step takes place over less than 15 minutes.

The present invention further provides a method of producing crystal polymorphic Form III of ST-246, comprising the steps of:
   a) dissolving ST-246 in at least one organic solvent to make a solution;
   b) cooling said solution to a temperature that causes the preferential crystallization of said ST-246 polymorphic Form III; and
   c) optionally drying the formed crystals of ST-246,
   wherein the organic solvent is selected from the group consisting of acetone, isopropyl alcohol (IPA), dimethylamine (DMA), pyridine, trifluoroethanol (TFE), methanol, ethanol, chloroform, acetonitrile (ACN), and tetrahydrofuran (THF).

Preferably, the method further comprises adding seed crystals of polymorphic Form III ST-246 during step (b).

The present invention also provides a method of producing crystal polymorphic Form IV of ST-246, comprising the steps of:
   a) dissolving ST-246 in at least one organic solvent optionally containing water to make a solution;
   b) cooling said solution to a temperature that causes the preferential crystallization of said ST-246 polymorphic Form IV precipitation in crystal form of ST-246; and
   c) optionally drying the formed crystals of ST-246,
   wherein said solvent is selected from the group consisting of: a mixture of acetonitrile and ethyl acetate, a mixture of ethanol and toluene, a mixture of water and ethyl acetate, and a mixture of trifluoroethanol and THF.

Preferably, the method further comprises adding seed crystals of polymorphic Form IV ST-246 during step (b). Also preferably, the solvent is a mixture of ACN and ethyl acetate at a volume ratio of about 1:4, a mixture of ethanol and toluene at a volume ratio of about 1:4, a mixture of water and ethyl acetate at a volume ratio of about 1:4, and a mixture of TFE and THF at a volume ratio of about 1

The present invention further provides a method of producing crystal polymorphic Form IV of ST-246, comprising the steps of:
a) dissolving ST-246 in at least one solvent to make a solution;
b) cooling said solution to a temperature that causes the preferential crystallization of said ST-246 polymorphic Form IV; and
c) optionally drying the formed crystals of ST-246, wherein said solvent is selected from the group consisting of 1-butanol, trifluoroethanol (TFE), chloroform, dichloromethane and toluene.

Preferably, the method further comprises adding seed crystals of polymorphic Form IV ST-246 during step (b). Also preferably, the solvent does not contain water. Also preferably the solvent is 1-butanol.

The present invention also provides a method of producing crystal polymorphic Form VI of ST-246, comprising the steps of:
a) dissolving ST-246 in at least one solvent to make a solution;
b) cooling said solution to a temperature that causes the preferential crystallization of said ST-246 polymorphic Form VI; and c) optionally drying the formed crystals of ST-246, wherein said solvent is selected from the group consisting of nitromethane, methanol and chloroform.

Preferably, the method further comprises adding seed crystals of polymorphic Form VI ST-246 during step (b). Also preferably, the solvent does not contain water and is nitromethane.

The ST-246 is prepared as outlined in the Examples below. Processes for crystallization of polymorphs of the ST-246 may embrace multiple combinations of techniques and variations thereof. Crystallization of polymorphs of the ST-246 may be executed by dissolving, dispersing, or slurrying ST-246 at a suitable temperature in the solvent whereby portion of the said solvent evaporates increasing the concentration of the ST-246 in the said solution, dispersion, or slurry, cooling the said mixture, and optionally washing and/or filtering and drying the resulting crystals of the ST-246.

Crystal formation may as well involve more than one crystallization process. In certain cases, one, two or more extra crystallization steps may be advantageously performed for different reasons, such as, to increase the quality of the resulting crystal form. For instance, the polymorphs of the present invention could also be prepared by adding a solvent to an initial starting base material of the ST-246, stirring the solution at a fixed temperature until the substances would be fully dissolved, concentrating the solution by vacuum distillation, and cooling. A first crystallization would take place and the formed crystals would be washed with a solvent, and followed by solubilization of the ST-246 with the same or different solvent to form the desired polymorph. The reaction mixture may be heated to reflux and recrystallization of the reaction mixture would occur, followed by a cooling step from reflux. The formed polymorph would optionally be filtered and allowed to dry.

By dissolving, dispersing, or slurrying the ST-246 in the solvent, one may obtain different degrees of dispersion, such as suspensions, slurries or mixtures; or preferably obtain homogeneous one-phase solutions. The term “suspension” refers to a two-phase system consisting of a finely divided solid, i.e. ST-246 in amorphous, crystalline form, or mixtures thereof, dispersed (suspended) in a liquid or dispersing medium, usually the solvent. The term “slurry” refers to a suspension formed when a quantity of powder is mixed into a liquid in which the solid is only slightly soluble (or not soluble). “Slurrying” refers to the making of a slurry.

Optionally, the solvent medium may contain additives, for example dispersing agents, surfactants or other additives, or mixtures thereof of the type normally used in the preparation of crystalline suspensions. The additives may be advantageously used in modifying the shape of crystal by increasing the leniency and decreasing the surface area.

The solvent medium containing the solid may optionally be stirred for a certain period of time, or vigorously agitated using, for example, a high shear mixer or homogenizer or a combination of these, to generate the desired particle size for the organic compound. Control of precipitation temperature and seeding may be additionally used to improve the reproducibility of the crystallization process, the particle size distribution and the dosage form of the product. As such, the crystallization can be effected without seeding with crystals of the ST-246 or preferably in the presence of crystals of the ST-246, which are introduced into the solution by seeding. Seeding can also be effected several times at various temperatures. The amount of the seed material depends on the scale of the experiment and can readily be determined by a person skilled in the art. Typically, the amount of seeding material is about 0.1 to 1 weight % of the amount of crystalline material expected from the reaction.

The time for crystallization in each crystallization step will depend on the conditions applied, the techniques employed and/or solvents used. Breaking up the large particles or aggregates of particles after crystal conversion may additionally be performed in order to obtain a desired and homogeneous particle size. Accordingly, the crystals, powder aggregates and coarse powder of the polymorphic forms of the ST-246 may be optionally milled and sorted by size after undergoing conversion. Milling or grinding refers to physically breaking up the large particles or aggregates of particles using methods and apparatus well known in the art for particle size reduction of powders. Resulting particle sizes may range from millimeters to nanometers, yielding i.e. nanocrystals, microcrystals. A preferred apparatus for milling or grinding is a fluid energy mill, or micronizer, because of its ability to produce particles of small size within a narrow range of particle size distribution.

The invention provides as well a process wherein the obtained crystalline form is isolated by filtration or centrifugation, optionally combined with washing and drying. The starting material used for the processes of the present invention may be any crystalline or amorphous form of the ST-246, including a hydrate thereof.

In one aspect of the invention, the solvents employed in the preparation of the crystalline forms of the present invention are pharmaceutically acceptable or pharmaceutically non-acceptable solvents. Pharmaceutically non-acceptable solvents will have to be removed prior to using the polymorph into a pharmaceutical formulation.

The processes for the production of the polymorphic forms of the present invention typically include obtaining a crystalline solid material from a solution or dispersion of the ST-246 in a solvent medium, or from slurrying the ST-246, which can be initially in amorphous or crystalline form. The conditions concerning crystallization may be modified in order to improve the crystallization process or to induce precipitation, and without affecting the form of the polymorph obtained. These conditions include bringing the solution, dispersion, or slurry of the ST-246 and the solvent(s) to a desired concentration, cooling it following a defined cooling/temperature curve, adding crystal seeds, bringing the said solution, dispersion, or slurry to a desired temperature, effecting any suitable pressure, removing and/or separating any undesired material or impurities, drying the formed crystals to obtain the polymorphs in a solid state, if such state is desired.

One way of inducing precipitation is to reduce the solubility of the ST-246. The solubility of the compound may be reduced, for example, by cooling the solution. The solubility of the ST-246 may be reduced by adding an anti-solvent. Bringing the solution, dispersion, or slurry of the ST-246 and solvents to a desired concentration does not necessarily imply an increase in the concentration of the ST-246. In certain cases, a decrease or no change in concentration of the ST-246 could be preferable. The techniques used for obtaining a desired concentration include, for instance, evaporation by atmospheric distillation, vacuum distillation, fractioned distillation, azeotropic distillation, film evaporation, heating, cooling, other techniques well known in the art and combinations thereof. An optional process for obtaining a desired concentration could as well involve the saturation of the solution of the ST-246 and solvent, for example, by adding a sufficient volume of a non-solvent to the solution to reach the saturation point.

Other suitable techniques for saturating the solution include, by way of example, the introduction of additional ST-246 to the solution and/or evaporation of a portion of the solvent from the solution. As referred to herein, a saturated solution encompasses solutions at their saturation points or exceeding their saturation points, i.e. supersaturated. A nearly saturated solution refers to solutions that are near saturation but have not reached their saturation solubility limits.

In the preferred aspect of the invention, crystallization solvent is an important factor in determining which ST-246 polymorph is formed. Water content is also important, because the different polymorphic forms have varying levels of hydration. In the mixtures of water and water miscible solvents, the amount of water can vary from about 0.1% by volume to about 95% by volume, preferably from about 10% to about 20% by volume, more preferably from about 5% to about 10% by volume and most preferably from about 5% to about 1% of water.

ST-246 Polymorphic Forms I and III are monohydrates, and thus there is a minimum threshold of water that must be present in order for ST-246 to crystallize as a monohydrate. In addition, the cooling rate and isolation temperature and amount of water may play a role in determining which ST-246 polymorphic form and/or hydrate is formed. As summarized in Table 1 below, there is a correlation between cooling rate isolation temperature, water content and generation of ST-246 Form I or ST-246 Form III. Further, the data summarized in Table 1 suggests that the solvent composition, crystallization temperature, or cooling rate, may have an impact on ST-246 polymorph Form formation. For example, as shown in Table 1, when both isopropyl alcohol (IPA) and ethyl acetate are used as the major solvent, ST-246 Form III is generated when a warm, about 35° C. to about 40° C., solution containing higher water content is cooled directly into an ice bath. In contrast, in the presence of the lower water content or when solutions were cooled to room temperature for isolation, ST-246 Form I is obtained. Polymorphic form of the material prior to final crystallization does not impact final polymorph form, as long as the material completely dissolves in the crystallization solvent.

TABLE 1

Correlation between ST-246 Form formation, solvent system and isolation temperature.

| Solvent System | Isolation Temperature | Form |
| --- | --- | --- |
| IPA, 5% Water | Room Temperature | I |
| IPA, 5% Water | Ice Bath (2-5° C.) | III |
| IPA, 2% Water | Ice Bath | I |
| Ethyl acetate, 5% Water | Room Temperature | I |
| Ethyl acetate, 5% Water | Ice Bath (2-5° C.) | III |
| Ethyl acetate, 2% Water | Ice Bath (2-5° C.) | I |

Removing and/or separating any undesired material or impurities may be performed by purification, filtering, washing, precipitation or similar techniques. Separation, for example, can be conducted by known solid-liquid separation techniques. The filtrations can be performed, amongst other methods, by passing the solution, dispersion, or slurry through a filter paper, sintered glass filter or other membrane material, by centrifugation, or using Buchner style filter, Rosenmund filter or plates, or frame press. Preferably, in-line filtration or safety filtration may be advantageously intercalated in the processes disclosed above, in order to increase the polymorphic purity of the resulting crystalline form.

Crystals obtained may be also dried, and such drying process may optionally be used in the different crystallization passages, if more than one crystallization passage is applied. Drying procedures include all techniques known to those skilled in the art, such as heating, applying vacuum, circulating air or gas, adding a desiccant, freeze-drying, spray-drying, evaporating, or the like, or any combination thereof.

Form I.

In one aspect of the invention, the crystalline form of ST-246 is disclosed and is denominated as Form I of the ST-246, or in short "Form I".

One preferred parameter to reliably crystallize Form I is the use of ethyl acetate/water mixtures. Several parameters have been varied during crystallization studies with ethyl acetate/water (amount of water added, dissolving temperature, isolation temperature, cooling rate) and are summarized in Tables 1 and 2. Form I can be generated with the use of ethyl acetate/water mixture provided enough water is present to allow formation of the monohydrate. Further, Form I has been shown to be formed using THF/water mixtures, IPA/water mixtures, and both acetone and methanol have shown the ability to crystallize Form I with higher levels of water. In addition, Form I can also be generated by holding a water slurry of Forms III and V for several days or longer.

TABLE 2

Crystallization Parameters

| | | Dissolving | | Treatment for precipitation | | Drying |
|---|---|---|---|---|---|---|
| No. | Solvent | Water % | Temp (° C.) | Temp (° C.) | Time (hours) | Temp (° C.) |
| 4 | IPA/Water | 5 | 55-60 | RT | 14 | 50 |
| 5 | IPA/Water | 5 | 55-60 | RT: Ice bath | 14: 2-4 | 50 |
| 8 | IPA/Water | 2 | 35-40 | Ice bath | 22 | 50 |
| 13 | IPA/Water | 5 | | | | 50-55 |

TABLE 2-continued Crystallization Parameters

| # | Solvent | Ratio | Temp1 | Temp2 | Time | Final Temp |
|---|---|---|---|---|---|---|
| 14 | IPA/Water | 2.85 | | | | 55-60 |
| 15 | IPA/Water | 2.85 | | | | 55-60 |
| 16 | IPA/Water | 2.85 | | | | 55-60 |
| | Ethyl Acetate/Water# | 3 | 70-80 | RT | 20 | 75 C. |
| 27 | Ethyl Acetate/Water | 5 | 70-80 | RT | 5.5 | 50 |
| 29 | Ethyl Acetate/Water | 5 | 55-60 | RT: Ice bath | 14: 2-4 | 50 |
| 30 | Ethyl Acetate/Water | 2 | 55-60 | RT | 14 | 50 |
| 32 | Ethyl Acetate/Water | 2 | 35-40 | Ice bath | 22 | 50 |
| 36 | Ethyl Acetate → Water | 5 | 50-60 | RT | O/N | 50-60 |
| 37 | Ethyl Acetate → Water | 10 | 50-60 | RT | O/N | 50-60 |
| 38 | Ethyl Acetate → Water | 20 | 50-60 | RT | O/N | 50-60 |
| 39 | Ethyl Acetate → Water | 40 | 50-60 | RT | O/N | 50-60 |
| 40 | Ethyl Acetate | — | | | | 55-60 |
| 41 | Ethyl Acetate/Water | 2 | | | | 55-60 |
| 42 | Ethyl Acetate/Water | 3 | | | | 55-60 |
| 43 | Ethyl Acetate/Water | 2 | | | | 55-60 |
| 44 | Ethyl Acetate/Water | 3 | | | | 55-60 |
| 45 | Ethyl Acetate/Water | 2 | | | | 40-47 |
| 46 | Ethyl Acetate/Water | 5 | | | | 40-45 |
| 47 | Ethyl Acetate/Water | 5 | | | | 40-45 |
| 48 | Ethyl Acetate/Water | 2 | | | | 40-45 |
| 49 | Ethyl Acetate/Water | 2 | | | | 40-45 |
| 50 | Ethyl Acetate/Water | 2 | | | | 40-45 |
| 62 | Ethanol/Water (60° C.) | 10 | 60 | RT: 2-8 | 3: 4 | 50-60 |
| 63 | Ethanol/Water | 3 | | | | 55-60 |
| 64 | Ethanol/Water | 3 | | | | 55-60 |
| 66 | Methanol/Water | 5 | 55-60 | RT: Ice bath | 14: 2-4 | 50 |
| 68 | Methanol/Water | 5 | 35-40 | Ice bath | 22 | 50 |
| 71 | Acetone/Water | 7.5 | 55-60 | RT: Ice bath | 14: 2-4 | 50 |
| 77 | THF/Water | 7.5 | 55-60 | RT: Ice bath | 14: 2-4 | 50 |
| 78 | THF/Water | 2 | 55-60 | RT | 14 | 50 |
| 79 | THF/Water | 5 | 35-40 | Ice bath | 22 | 50 |
| 80 | THF/Water | 2 | 35-40 | Ice bath | 22 | 50 |
| 83 | Isopropyl Acetate/Water | 5 | 55-60 | RT: Ice bath | 14: 2-4 | 50 |
| 84 | Isopropyl Acetate/Water | 2 | 55-60 | RT | 14 | 50 |
| 96 | Water Slurry | 100 | 45: RT | NA | | |
| 61 | Ethanol/Water (60° C.) | 10 | 60 | RT: 2-8 | 3: 4 | 50-60 |
| 1 | IPA | — | 70-80 | RT | 72 | 75 |
| 7 | IPA/Water | 5 | 35-40 | Ice bath | 22 | 50 |
| 17 | IPA/Water | 2.85 | | | | 55-60 |
| 18 | IPA/Water | 2.85 | | | | 55-60 |
| 19 | IPA/Water | 5 | | | | 55-60 |
| 20 | IPA/Water | 5 | | | | 55-60 |
| 21 | IPA/Water | 2.85 | | | | 55-60 |
| 22 | IPA/Water | 5 | | | | 55-60 |
| 23 | IPA/Water | 5 | | | | 55-60 |
| 24 | IPA/Water | 1.25 | | | | 40-45 |
| 31 | Ethyl Acetate/Water | 5 | 35-40 | Ice bath | 22 | 50 |
| 56 | Ethyl Acetate:Hexane (7:4) | — | 70 | RT: 2-8 | 3: 4 | 50-60 |
| 72 | Acetone/Water | 2 | 55-60 | RT | 15 | 50 |
| 88 | Water Slurry | 100 | RT: 50 | NA | | |
| 90 | Water Slurry | 100 | | NA | | |
| 91 | Water Slurry | 100 | RT | NA | | RT |
| 92 | Water Slurry | 100 | 45 | NA | | RT |
| 93 | Water Slurry | 100 | RT | NA | | 37 |
| 94 | Water Slurry | 100 | RT | NA | | 37 |
| 95 | Water Slurry (14KM71A) | 100 | 60 | NA | | |
| 6 | IPA/Water | 2 | 55-60 | RT | 14 | 50 |
| 25 | Ethyl Acetate | — | 70-80 | RT | 72 | 75 |
| 55 | Ethyl Acetate:Hexane (7:4) | — | 70 | RT: 2-8 | 3: 4 | 50-60 |
| 58 | Ethanol | — | 70-80 | RT | 72 | 75 |
| 67 | Methanol/Water | 2 | 55-60 | RT | 15 | 50 |
| 69 | Methanol/Water | 2 | 35-40 | Ice bath | 22 | 50 |
| 61 | Ethanol/Water (60° C.) | 10 | 60 | RT: 2-8 | 3: 4 | 50-60 |
| 1 | IPA | — | 70-80 | RT | 72 | 75 |
| 7 | IPA/Water | 5 | 35-40 | Ice bath | 22 | 50 |
| 17 | IPA/Water | 2.85 | | | | 55-60 |
| 18 | IPA/Water | 2.85 | | | | 55-60 |
| 19 | IPA/Water | 5 | | | | 55-60 |
| 20 | IPA/Water | 5 | | | | 55-60 |
| 21 | IPA/Water | 2.85 | | | | 55-60 |
| 22 | IPA/Water | 5 | | | | 55-60 |
| 23 | IPA/Water | 5 | | | | 55-60 |
| 24 | IPA/Water | 1.25 | | | | 40-45 |
| 31 | Ethyl Acetate/Water | 5 | 35-40 | Ice bath | 22 | 50 |
| 56 | Ethyl Acetate:Hexane (7:4) | — | 70 | RT: 2-8 | 3: 4 | 50-60 |
| 72 | Acetone/Water | 2 | 55-60 | RT | 15 | 50 |
| 88 | Water Slurry | 100 | RT: 50 | NA | | |

TABLE 2-continued

| | | Crystallization Parameters | | | | | |
|---|---|---|---|---|---|---|---|
| 90 | Water Slurry | 100 | RT | NA | | | RT |
| 91 | Water Slurry | 100 | RT | NA | | | RT |
| 92 | Water Slurry | 100 | 45 | NA | | | RT |
| 93 | Water Slurry | 100 | RT | NA | | | 37 |
| 94 | Water Slurry | 100 | RT | NA | | | 37 |
| 95 | Water Slurry (14KM71A) | 100 | 60 | NA | | | |
| 6 | IPA/Water | 2 | 55-60 | RT | | 14 | 50 |
| 25 | Ethyl Acetate | — | 70-80 | RT | | 72 | 75 |
| 55 | Ethyl Acetate:Hexane (7:4) | — | 70 | RT: 2-8 | | 3: 4 | 50-60 |
| 58 | Ethanol | — | 70-80 | RT | | 72 | 75 |
| 67 | Methanol/Water | 2 | 55-60 | RT | | 15 | 50 |
| 69 | Methanol/Water | 2 | 35-40 | Ice bath | | 22 | 50 |

| No. | Solvent | Polymorph Form | Melting Point (° C.) | NB ref. | Recrystallization/ Batch # |
|---|---|---|---|---|---|
| 4 | IPA/Water | I | 197.9 | DN-383-15 | 383-18-A-1 |
| 5 | IPA/Water | | 197.8 | DN-383-15 | 383-18-A-1-2 |
| 8 | IPA/Water | | 197.7 | DN-383-19 | |
| 13 | IPA/Water | | | | 14KM24C |
| 14 | IPA/Water | | | | 14KM53D |
| 15 | IPA/Water | | | | 14KM54B |
| 16 | IPA/Water | | | | 14KM54D |
| | Ethyl Acetate/Water# | | | | DN-383-1 |
| 27 | Ethyl Acetate/Water | | 197.3 | DN-383-9 | |
| 29 | Ethyl Acetate/Water | | 198 | DN-383-15 | 383-18-B-1-2 |
| 30 | Ethyl Acetate/Water | | 197.7 | DN-383-15 | 383-18-B-2 |
| 32 | Ethyl Acetate/Water | | 197.9 | DN-383-19 | |
| 36 | Ethyl Acetate → Water | | | MAS-518-88 | MAS-518-88-1 |
| 37 | Ethyl Acetate → Water | | | MAS-518-88 | MAS-518-88-2 |
| 38 | Ethyl Acetate → Water | | | MAS-518-88 | MAS-518-88-3 |
| 39 | Ethyl Acetate → Water | | | MAS-518-88 | MAS-518-88-4 |
| 40 | Ethyl Acetate | | | | 14KM40C |
| 41 | Ethyl Acetate/Water | | | | 14KM40D |
| 42 | Ethyl Acetate/Water | | | | 14KM46B |
| 43 | Ethyl Acetate/Water | | | | 14KM48B |
| 44 | Ethyl Acetate/Water | | | | 14KM57E |
| 45 | Ethyl Acetate/Water | | | | 14KM75B (400 g) |
| 46 | Ethyl Acetate/Water | | | | 14KM77A (200 g) |
| 47 | Ethyl Acetate/Water | | | | 14KM79B (200 g) |
| 48 | Ethyl Acetate/Water | | | | 14KM98B (200 g) |
| 49 | Ethyl Acetate/Water | | | | 15KM16A (400 g) |
| 50 | Ethyl Acetate/Water | | | | 15KM18B (400 g) |
| 62 | Ethanol/Water (60° C.) | | | MAS-518-88 | MAS-518-88-6 |
| 63 | Ethanol/Water | | | | 14KM36C |
| 64 | Ethanol/Water | | | | 14KM36D |
| 66 | Methanol/Water | | 197.6 | DN-383-15 | 383-18-C-1-2 |
| 68 | Methanol/Water | | 197.8 | DN-383-19 | |
| 71 | Acetone/Water | | 199.1 | DN-383-15 | 383-18-D-1-2 |
| 77 | THF/Water | | | DN-383-15 | 383-18-E-1-2 |
| 78 | THF/Water | | | DN-383-15 | 383-18-E-2 |
| 79 | THF/Water | | | DN-383-19 | |
| 80 | THF/Water | | | DN-383-19 | |
| 83 | Isopropyl Acetate/Water | | | DN-383-15 | 383-18-F-1-2 |
| 84 | Isopropyl Acetate/Water | | | DN-383-15 | 383-18-F-2 |
| 96 | Water Slurry | | | | |
| 61 | Ethanol/Water (60° C.) | I and III | | MAS-518-88 | MAS-518-88-5 |
| 1 | IPA | III | 198.3 | DN-383-1 | 0374-24 |
| 7 | IPA/Water | | 197.7 | DN-383-19 | |
| 17 | IPA/Water | | | | 14KM23D |
| 18 | IPA/Water | | | | 14KM38A |
| 19 | IPA/Water | | | | 14KM41A |
| 20 | IPA/Water | | | | 14KM49B |
| 21 | IPA/Water | | | | 14KM60E |
| 22 | IPA/Water | | | | 14KM64C |
| 23 | IPA/Water | | | | 14KM64D |
| 24 | IPA/Water | | | | 14KM73B |
| 31 | Ethyl Acetate/Water | | 197.9 | DN-383-19 | |
| 56 | Ethyl Acetate:Hexane (7:4) | | | MAS-518-88 | MAS-518-88-8 |
| 72 | Acetone/Water | | 197.5 | DN-383-15 | 383-18-D-2 |
| 88 | Water Slurry | | 197.5 | DN-383-23 | ST-246W |
| 90 | Water Slurry | | 197.5 | | |
| 91 | Water Slurry | | 197.9 | DN-383-34 | 0383-34 |
| 92 | Water Slurry | | 197.8 | DN-383-34 | 0383-34 |
| 93 | Water Slurry | | | WW-386-20 | #51 |
| 94 | Water Slurry | | | WW-386-22 | #54 |
| 95 | Water Slurry (14KM71A) | | | | |
| 6 | IPA/Water | V | 198.1 | DN-383-15 | 383-18-A-2 |

TABLE 2-continued

Crystallization Parameters

| | | | | | |
|---|---|---|---|---|---|
| 25 | Ethyl Acetate | | 197.9 | DN-383-1 | 0374-26 |
| 55 | Ethyl Acetate:Hexane (7:4) | | | MAS-518-88 | MAS-518-88-7 |
| 58 | Ethanol | | 197.9 | DN-383-1 | 0374-28 |
| 67 | Methanol/Water | | 197.6 | DN-383-15 | 383-18-C-2 |
| 69 | Methanol/Water | | 197.9 | DN-383-19 | |
| 61 | Ethanol/Water (60° C.) | I and III | | MAS-518-88 | MAS-518-88-5 |
| 1 | IPA | III | 198.3 | DN-383-1 | 0374-24 |
| 7 | IPA/Water | | 197.7 | DN-383-19 | |
| 17 | IPA/Water | | | | 14KM23D |
| 18 | IPA/Water | | | | 14KM38A |
| 19 | IPA/Water | | | | 14KM41A |
| 20 | IPA/Water | | | | 14KM49B |
| 21 | IPA/Water | | | | 14KM60E |
| 22 | IPA/Water | | | | 14KM64C |
| 23 | IPA/Water | | | | 14KM64D |
| 24 | IPA/Water | | | | 14KM73B |
| 31 | Ethyl Acetate/Water | | 197.9 | DN-383-19 | |
| 56 | Ethyl Acetate:Hexane (7:4) | | | MAS-518-88 | MAS-518-88-8 |
| 72 | Acetone/Water | | 197.5 | DN-383-15 | 383-18-D-2 |
| 88 | Water Slurry | | 197.5 | DN-383-23 | ST-246W |
| 90 | Water Slurry | | 197.5 | | |
| 91 | Water Slurry | | 197.9 | DN-383-34 | 0383-34 |
| 92 | Water Slurry | | 197.8 | DN-383-34 | 0383-34 |
| 93 | Water Slurry | | | WW-386-20 | #51 |
| 94 | Water Slurry | | | WW-386-22 | #54 |
| 95 | Water Slurry (14KM71A) | | | | |
| 6 | IPA/Water | V | 198.1 | DN-383-15 | 383-18-A-2 |
| 25 | Ethyl Acetate | | 197.9 | DN-383-1 | 0374-26 |
| 55 | Ethyl Acetate:Hexane (7:4) | | | MAS-518-88 | MAS-518-88-7 |
| 58 | Ethanol | | 197.7 | DN-383-1 | 0374-28 |
| 67 | Methanol/Water | | 197.6 | DN-383-15 | 383-18-C-2 |
| 69 | Methanol/Water | | 197.9 | DN-383-19 | |

Form I is a monohydrate crystalline form of ST-246. Examples of X-Ray Diffraction (XRPD), data for Form I are summarized in FIG. 1 and are shown below:

| Angle 2-Theta | d value Angstrom | Intensity Cps | Intensity % |
|---|---|---|---|
| 7.63 | 11.58 | 5.92 | 5.5 |
| 10.04 | 8.80 | 35.5 | 33.3 |
| 11.47 | 7.71 | 26.8 | 25.1 |
| 14.73 | 6.01 | 13.8 | 12.9 |
| 15.21 | 5.82 | 7.67 | 7.2 |
| 15.47 | 5.72 | 14.0 | 13.1 |
| 16.06 | 5.51 | 20.4 | 19.1 |
| 16.67 | 5.31 | 21.5 | 20.1 |
| 16.98 | 5.22 | 9.21 | 8.6 |
| 18.93 | 4.68 | 107 | 100.0 |
| 19.96 | 4.45 | 29.4 | 27.5 |
| 20.52 | 4.32 | 12.5 | 11.7 |
| 20.79 | 4.27 | 48.2 | 45.2 |
| 22.80 | 3.90 | 79.6 | 74.5 |
| 25.16 | 3.54 | 4.17 | 3.9 |
| 26.53 | 3.36 | 14.0 | 13.1 |
| 27.20 | 3.28 | 8.55 | 8.0 |
| 27.60 | 3.23 | 9.21 | 8.6 |
| 29.60 | 3.02 | 10.7 | 10.1 |
| 30.23 | 2.95 | 48.5 | 45.4 |
| 30.49 | 2.93 | 69.5 | 65.1 |
| 30.68 | 2.91 | 25.0 | 23.4 |
| 31.14 | 2.87 | 7.67 | 7.2 |
| 33.65 | 2.66 | 104 | 97.3 |
| 34.33 | 2.61 | 16.9 | 15.8 |
| 35.29 | 2.54 | 10.1 | 9.4 |
| 35.56 | 2.52 | 19.5 | 18.3 |
| 36.30 | 2.47 | 11.8 | 11.1 |
| 37.36 | 2.41 | 32.9 | 30.8 |
| 38.42 | 2.34 | 3.51 | 3.3 |
| 38.66 | 2.33 | 28.7 | 26.9 |

The characteristic infrared spectrum of Form I is described below and is summarized in FIG. 7.

The Region from 4000 to 400 $cm^{-1}$

Form I has a large single peak at 3421 $cm^{-1}$ and also have a broad absorbance underlying these peaks, from approximately 3300 to 2600 $cm^{-1}$. There are also two peaks at 3008 and 2956 $cm^{-1}$, likely due to C—H stretch. Form I has peaks at 1791, 1717 and 1671 $cm^{-1}$. All three forms have a peak at approximately 1560 $cm^{-1}$ ST-246 Form I is the desired polymorph of ST-246. It appears to be the thermodynamically most stable form, as all other get converted to Form-I.

ST-246 Form I is stable and hence can be stored at ambient conditions. Form I has not been shown to convert to another polymorphic form under several environmental and process conditions that a drug could experience during various stages of manufacturing and storage. Some of the conditions tested include storage at high temperature and high humidity, room temperature and high humidity, low humidity, up to 60° C., capsule manufacturing using wet granulation and drying, during milling or micronization process, in suspension, long term storage at room temperature. Further, Form-I is non hygroscopic and hence does not absorb moisture even at 90% relative humidity conditions. Form I is reliably manufactured by the commercial process crystallization process with more than 99.0% purity and with impurities not more than 0.15%.

Form II

In another aspect of the invention, the crystalline form of ST-246 is disclosed and is denominated as Form II of the ST-246, or in short "Form II".

ST-246 Form II has been obtained in the presence of some alcohols, as well as acetone/IPA mixtures. In the preferred aspect of the invention, Form II is reliably crystallized in the presence of ethyl acetate or chloroform. Anhydrate Form II is relatively unstable and prone to conversion to Form III due to absorption of moisture.

Form II is an anhydrate crystalline form of ST-246. Examples of X-Ray Diffraction (XRPD) are summarized in FIG. 2.

Form III

In another aspect of the invention, the invention concerns the crystalline form of ST-246 that is denominated as Form III of the ST-246, or in short "Form III".

As summarized in Tables 1 and 2, IPA/water mixtures, at various water levels, tend to give Form III. Further, Form III can be generated from a water slurry of Form V. Based on the data summarized in Table 1, a faster cooling rate and lower isolation temperature may tend to yield Form III.

Figure 3:
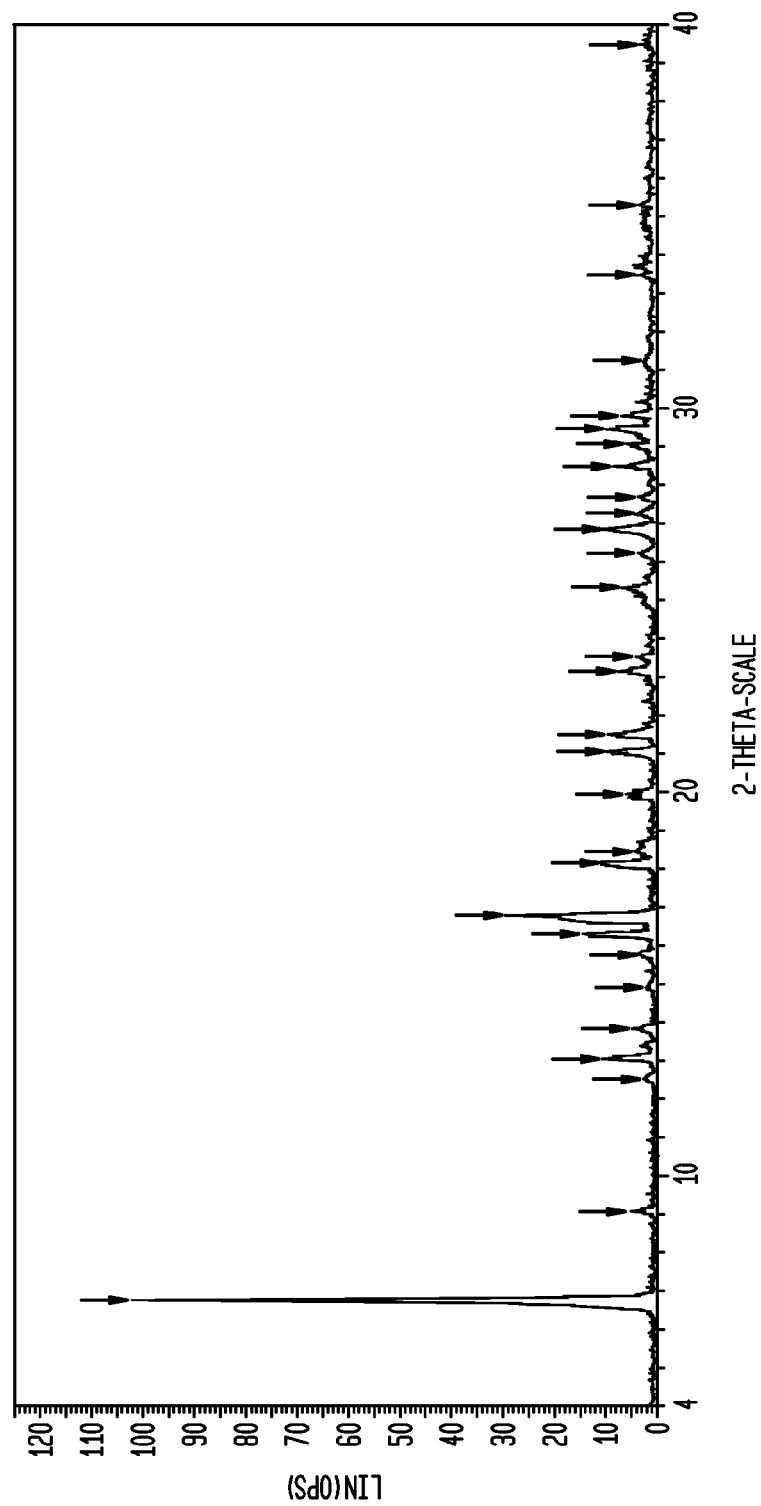
FIG. 3 shows an X-ray powder diffraction (XRPD) pattern of Form III.

Form III is a monohydrate crystalline form of ST-246. Examples of a single crystal X-Ray Diffraction (XRPD) data for Form III are shown in FIG. 3 and summarized below:

| Angle 2-Theta | d value Angstrom | Intensity Cps | Intensity % |
| --- | --- | --- | --- |
| 6.71 | 13.15 | 102 | 100.0 |
| 9.05 | 9.76 | 5.23 | 5.1 |
| 12.49 | 7.08 | 2.77 | 2.7 |
| 13.03 | 6.79 | 11.2 | 11.0 |
| 13.79 | 6.42 | 4.61 | 4.5 |
| 14.87 | 5.95 | 2.56 | 2.5 |
| 15.72 | 5.63 | 3.79 | 3.7 |
| 16.26 | 5.45 | 14.8 | 14.5 |
| 16.74 | 5.29 | 30.3 | 29.7 |
| 18.10 | 4.90 | 11.4 | 11.2 |
| 18.43 | 4.81 | 4.51 | 4.4 |
| 19.94 | 4.45 | 6.46 | 6.3 |
| 21.04 | 4.22 | 10.0 | 9.8 |
| 21.51 | 4.13 | 9.64 | 9.4 |
| 23.15 | 3.84 | 7.28 | 7.1 |
| 23.51 | 3.78 | 4.10 | 4.0 |
| 25.32 | 3.51 | 7.28 | 7.1 |
| 26.24 | 3.39 | 3.79 | 3.7 |
| 26.87 | 3.32 | 11.2 | 11.0 |
| 27.32 | 3.26 | 4.31 | 4.2 |
| 27.72 | 3.22 | 3.69 | 3.6 |
| 28.55 | 3.12 | 9.12 | 8.9 |
| 29.08 | 3.07 | 5.84 | 5.7 |
| 29.50 | 3.03 | 9.84 | 9.6 |
| 29.84 | 2.99 | 6.66 | 6.5 |
| 31.27 | 2.86 | 2.46 | 2.4 |
| 33.48 | 2.67 | 3.59 | 3.5 |
| 35.36 | 2.54 | 3.38 | 3.3 |
| 39.56 | 2.28 | 3.49 | 3.4 |

The characteristic infrared spectrum of the Form III is described below and summarized in FIG. 8.

The Region from 4000 to 2500 $cm^{-1}$

Form III has a split peak at 3452 and 3397 $cm^{-1}$. There is also a peak at ~3008 and 2956 $cm^{-1}$, likely due to C—H stretch. There are also peaks at from approximately 3300 to 2600 $cm^{-1}$.

The Region from 2000 to 1500 $cm^{-1}$

Form III has a set of peaks at 1792, 1713 and 1662 $cm^{-1}$. All of these are likely due to C=O stretches. There is also a peak at 1560 $cm^{-1}$, tentatively assigned to N—H deformation.

The Region from 1500 to 400 $cm^{-1}$

From approximately 1500 to 400 $cm^{-1}$, there are a variety of less significant peaks.

Form III (monohydrate) can be converted to Form I in competitive slurry experiments. Conversion from Form I to Form III has never been observed, suggesting that Form I is a more thermodynamically stable Form than Form III. However, Form III has an advantage over other less hydrated forms such as for example Form V in that Form III is fully hydrated and does not absorb any further amount of moisture under humid storage conditions.

Form IV

Figure 4:
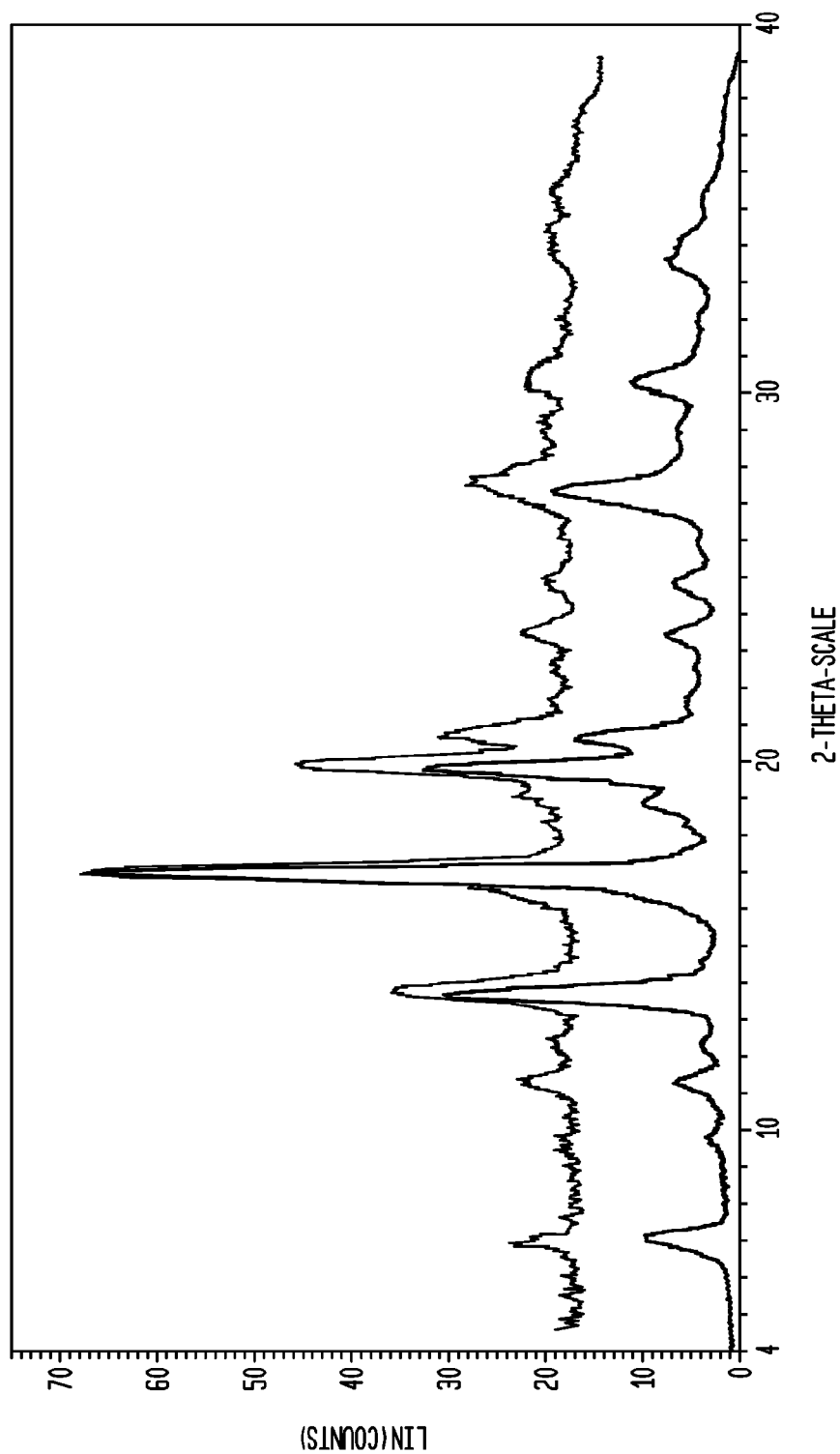
FIG. 4 shows two X-ray powder diffraction (XRPD) patterns of Form IV (from two different samples).

Examples of XRPD, single crystal X-ray data for Form IV are shown in FIG. 4.

In a preferred aspect of the invention, Form IV is formed in the presence of chlorinated solvents and some alcohols such as for example, TFE, 1 butanol, toluene, methylene chloride, chloroform, among others. Anhydrate Form IV is relatively unstable and prone to conversion to Form V, due to absorption of moisture.

Form V

In yet another aspect of the invention, the invention concerns the crystalline form of ST-246 that is denominated as Form V of the ST-246, or in short "Form V".

Form V is a hemihydrate crystalline form of ST-246. Examples of XRPD data for Form V are shown below and summarized in FIG. 5.

| Angle 2-Theta ° | d value Angstrom | Intensity Cps | Intensity % |
| --- | --- | --- | --- |
| 6.39 | 13.81 | 101 | 100.0 |
| 6.72 | 13.14 | 9.56 | 9.5 |
| 8.16 | 10.82 | 1.88 | 1.9 |
| 9.04 | 9.78 | 3.75 | 3.7 |
| 9.52 | 9.28 | 6.38 | 6.3 |
| 10.52 | 8.41 | 4.88 | 2.1 |
| 12.40 | 7.13 | 5.06 | 5.0 |
| 12.79 | 6.92 | 7.31 | 7.3 |
| 13.38 | 6.61 | 4.13 | 4.1 |
| 14.15 | 6.25 | 12.0 | 11.9 |
| 14.57 | 6.07 | 11.4 | 11.4 |
| 15.84 | 5.59 | 15.9 | 15.9 |
| 16.32 | 5.43 | 10.7 | 10.6 |
| 16.67 | 5.31 | 25.7 | 25.6 |
| 17.50 | 5.06 | 21.2 | 21.1 |
| 18.13 | 4.89 | 9.19 | 9.1 |
| 18.48 | 4.80 | 5.44 | 5.4 |
| 18.78 | 4.72 | 16.9 | 16.8 |
| 19.79 | 4.48 | 38.3 | 38.1 |
| 20.68 | 4.29 | 17.3 | 17.2 |
| 21.07 | 4.21 | 13.9 | 13.8 |
| 21.54 | 4.12 | 5.25 | 5.2 |
| 22.01 | 4.04 | 5.81 | 5.8 |
| 22.73 | 3.91 | 7.50 | 7.5 |
| 23.60 | 3.77 | 6.38 | 6.3 |
| 25.25 | 3.52 | 4.50 | 4.5 |
| 25.73 | 3.46 | 20.1 | 20.0 |
| 26.27 | 3.39 | 3.94 | 3.9 |
| 26.73 | 3.33 | 5.63 | 5.6 |
| 27.24 | 3.27 | 13.3 | 13.2 |
| 29.02 | 3.07 | 10.1 | 10.1 |
| 29.50 | 3.03 | 8.06 | 8.0 |
| 29.83 | 2.99 | 6.94 | 6.9 |
| 30.44 | 2.93 | 9.00 | 9.0 |
| 32.04 | 2.79 | 4.50 | 4.5 |
| 33.52 | 2.67 | 7.13 | 7.1 |
| 34.84 | 2.57 | 4.69 | 4.7 |
| 35.68 | 2.51 | 6.19 | 6.2 |
| 39.78 | 2.26 | 4.31 | 4.3 |

Figure 9:
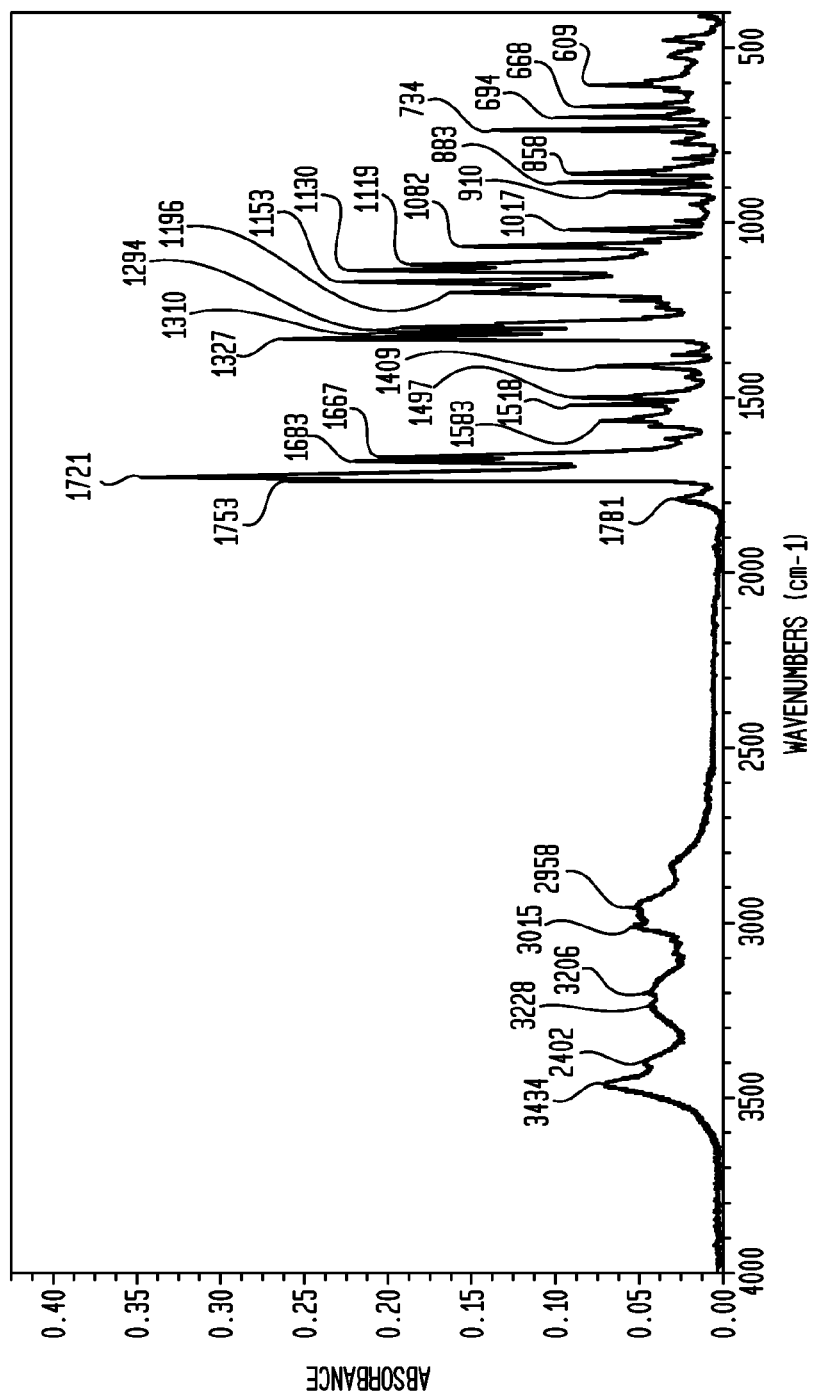
FIG. 9 depicts Fourier transform infra red (FTIR) spectrum of Form V.
Figure 10:
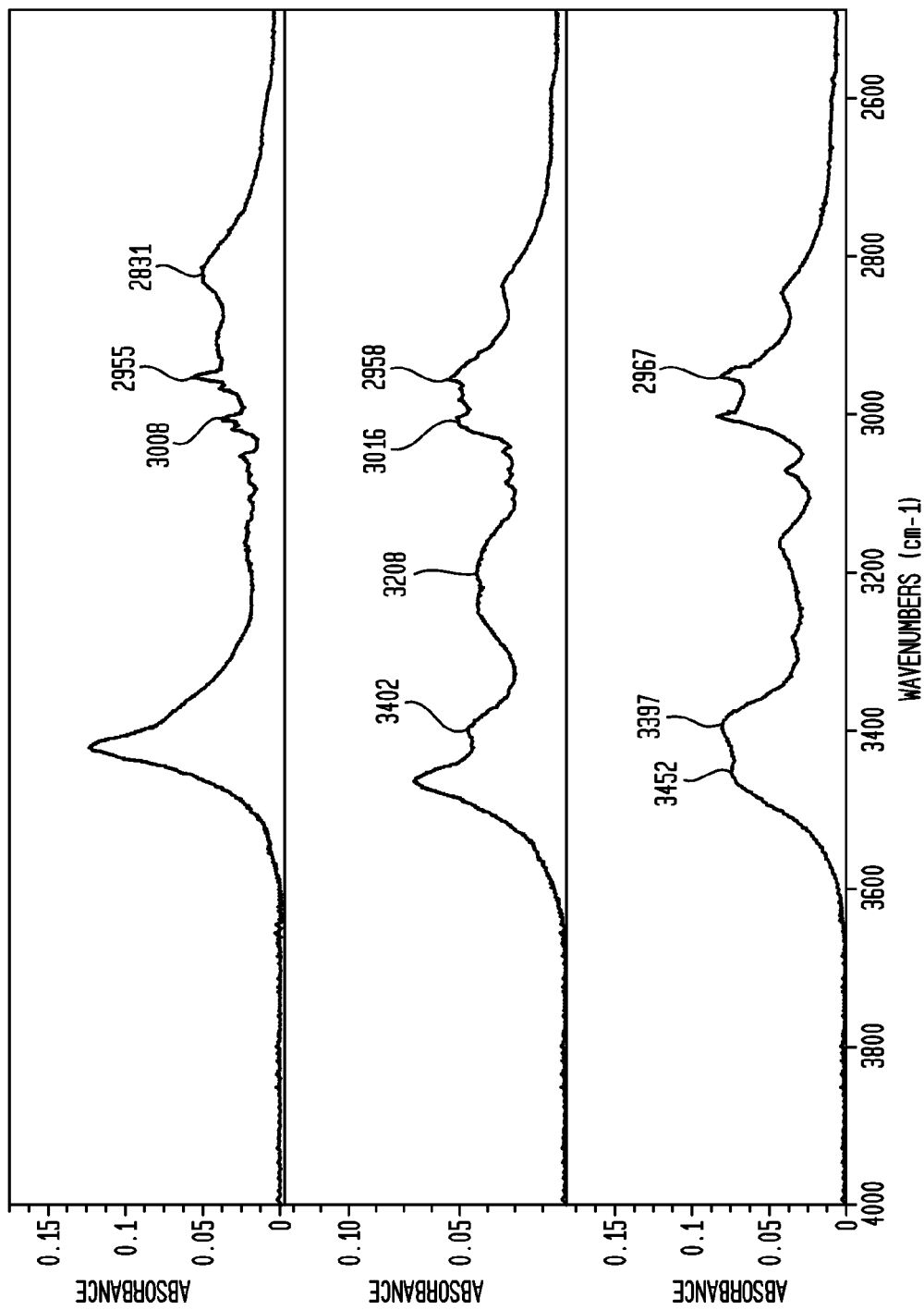
FIGS. 10, 11, 12 and 13, depict magnified view of FTIR Spectra of Form I (upper panel), Form V (middle panel) and Form III (lower panel).
Figure 11:
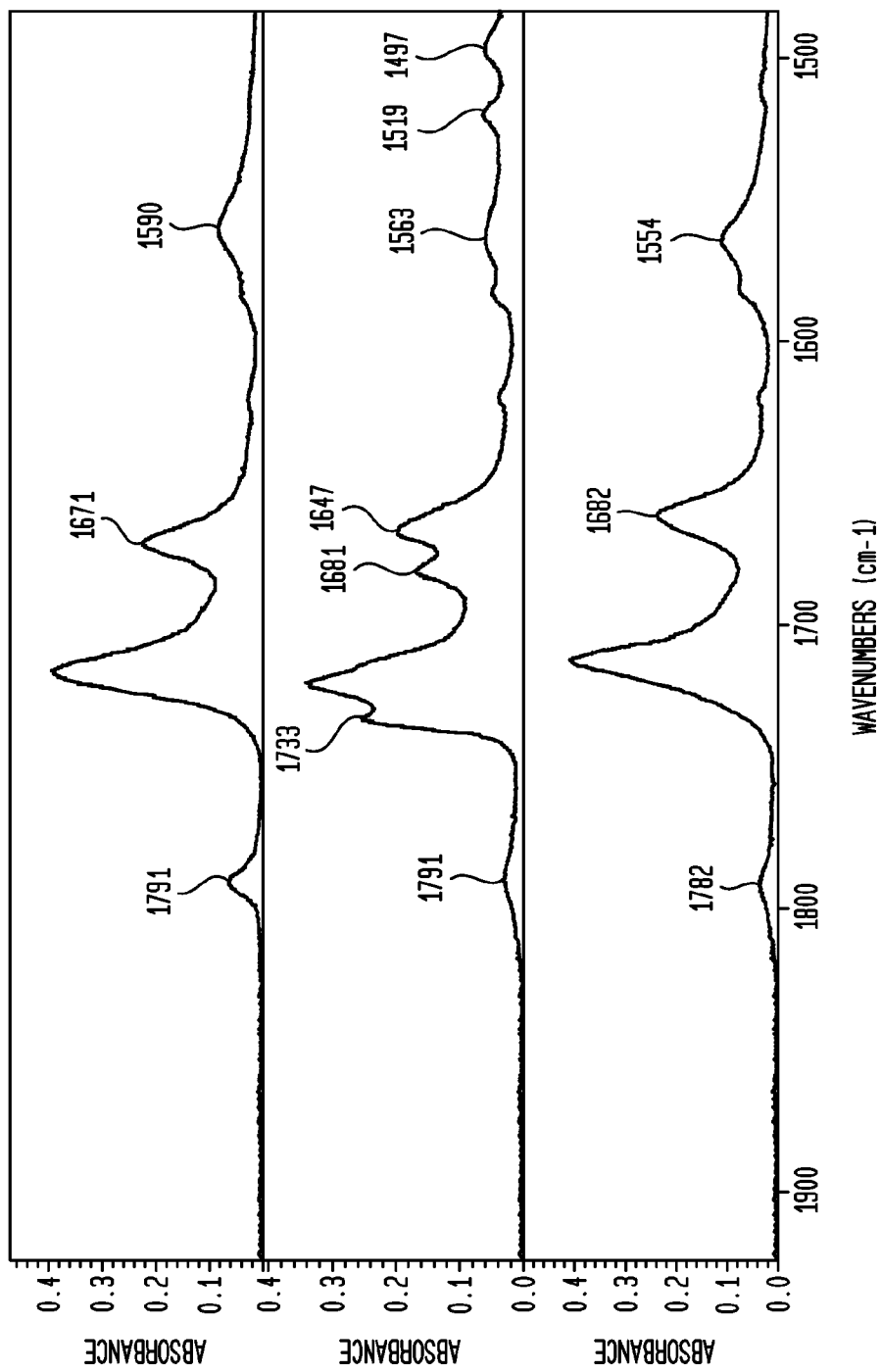
Figure 12:
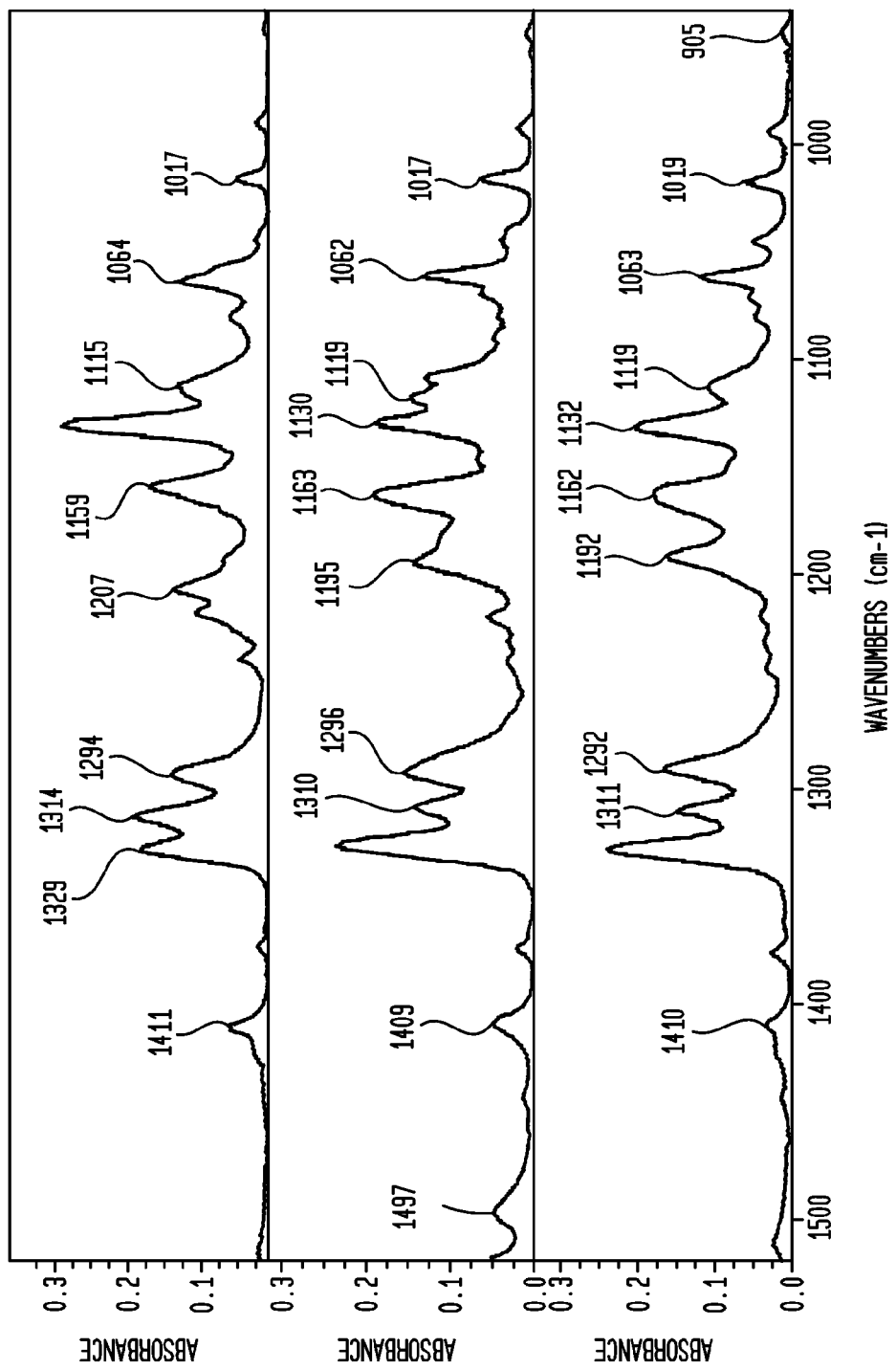
Figure 13:
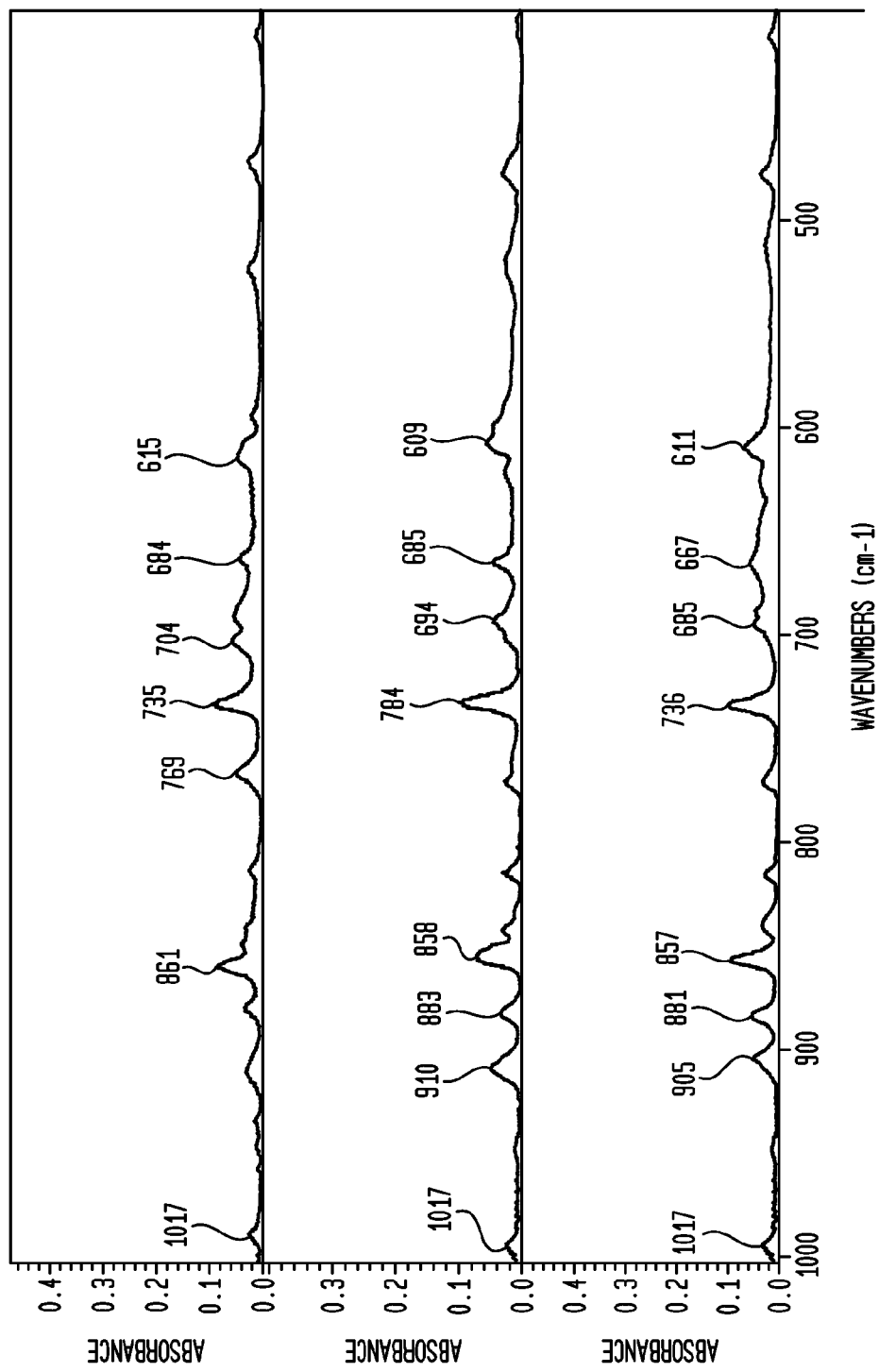

The infrared spectrum of the Form V has also been summarized in FIG. 9 and is described below. The underlined peaks are considered the most characteristics of the polymorph:

The Region from 4000 to 2500 $cm^{-1}$

Form V has a split peak at 3464 and 3402 $cm^{-1}$ along with a second broad split peak at 3238 and 3206 $cm^{-1}$. These peaks are likely due to OH and NH stretches and appear to allow differentiation of the three forms. Form V also has peaks at ~3008 and 2956 $cm^{-1}$, likely due to C—H stretch. There are further peaks at approximately 3300 to 2600 $cm^{-1}$.

The Region from 2000 to 1500 $cm^{-1}$

Form V has significantly different spectral characteristics in this region as compared to other polymorphic forms of ST-246, showing 5 peaks rather than 3, and these are at 1791, 1733, 1721, 1681 and 1667 cm$^{-1}$. All of these are likely due to C=O stretches. All three forms have a peak at approximately 1560 cm$^{-1}$, tentatively assigned to N—H deformation. Form V has peaks at 1519 and 1497 cm$^{-1}$.

The Region from 1500 to 400 cm$^{-1}$

From approximately 1500 to 400 cm$^{-1}$, the infrared spectra of the three forms show only slight differences, and this region is probably not useful for differentiating the three forms of ST-246 discussed here.

Form V (hemi-hydrate) was made during early GMP syntheses of ST-246 and is disclosed in WO 2008/130348, WO 2004/112718 and WO 2008/079159. The disadvantage of this polymorph is that it is not fully hydrated. This form readily absorbs moisture when placed in a humid environment, and has been shown to convert to Form I in competitive slurry experiments.

Form V tends to form when insufficient water is present to generate the monohydrate form. Form V is formed from ethyl acetate/hexane mixtures when the starting ST-246 used for crystallization does not contain water. If the starting ST-246 contains enough water, Form III can be formed. Form V has also been generated by methanol/water and IPA/water mixtures containing low levels of water.

Form VI

In one aspect of the invention, the invention concerns the crystalline form of ST-246 that is denominated as Form VI of the ST-246, or in short "Form VI".

Figure 6:
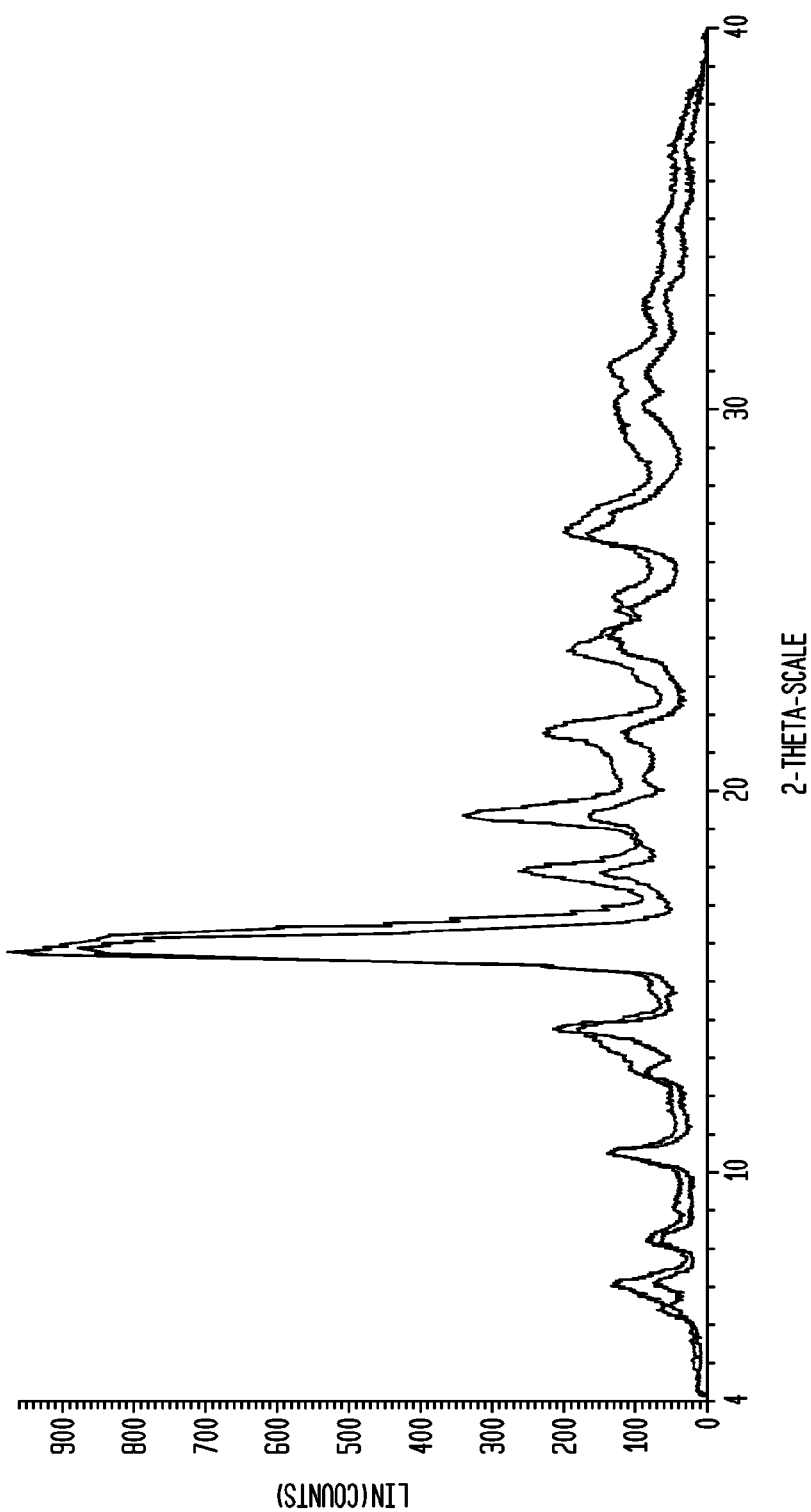
FIG. 6 shows two an X-ray powder diffraction (XRPD) patterns of Form VI (from two different samples).

Form VI is an monohydrate crystalline form of ST-246. Examples of XRPD are summarized in FIG. 6. In the preferred aspect of the invention, Form VI may be formed, as an example, in the presence of nitromethane or chloroform/methanol as crystallization solvents.

In preparing polymorph Forms I, II, III, IV, and V substantially free of other polymorph forms, crystallization from a mixture of different forms is generally utilized. However, the crystallization technique with regard to producing each of these polymorph forms substantially free of other polymorph forms is different and described below.

More specifically, the present invention provides isolated Form I that is at least about 70% pure (i.e. free of other forms), preferably at least about 80% pure, preferably at least about 90% pure, preferably at least about 95% pure, more preferably at least about 99% pure, and most preferably at least about 99.9% pure.

The present invention provides for isolated Form II which is at least about 70% pure (i.e. free of other forms), preferably at least about 80% pure, preferably at least about 90% pure, more preferably at least about 99% pure, and most preferably at least about 99.9% pure. Further, the present invention provides for isolated Form III which is at least about 70% pure, preferably at least about 80% pure, preferably at least about 90% pure, preferably at least about 95% pure, more preferably at least about 99% pure, and most preferably at least about 99.9% pure.

Also, the present invention provides for isolated Form IV which is at least about 70% pure (i.e. free of other forms), preferably at least about 80% pure, preferably at least about 90% pure, preferably at least about 95% pure, more preferably at least about 99% pure, and most preferably at least about 99.9% pure.

Further, the present invention provides for isolated Form VI which is at least about 70% pure (i.e. free of other forms), preferably at least about 80% pure, preferably at least about 90% pure, preferably at least about 95% pure, more preferably at least about 99% pure, and most preferably at least about 99.9% pure.

The crystals, powder aggregates and coarse powder of the polymorphic forms of the ST-246 may be optionally milled and sorted by size after undergoing conversion. Milling or grinding refers to physically breaking up the large particles or aggregates of particles using methods and apparatus well known in the art for particle size reduction of powders. Resulting particle sizes may range from millimeters to nanometers, yielding i.e. nanocrystals, microcrystals.

The polymorph of the invention may be milled using known milling procedures such as wet milling to obtain a particle size appropriate for tablet formation and for other formulation types. Finely divided (nanoparticulate) preparations of the polymorph of the invention may be prepared by processes known in the art, for example see international patent application WO 02/00196 (SmithKline Beecham).

In one aspect, the particle size of each of polymorphic Forms I-IV and VI of ST-246 in the present invention has $D_{90}$ of the volume mean diameter of the particles within the range of about 0.01-200 □m, preferably about 15-50 □m, and most preferably about 0.01-15 □m. Such particles are better in chemical and physical stability, good material flow characteristics, improving the uniformity of dosage forms and thus suitable for bulk preparation and formulation advantages.

Formulations and Administration

Formulations of polymorphic forms of ST-246 may be prepared by processes known in pharmaceutics art. The following examples (infra) are given to enable those skilled in the art to more clearly understand and to practice the present invention. They should not be considered as limiting the scope of the invention, but merely as being illustrative and representative thereof.

The polymorphic salts of the present invention can be administered in a variety of oral and parenteral dosage forms. Oral dosage forms can be tablets, coated tablets, hard and soft gelatin capsules, solutions, emulsions, syrups, or suspensions. Parenteral administration includes intravenous, intramuscular, intracutaneous, subcutaneous, intraduodenal, or intraperitoneal administration. Additionally, the salts of the present invention can be administered by transdermal (which may include a penetration enhancement agent), buccal, nasal and suppository routes.

For preparing pharmaceutical compositions from the compounds of the present invention, pharmaceutically acceptable carriers can be either solid or liquid. Solid form preparations include powders, tablets, pills, hard and soft gelatin capsules, cachets, suppositories, and dispersible granules. A solid carrier can be one or more substances which may also act as diluents, flavoring agents, lubricants, suspending agents, binders, preservatives,—tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

Suitable excipients for tablets, coated tablets, and hard gelatin capsules are, for example, microcrystalline cellulose, lactose, corn starch and derivatives thereof, magnesium carbonate, magnesium stearate, sugar, lactose, pectin, dextrin, starch, gelatin, tragacanth, methylcellulose, sodium carboxymethylcellulose, talc, and fatty acids or their salts, e.g., stearic acid. If desired, the tablets or capsules may be enteric-coated or sustained release formulations. Suitable excipients for soft gelatin capsules are, for example, vegetable oils, waxes, fats, semi-solid and liquid polyols. Liquid form preparations include solutions, suspensions, retention enemas, and emulsions. For parenteral injection, liquid preparations can be formulated in solution in water or water/polyethylene glycol solution.

Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Compositions also may contain, in addition to the active component, colorants, flavors, stabilizers, buffers, artificial and natural sweeteners, dispersants, thickeners, preservatives, wetting agents, emulsifiers, salts for adjustment of the osmotic pressure, masking agents, antioxidants and the like.

The compounds of the present invention can be administered intravenously in physiological saline solution (e.g., buffered to a pH of about 7.2 to 7.5). Conventional buffers such as phosphates, bicarbonates or citrates can be used in the present compositions.

Also included are solid form preparations which are intended to be converted, shortly before use, to liquid form preparations for oral administration. Such liquid forms include solutions, suspensions, and emulsions. For preparing suppositories suitable excipients include natural and hardened oils, waxes, fatty acid glycerides, semi-liquid or liquid polyols. The molten homogenous mixture is then poured into convenient sized molds, allowed to cool, and thereby to solidify. Suitable pharmaceutical carriers, excipients and their formulations are described in Remington: The Science and Practice of Pharmacy 1995, edited by E. W. Martin, Mack Publishing Company, 19th edition, Easton, Pa.

The dosage can vary within wide limits and will, of course, be adjusted in each particular case to the individual requirements of the patient and the severity of the condition being treated. A typical preparation will contain from about 5% to about 95% active compound (w/w). For oral administration, a daily dosage of between about 0.01 and about 100 mg/kg body weight per day should be appropriate in monotherapy and/or in combination therapy. A preferred daily dosage is between about 0.1 and about 300 mg/kg body weight, more preferred 1 and about 100 mg/kg body weight and most preferred 1.0 and about 50 mg/kg body weight per day.

Generally, treatment is initiated with smaller dosages which are less than the optimum dose of the compound. Thereafter, the dosage is increased by small increments until the optimum effect under the circumstance is reached. The daily dosage can be administered as a single dosage or in divided dosages, typically between 1 and 5 dosages per day.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Appropriate doses will be readily appreciated by those skilled in the art. It will be appreciated that the amount of a polymorph of the invention required for use in treatment will vary with the nature of the condition being treated and the age and the condition of the patient and will be ultimately at the discretion of the attendant physician or veterinarian. The polymorph of the invention may be used in combination with other antibacterial drugs such as penicillin, cephalosporin, sulfonamide or erythromycin.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the polymorph of the invention or the second therapeutic agent may be administered first. When administration is simultaneous, the combination may be administered either in the same or different pharmaceutical composition.

Using the routes and methods of administration and dosage amounts described hereinabove and the dosage forms described herein below, the individual polymorph forms, such as Form I, Form II, Form III, Form IV, Form V and Form VI, and mixtures of polymorph forms of the present invention can be used for the prevention and treatment of various diseases and conditions in humans. By way of example and not of limitation, in the case of orthopoxvirus infections and associated diseases, this is accomplished by administering to a patient in need of said treatment who is suffering from orthopoxvirus infections a composition containing one of the above polymorph forms, such as Form I, Form II, Form III, Form IV, Form V and Form VI, substantially free of other polymorph forms or mixtures of polymorphs and an inert carrier or diluent, said composition being administered in an effective amount to prevent or treat said viral infection.

In accordance with this invention, ST-246, either as a polymorph form substantially free of other polymorph forms or as a mixture of polymorph forms, is administered in an effective amount to prevent or treat orthopoxviral infection. Any effective amount of such polymorph form substantially free of other polymorph forms or mixtures of polymorph forms needed to prevent or treat such viral infection can be utilized in this composition. In general, in the case oral dosage forms, dosages of from about 0.5 mg/kg to about 5.0 mg/kg of body weight per day are used. However the amount of such polymorph form, such as Form I, Form II, Form III, Form IV, Form V and Form VI, substantially free of other polymorph forms or mixtures of polymorph forms in the oral unit dose to be administered will depend to a large extent on the condition of viral infection, and the weight of the patient and of course be subject to the physician's judgment. In one aspect of the invention, Form I is the preferred ST-246 polymorph form for administration.

In accordance with this invention, the oral unit dosage form containing the given polymorph form substantially free of other polymorph forms or mixtures of polymorph forms can be preferably administered at a dosage of from about 30 mg to 800 mg per day, more preferably from about 50 mg to about 600 mg per day, administered once to three times during the day or as needed.

In some aspect of the invention, the polymorph of the present invention, preferably hydrate form of ST-246, may also be used in combination with: (1) a vaccine; (2) Cidofovir, an injectable antiviral medication which is acyclic nucleoside phosphonate, and is therefore independent of phosphorylation by viral enzymes, to treat eczema vaccinatum (EV), a life-threatening complication of vaccinia virus infection, and other related disorders; and/or (3) CMX001 (hexadecyloxypropyl-cidofovir), a mimic of a naturally occurring lipid, lysolecithin, formed by linking a lipid, 3-hexadecyloxy-1-propanol, to the phosphonate group of cidofovir.

The invention also provides pharmaceutical packs or kits comprising one or more containers filled with one or more crystalline polymorph of ST-246, including Form I, Form II, Form III, Form IV, Form V and Form VI. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain aspect of the invention, the kit contains more than one crystalline polymorph of ST-246.

Example 1—Preparation of Polymorphic Form I

More specifically, to prepare ST-246 monohydrate, Form I, cycloheptatriene is reacted with maleic anhydride in the presence of toluene to yield the major product, endo isomer. The exo isomer is further produced from about 7% to 0.6% by crystallization from toluene/heptane. Further, hydrazine in the anhydrous or hydrate form is reacted with Methyl 4-(trifluoromethyl) benzoate in the presence of isopropanol to yield (4-(trifluoromethyl)-benzhydrazide. The product is then crystallized from isopropanol.

The next step of the synthesis involves condensing endo-tricyclo[3.2.2.0]non-8-endo-6,7-dicarboxylic anhydride and (4-(trifluoromethyl)-benzhydrazide) in isopropanol. The product is isolated by crystallization from isopropanol and the slurry is further heated to reflux and held. The resulting solution is cooled and sampled for reaction completion. After analysis shows reaction completion, carbon and celite are charged and the batch is heated to reflux and held. After cooling, the batch is filtered to remove these solid materials, followed by a filter chase with IPA. The batch is cooled and held while slurry is formed. The batch is further cooled and held. Contents are centrifuged and the wet cake containing synthesis product is washed with heptane. The wet cake is dried and is referred to as partially hydrated form of ST-246 (SG3).

The SG3 is charged followed by ethyl acetate. The mixture is heated and held to ensure dissolution of SG3. A polish filtration is performed on the batch and an extraneous material check confirms that the filtration was successful. Ethyl acetate is used to charge the filter. After heating the batch to reflux, Endotoxin reduced (ER) water is charged. The batch is seeded and the final ER water is charged. The batch is held at reflux and a slurry check is performed.

Further, the batch is cooled, at which time a sample of the slurry is obtained for verification of correct polymorph. The batch is cooled further and is held until final isolation on the centrifuge. The final API is dried, milled using a Fitz Mill as described in WO 02/00196. Form I can be prepared by crystallization of ST-246 from a variety of solvents and solvent combinations as further summarized in Tables 2 and 3:

TABLE 3

Solvent screening study results.

| Solvent A | Solvent B | Ratio (volA:volB) | Saturation Temp (° C.) | Overheat Temp (° C.) | Growth Temp (° C.) | Crystal Form |
|---|---|---|---|---|---|---|
| 1-Propanol | None | | 30 | 35 | 25 | II |
| Ethanol | Water | 1:1 | 40 | 45 | 35 | II |
| Acetone | IPA | 4:1, 1:1, 1:4 | 40 | 45 | 35 | II |
| ACN | Ethyl acetate | 1:1 | 40 | 45 | 35 | II |
| Ethanol | Toluene | 4:1 | 40 | 45 | 35 | II |
| Ethanol | Water | 1:1 | 50 | 55 | 50 | II |
| Acetone | IPA | 4:1, 1:1, 1:4 | 50 | 55 | 50 | II |
| ACN | Ethyl acetate | 4:1, 1:1 | 50 | 55 | 50 | II |
| Methanol | CHCl3 | 1:4 | 50 | 55 | 50 | II |
| Ethanol | Toluene | 4:1, 1:1, 1:4 | 50 | 55 | 50 | II |
| Ethanol | Water | 1:1 | 30 | 35 | 30 | II |
| Acetone | IPA | 4:1, 1:1, 1:4 | 30 | 35 | 30 | II |
| Water | Ethyl acetate | 1:1 | 30 | 35 | 30 | II |
| DMF | ACN | 4:1 | 30 | 35 | 30 | II |
| Ethanol | Toluene | 4:1 | 30 | 35 | 30 | II |
| Ethyl acetate | None | 1 gram scale | | | | II |
| IPA | None | | 30 | 35 | 25 | III |
| DMF | None | | 30 | 35 | 25 | III |
| DMA | None | | 30 | 35 | 25 | III |
| Pyridine | None | | 30 | 35 | 25 | III |
| Isopropyl ether | None | | 30 | 35 | 25 | III |

TABLE 3-continued

Solvent screening study results.

| Solvent A | Solvent B | Ratio (volA:volB) | Saturation Temp (° C.) | Overheat Temp (° C.) | Growth Temp (° C.) | Crystal Form |
|---|---|---|---|---|---|---|
| THF | None | | 30 | 35 | 25 | III |
| CH2Cl2 | IPA | 4:1, 1:1, 1:4 | 40 | 45 | 35 | III |
| Ethanol | Water | 4:1, 1:4 | 40 | 45 | 35 | III |
| ACN | Ethyl acetate | 4:1 | 40 | 45 | 35 | III |
| TFE | THF | 4:1, 1:1, 1:4 | 40 | 45 | 35 | III |
| DMF | ACN | 4:1, 1:1 | 40 | 45 | 35 | III |
| Methanol | CHCl3 | 4:1, 1:1 | 40 | 45 | 35 | III |
| Ethanol | Toluene | 1:1 | 40 | 45 | 35 | III |
| CH2Cl2 | IPA | 4:1, 1:1, 1:4 | 50 | 55 | 50 | III |
| Ethanol | Water | 4:01 | 50 | 55 | 50 | III |
| ACN | Ethyl acetate | 1:4 | 50 | 55 | 50 | III |
| TFE | THF | 4:1, 1:1 | 50 | 55 | 50 | III |
| DMF | ACN | 4:1, 1:1, 1:4 | 50 | 55 | 50 | III |
| Methanol | CHCl3 | 4:1, 1:1 | 50 | 55 | 50 | III |
| Water | IPA | 1:1, 1:4 | 30 | 35 | 30 | III |
| Ethanol | Water | 4:1 | 30 | 35 | 30 | III |
| Water | Ethyl acetate | 4:1 | 30 | 35 | 30 | III |
| Trifluoroethanol (TFE) | THF | 4:1 | 30 | 35 | 30 | III |
| DMF | ACN | 1:1, 1:4 | 30 | 35 | 30 | III |
| Methanol | CHCl3 | 4:1, 1:1, 1:4 | 30 | 35 | 30 | III |
| Ethanol | Toluene | 1:1, 1:4 | 30 | 35 | 30 | III |
| Trifluoroethanol (TFE) | None | | 30 | 35 | 25 | IV |
| 1 Butanol | None | | 30 | 35 | 25 | IV |
| CH2Cl2 | None | | 30 | 35 | 25 | IV |
| CHCl3 | None | | 30 | 35 | 25 | IV |
| Toluene | None | | 30 | 35 | 25 | IV |
| ACN | Ethyl acetate | 1:4 | 40 | 45 | 35 | IV |
| Ethanol | Toluene | 1:4 | 40 | 45 | 35 | IV |
| Water | Ethyl acetate | 1:4 | 30 | 35 | 30 | IV |
| Trifluoroethanol (TFE) | THF | 1:1 | 30 | 35 | 30 | IV |
| 1 Butanol | None | 1 gram scale | | | | IV |
| Methanol | None | | 30 | 35 | 25 | V |
| Ethanol | None | | 30 | 35 | 25 | V |
| 2 Butanol | None | | 30 | 35 | 25 | V |
| Acetone | None | | 30 | 35 | 25 | V |
| Methyl Ethyl Ketone | None | | 30 | 35 | 25 | V |
| Ethyl acetate | None | | 30 | 35 | 25 | V |
| MTBE | None | | 30 | 35 | 25 | V |
| Isopropyl acetate | None | | 30 | 35 | 25 | V |
| Acetonitrile (can) | None | | 30 | 35 | 25 | V |
| DMF | ACN | 1:4 | 40 | 45 | 35 | V |
| Nitromethane | None | | 30 | 35 | 25 | VI |
| Nitromethane | None | 1 gram scale | | | | VI |
| Methanol | CHCl3 | 1:4 | 40 | 45 | 35 | VI |

Figure 7:
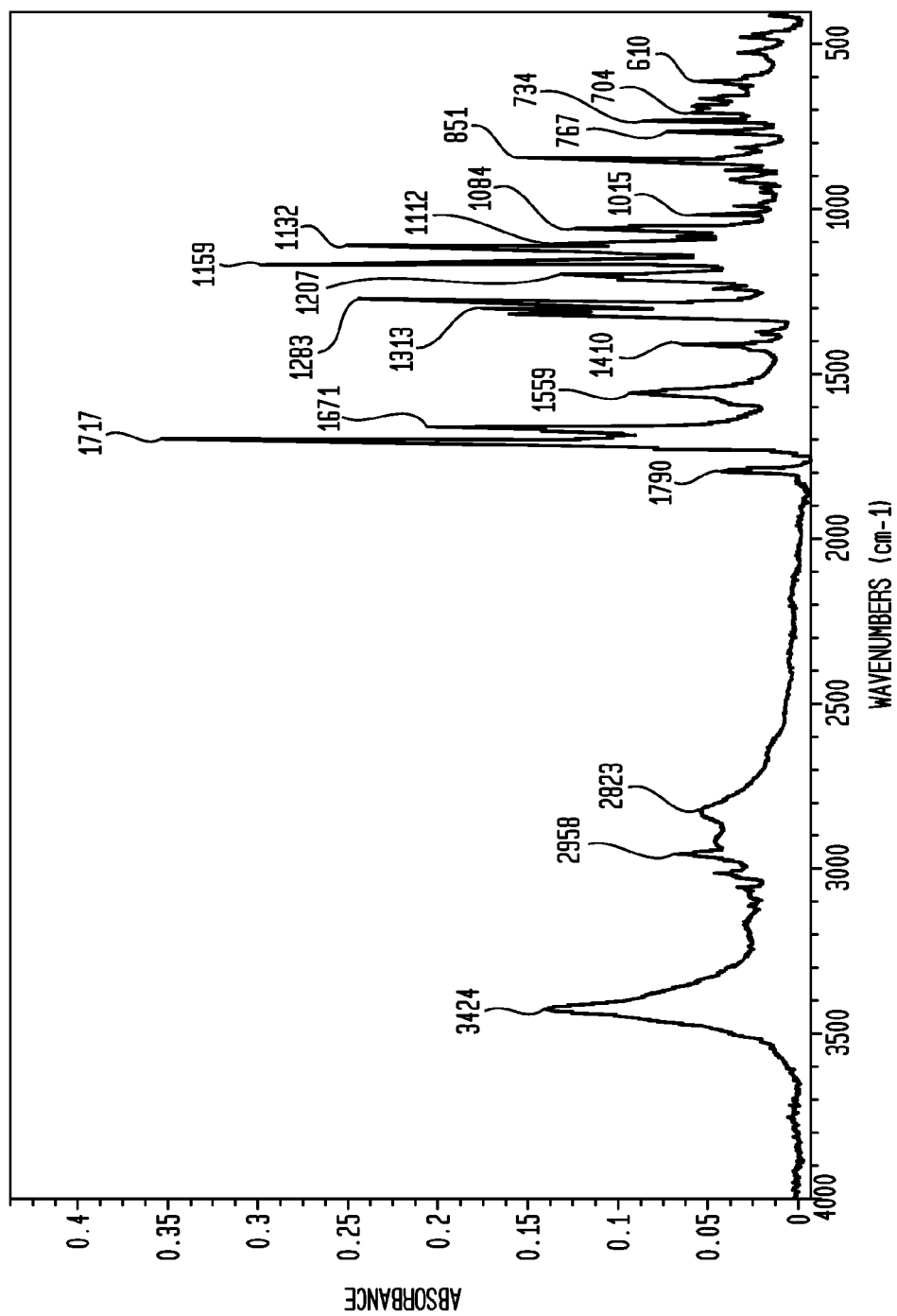
FIG. 7 depicts Fourier transform infra red (FTIR) spectrum of Form I.

The identity of ST-246 Form I obtained by the above described process was confirmed by XRPD and IR as summarized in FIGS. 1 and 7.

Example 2—Preparation of Polymorphic Form II

Standards of Form II were made by re-crystallization of Forms I and V starting material from ethyl acetate and chloroform solvents. An amount of ST-246 Form I or Form V was dissolved in either ethyl acetate or chloroform and filtered through 0.45 □m membrane filters. The filtered solutions were overheated at a higher temperature to make sure all solids were dissolved and then reduced to a lower temperature and evaporated to dryness under a nitrogen purge (~2 psi.).

The preferred crystallization conditions for Form II are summarized in Table 4 below:

TABLE 4

Crystallization conditions for ST-246 Form II.

| Starting Material | Solvent | Overheating Temperature (° C.) | Evaporation Temperature (° C.) | XRPD Pattern |
|---|---|---|---|---|
| 1.5 g | Ethyl acetate | 35 | 25 | Form II |
| 1.1 g | Chloroform | 45 | 35 | Form II |

The further examples of crystallization conditions for Form II are also summarized in Tables 1-2 above.

Figure 2:
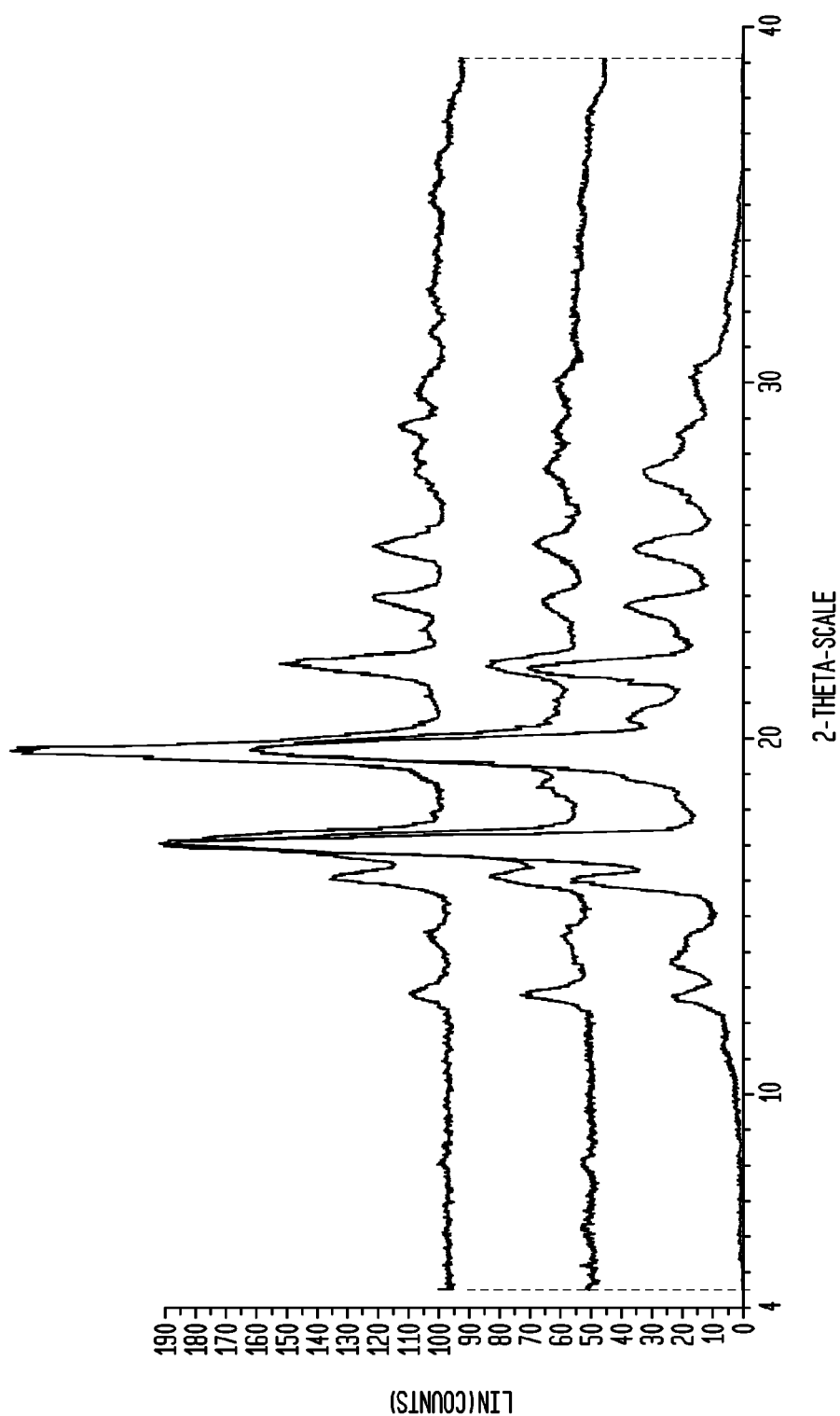
FIG. 2 shows three X-ray powder diffraction (XRPD) patterns of Form II (from three different samples).

The identity of ST-246 Form II obtained by the above described process was confirmed by XRPD as summarized in FIG. 2.

Example 3—Preparation of Polymorphic Form III

Form III is produced from reslurry of anhydrous ST-246 in water. Further examples of solvents used to generate Form III are summarized in Tables 1-9 above.

Figure 8:
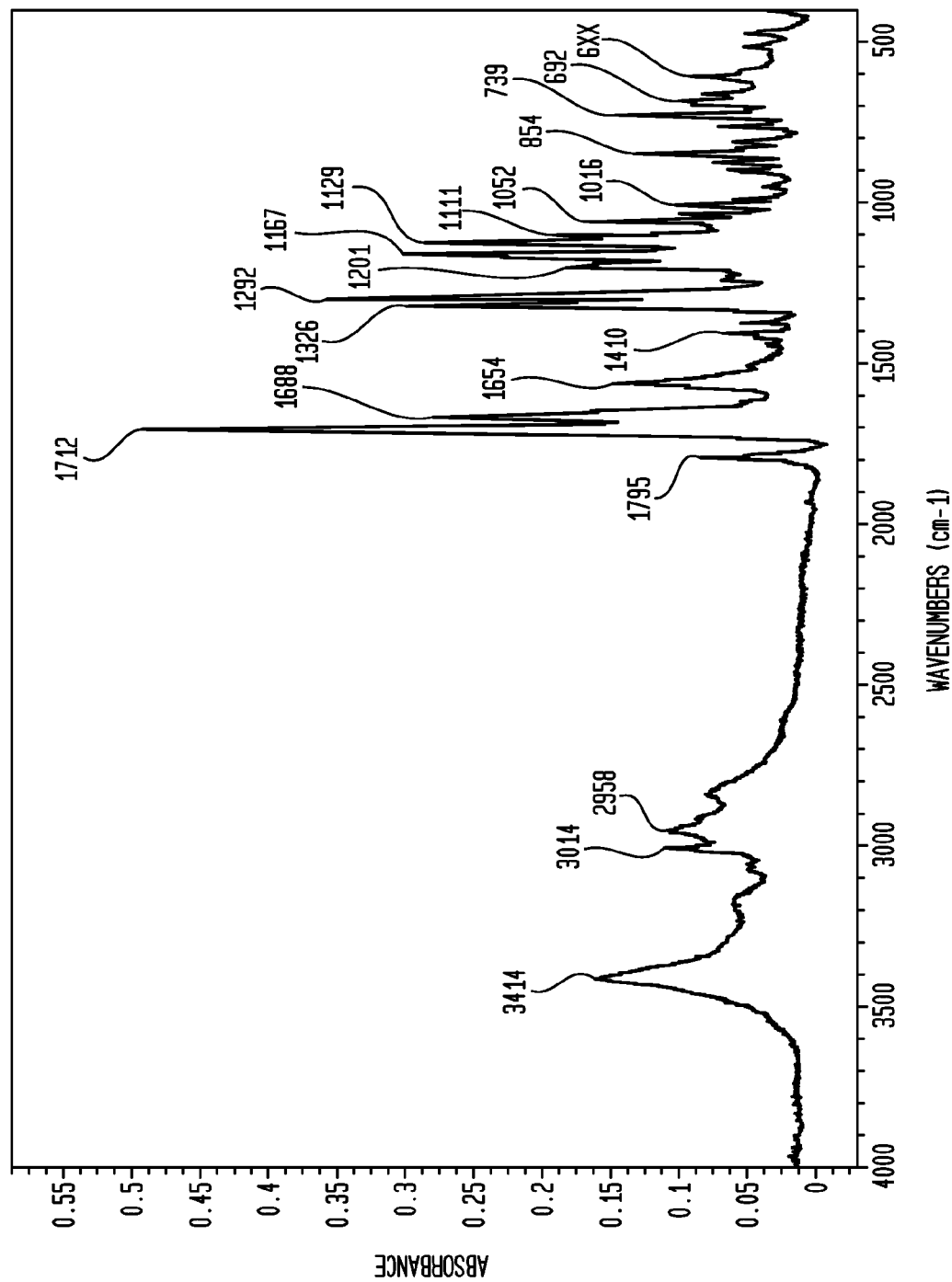
FIG. 8 depicts Fourier transform infra red (FTIR) spectrum of Form III.

The identity of ST-246 Form III produced by the process described above was confirmed by XRPD and IR as summarized in FIGS. 3 and 8.

Example 4—Preparation of Polymorphic Form IV

A standard of Form IV was made by re-crystallization of Form I starting material from 1-butanol solvent. The starting solid material was dissolved in 1-butanol and filtered through a 0.45 um membrane filter. The filtered solution was overheated at a higher temperature to make sure all solids were dissolved and then reduced to a lower temperature and evaporated to dryness under a nitrogen purge (~2 psi). The preferred crystallization conditions for Form IV are summarized in Table 5. Further examples of crystallization of Form IV are summarized in Tables 1-3.

TABLE 5

Crystallization conditions for ST-246 Form IV.

| Starting Material | Solvent | Overheating Temperature (° C.) | Evaporation Temperature (° C.) | XRPD Pattern |
|---|---|---|---|---|
| 1.5 g | 1-butanol 70 ml | 50 | 35 | Form IV |

The identity of ST-246 Form IV produced by the process described above was confirmed by XRPD as summarized in FIG. 4.

Example 5—Preparation of Polymorphic Form V

Form V (hemi-hydrate) was made during early GMP syntheses of ST-246 and is disclosed in WO 2008/079159 and WO 2008/130348. The disadvantage of this polymorph is that it is not fully hydrated. This form readily absorbs moisture when placed in a humid environment, and has been shown to convert to Form I in competitive slurry experiments The identity of ST-246 Form V was confirmed by XRPD and IR as summarized in FIGS. 5 and 9.

Example 6—Preparation of Polymorphic Form VI

A standard of Form VI was made by re-crystallization of Form V starting material from nitromethane solvent. The starting solid material was dissolved in nitromethane and filtered through a 0.45 um membrane filter. The filtered solution was overheated at a higher temperature to make sure all solids were dissolved and then reduced to a lower temperature and evaporated to dryness under a nitrogen purge (~2 psi). Form VI can be prepared by crystallization of ST-246 from a variety of solvents and solvent combinations. The preferred crystallization conditions are summarized in Table 6 below. Further examples of crystallization of Form VI are summarized in Tables 1-3.

TABLE 6

Form VI Crystallization Conditions.

| Starting Material | Solvent | Overheating Temperature (° C.) | Evaporation Temperature (° C.) | XRPD Pattern |
|---|---|---|---|---|
| 1.2 g | Nitromethane (60 ml) | 35 | 25 then 35 | Form VI |

The identity of ST-246 Form VI obtained by a process described above was confirmed by XRPD as summarized in FIG. 6.

Example 7—Distinguishing and Comparative Physical Characteristic of Polymorphic Forms of ST-246, Form I, Form III and Form V It has been determined that ST-246 can exist in three predominant physical forms (Forms I, III and V). The data was obtained on the relevant physical/chemical properties and stability of the polymorphs to determine if the different solid forms impact the quality of the product. These data include the crystallographic properties of the polymorphs and physical/chemical properties of the polymorphs (e.g. solubility, dissolution, melting range) accelerated stability data.

Figure 5:
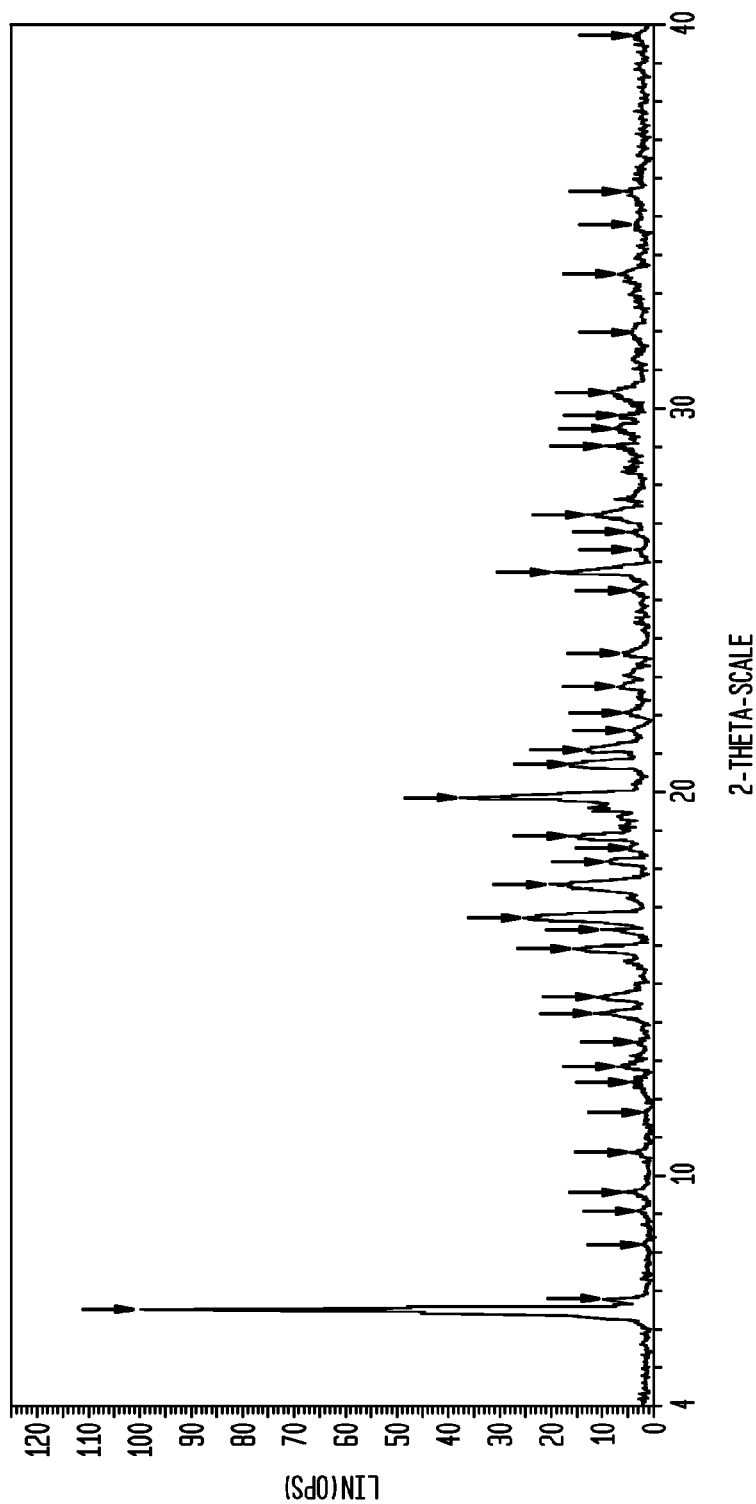
FIG. 5 shows an X-ray powder diffraction (XRPD) pattern of Form V.

The X-ray diffractions patterns of Forms I, III and V are shown in FIGS. 1, 3 and 5, respectively. The powder X-ray pattern of Forms I, III, and V are readily distinguishable based on the unique features in their powder patterns.

Interconversion of Forms I, III and V

Competitive and non-competitive slurry experiments were performed to determine the most stable form of ST-246. The slurry experiments were performed by exposing excess material of one or more forms of ST-246 in a small volume of water and agitating the resulting suspensions for several days at ambient temperature and/or 45° C. Similar experiments were also done at different pH values for 60 minutes at 37° C. The slurry was filtered and the solid analyzed by powder XRPD. To avoid possible desolvation or physical change after isolation, the samples were not subjected to drying before powder X-ray analysis. Competitive and non-competitive slurry experiments in water show that Form V and Form III convert to Form I in water and Form I remains unchanged. The slurry data are summarized in Table 7 below:

TABLE 7

Interconversion of Polymorphs of ST-246 in Aqueous Liquids.

| Initial Forms | Solvent/Temp | Slurry Duration | Final Form |
|---|---|---|---|
| I, III & V | Water/RT | 5 days | I |
| I, III & V | Water/RT | 13 days | I |
| I & III | Water/RT | 2 days | I |
| I & III | Water/RT | 30 days | I |
| V | pH 1.2, 6.8/37° C. | 30 min | III |
| III | Water/45° C. | 17 days | I |
| I | Water/45° C. | 17 days | I |

Micronization of Form I and III:

ST-246 belongs to BCS class II due to its poor solubility in physiologically relevant buffers. Phase 1 clinical trial material was made using micronized Form V with particle size of d50% 4.8 μm and d90% 12 μm. Hence both Forms I and III at a scale of 400 μm were micronized using an airjet mill as described in WO 02/00196. On milling, both the forms yielded the desired particle size without undergoing any transformation in physical form (based on XRPD).

Figure 14:
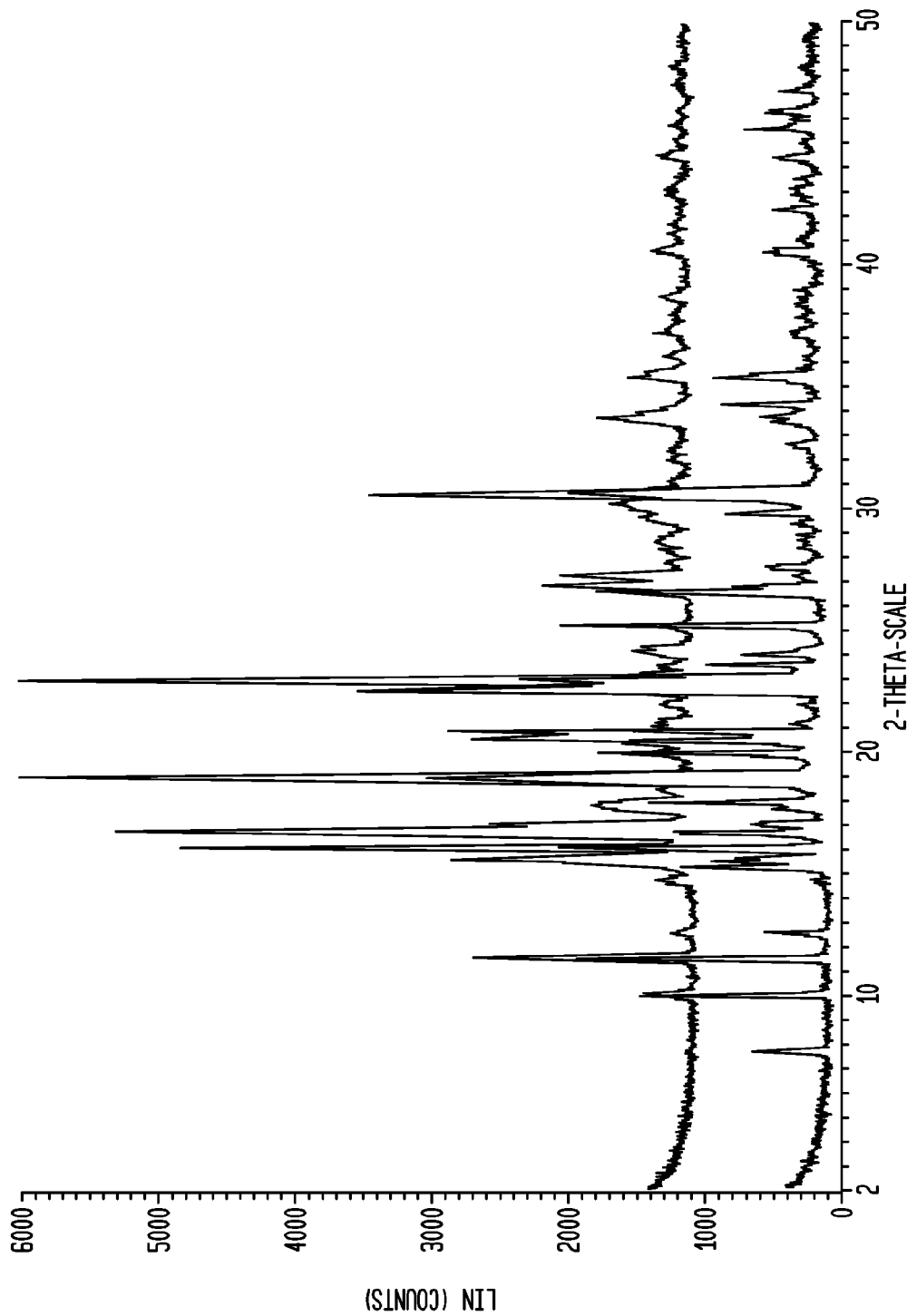
FIG. 14 depicts XRPD Pattern of Micronized (upper pattern) and unmicronized (lower pattern) Form I.
Figure 15:
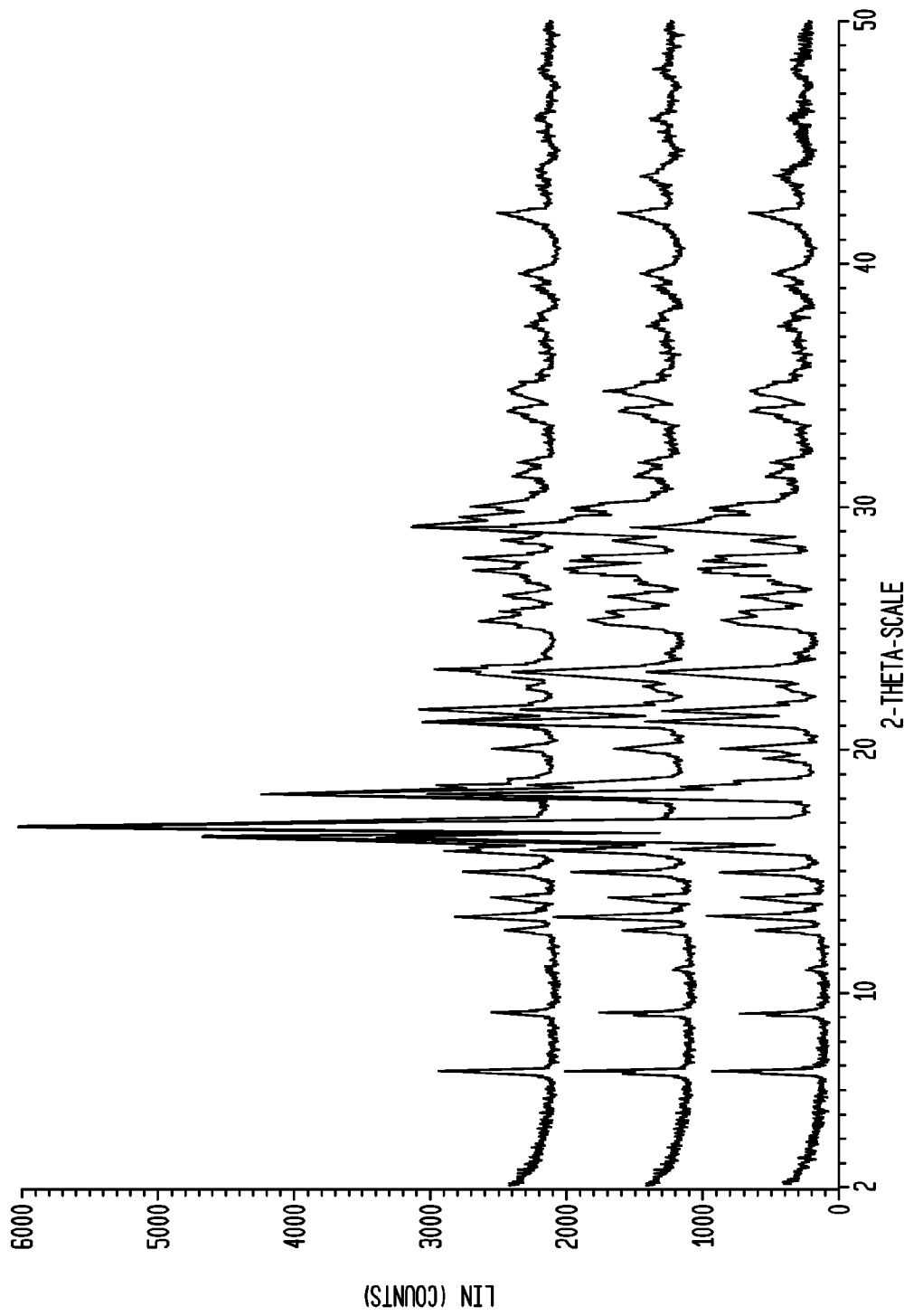
FIG. 15 depicts XRPD Pattern of micronized (top pattern) and unmicronized (middle and lower patterns from 2 different samples) Form III.
Figure 16:
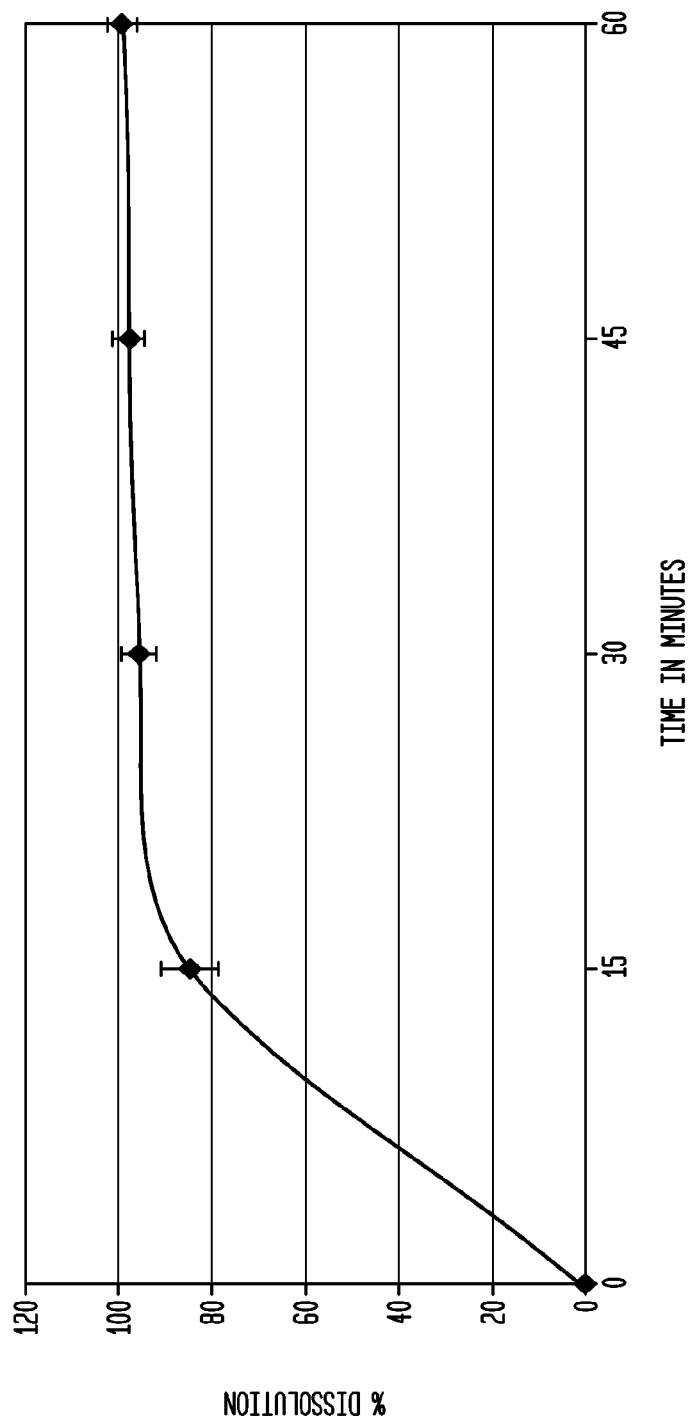
FIG. 16 depicts effect of particle size on dissolution of 200 mg ST-246 Form I capsules with 3% HDTMA wherein the dissolution conditions are 900 ml, 0.05M Phosphate buffer, pH 7.5, USP 2 at 75 RPM, 37° C. and the capsule is made from Form I APIs with particle size D90 of about 5.5 microns.
Figure 17:
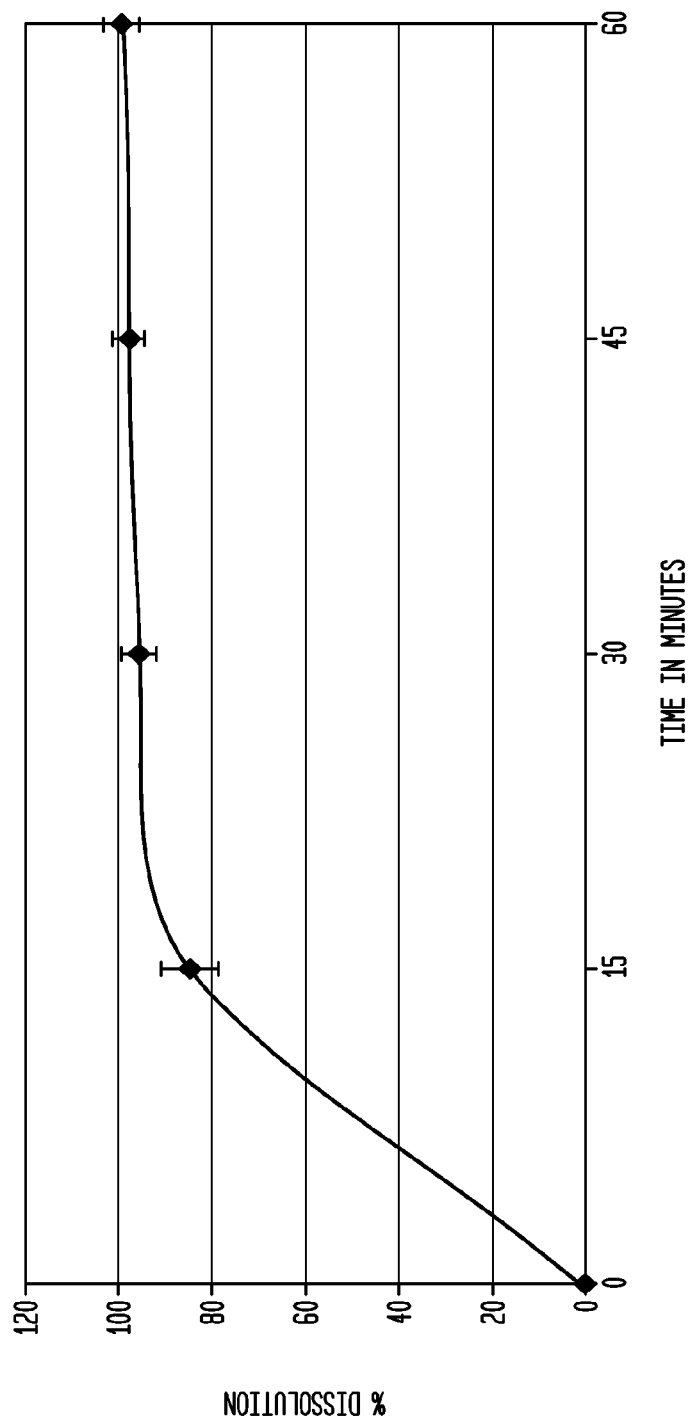
FIG. 17 depicts effect of particle size on dissolution of 200 mg ST-246 Form I capsules with 3% HDTMA wherein the dissolution conditions are 900 ml, 0.05M Phosphate buffer, pH 7.5, USP 2 at 75 RPM, 37° C. and the capsule is made from Form I APIs with particle size D90 of about 16.73 microns.
Figure 18:
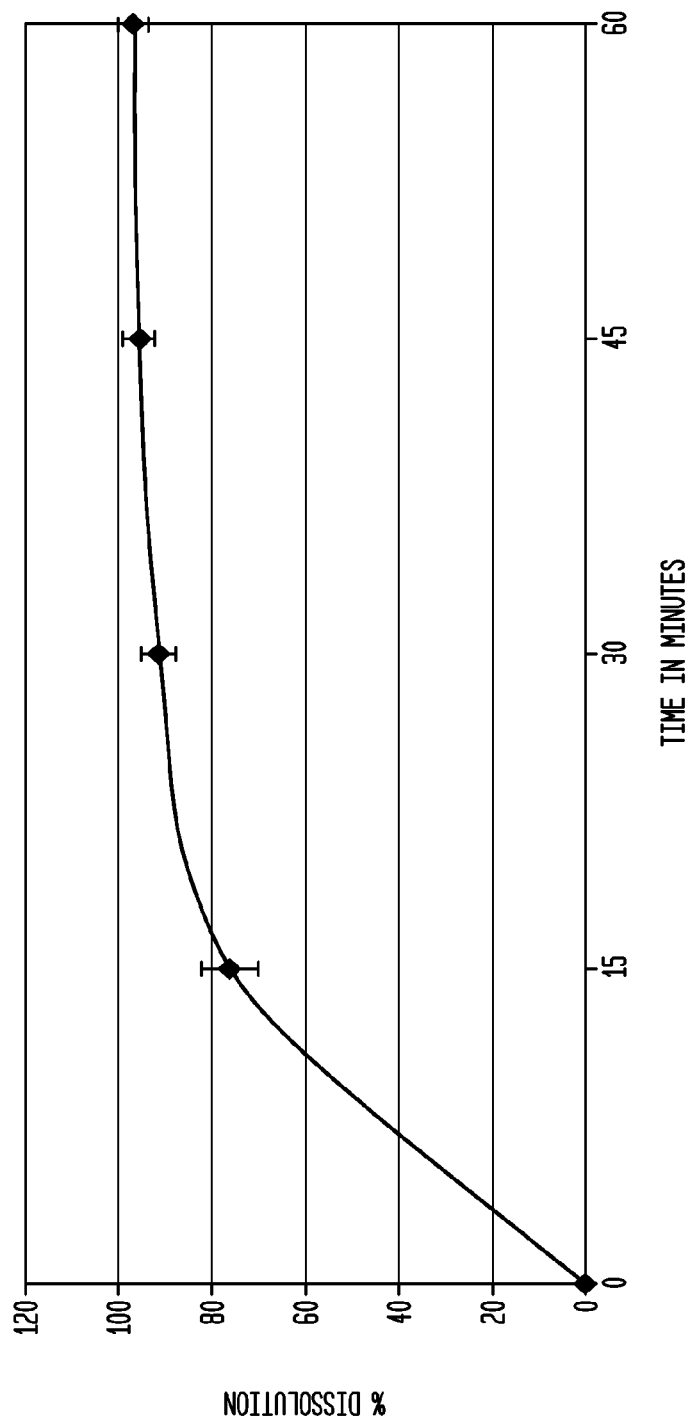
FIG. 18 depicts effect of particle size on dissolution of 200 mg ST-246 Form I capsules with 3% HDTMA wherein the dissolution conditions are 900 ml, 0.05M Phosphate buffer, pH 7.5, USP 2 at 75 RPM, 37° C. and the capsule is made from Form I APIs with particle size D90 of about 26.55 microns.
Figure 19:
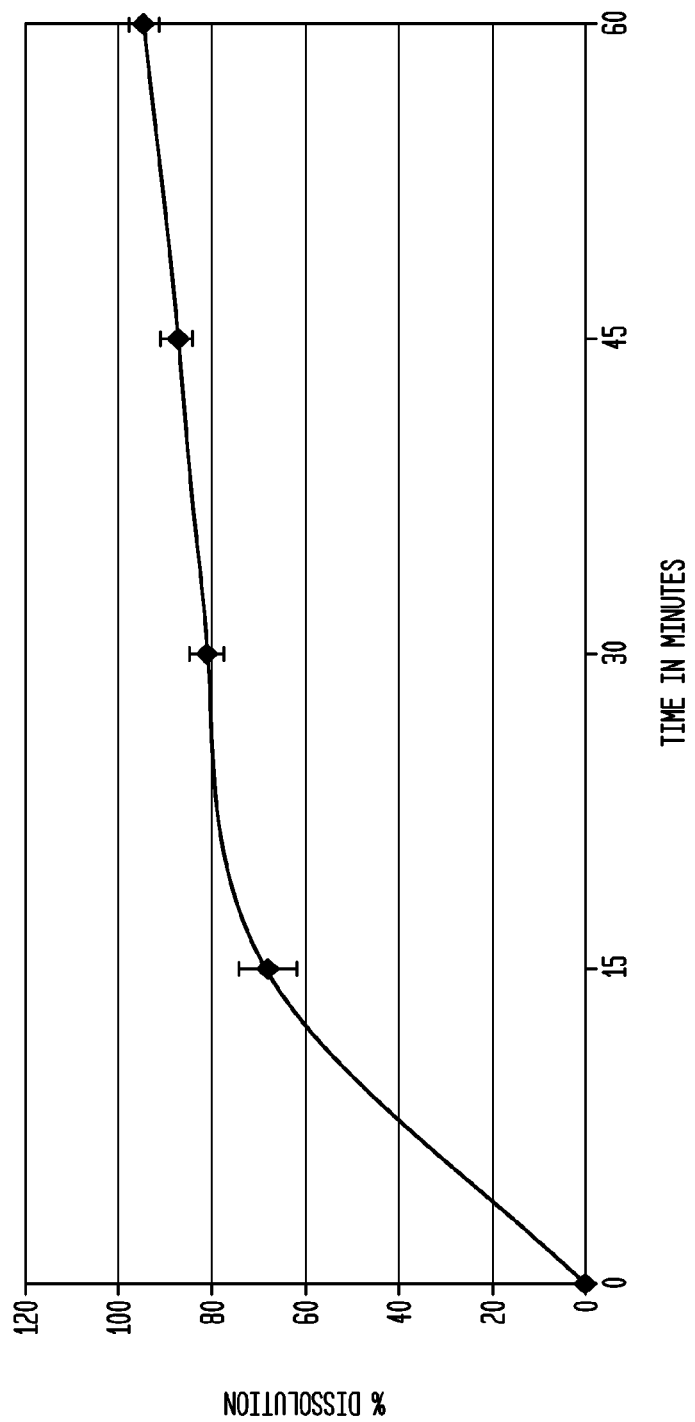
FIG. 19 depicts effect of particle size on dissolution of 200 mg ST-246 Form I capsules with 3% HDTMA wherein the dissolution conditions are 900 ml, 0.05M Phosphate buffer, pH 7.5, USP 2 at 75 RPM, 37° C. and the capsule is made from Form I APIs with particle size D90 is about 75 microns.
Figure 20:
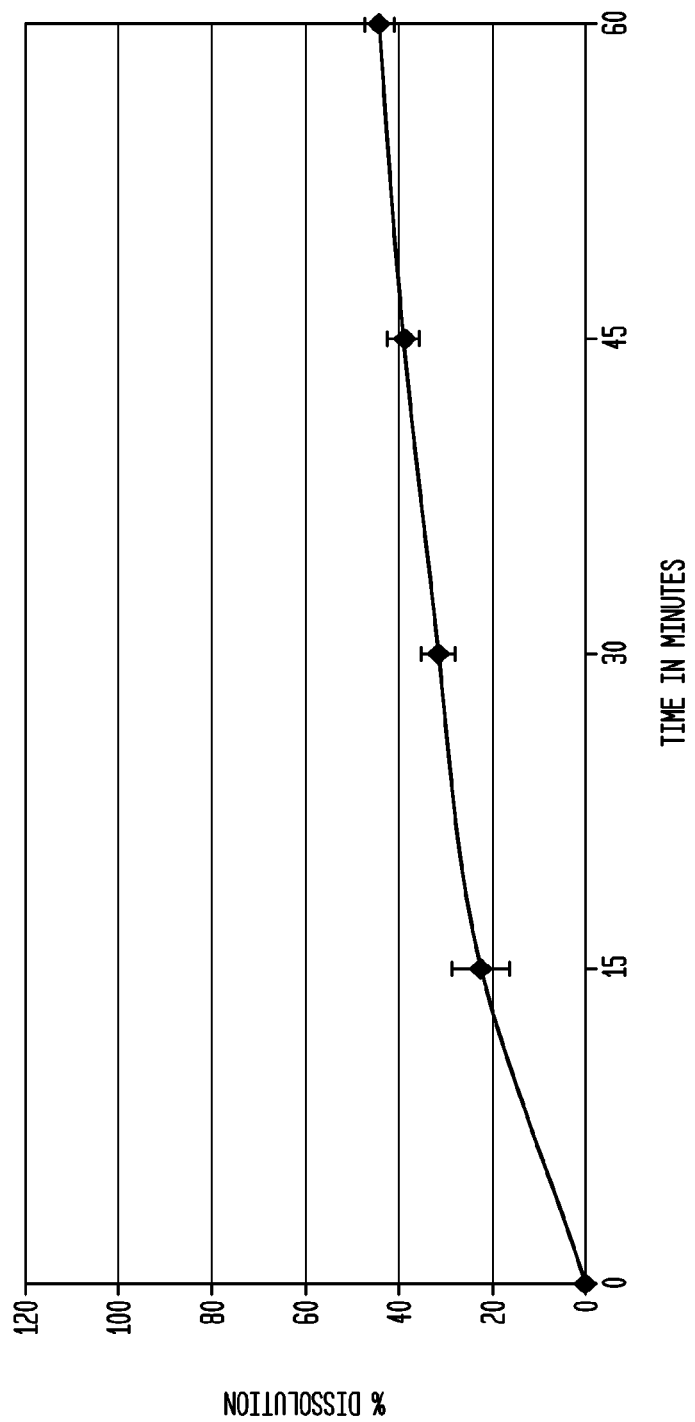
FIG. 20 depicts effect of particle size on dissolution of 200 mg ST-246 Form I capsules with 3% HDTMA wherein the dissolution conditions are 900 ml, 0.05M Phosphate buffer, pH 7.5, USP 2 at 75 RPM, 37° C. and the capsule is made from Form I APIs with particle size D90 of about 254 microns.
Figure 21:
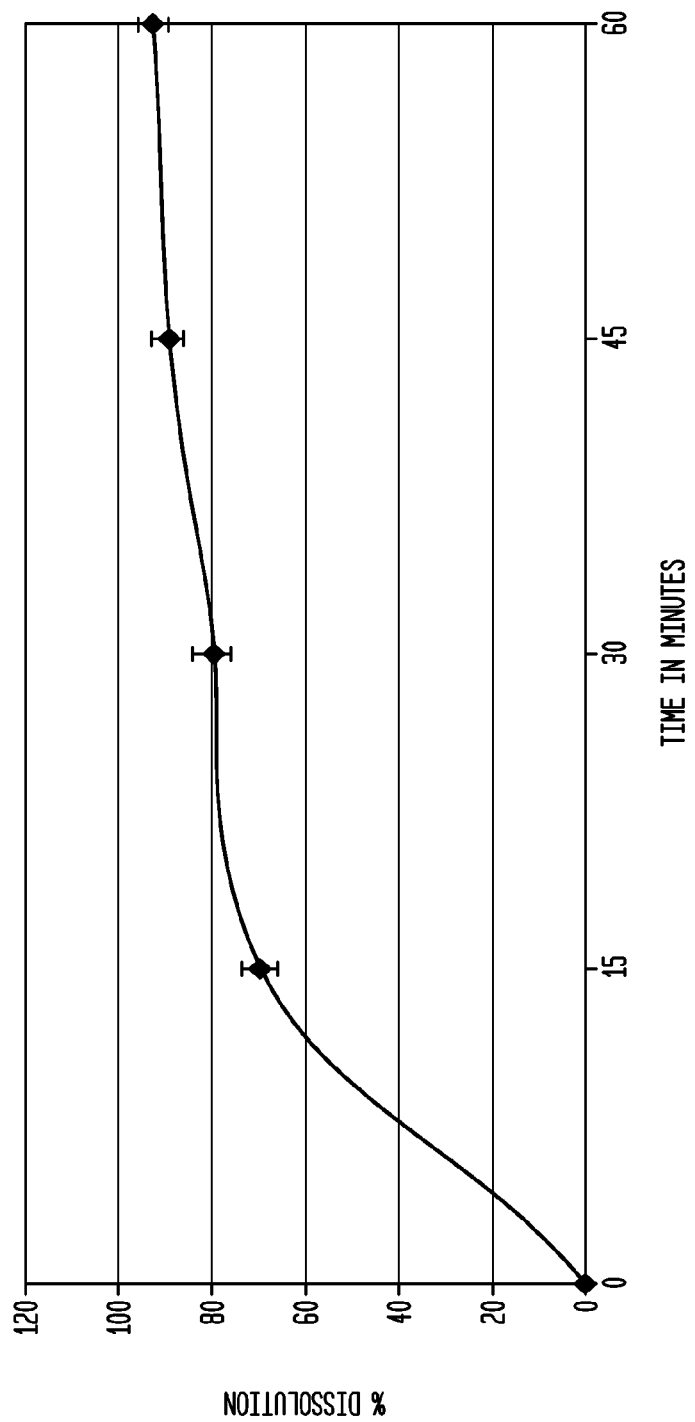
FIG. 21 depicts dissolution profile of Form I.
Figure 22:
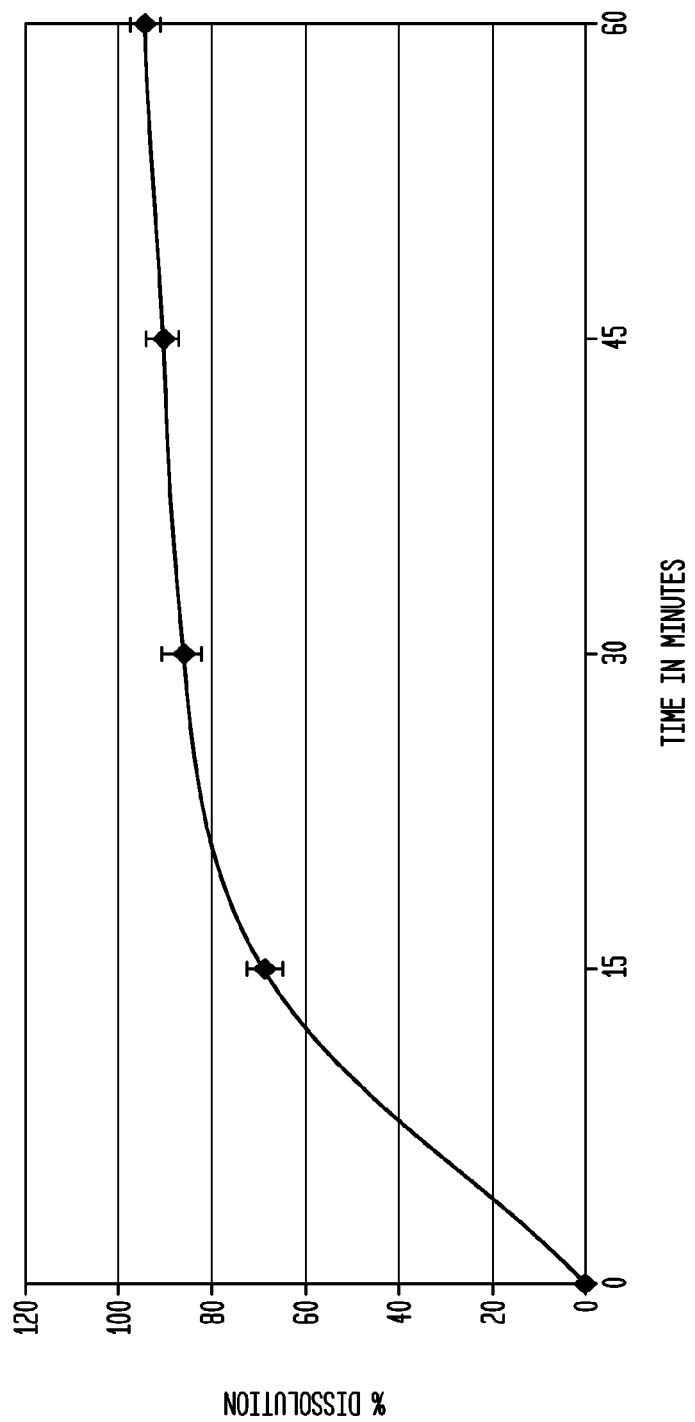
FIG. 22 depicts dissolution profile of Form III.
Figure 23:
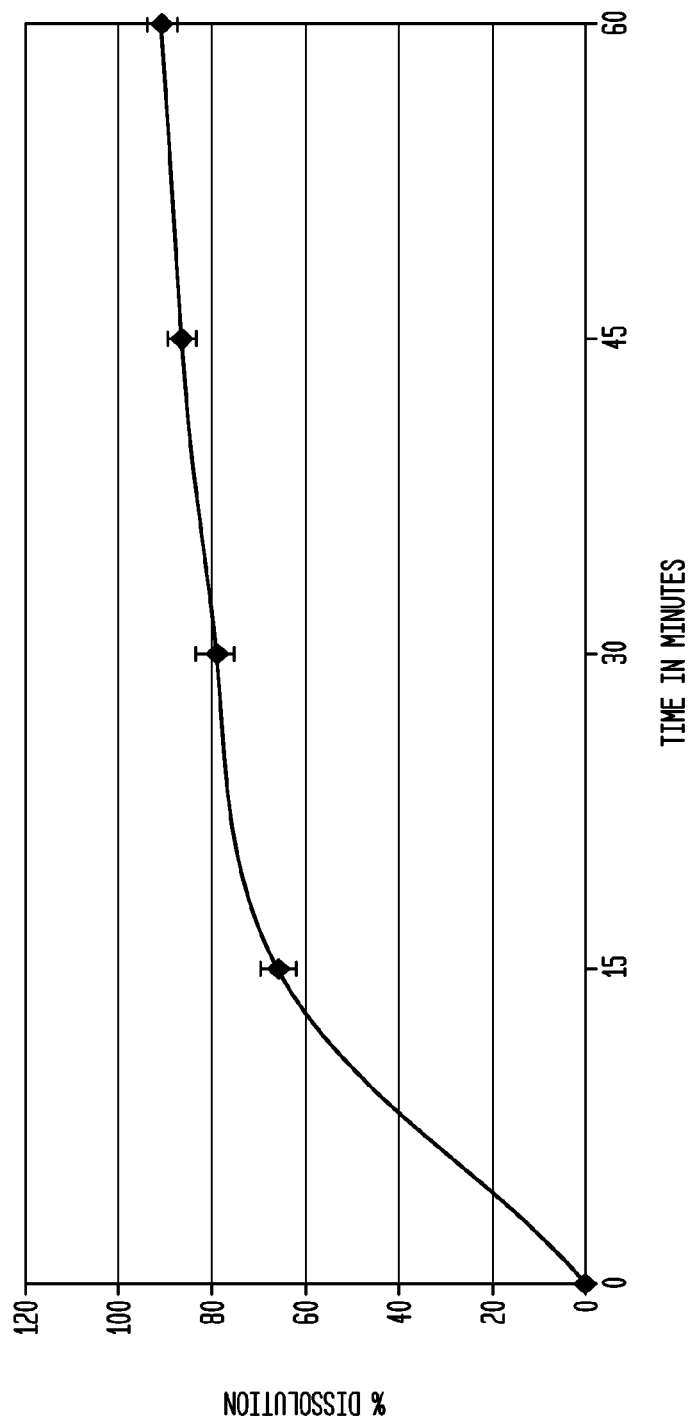
FIG. 23 depicts dissolution profile of Form V.

Representative XRPD patterns of both micronized and unmicronized Forms I and III are summarized in FIGS. 14 and 15.

Drug Substance Stability

Drug substance Forms I and III, both micronized and unmicronized, have undergone short-term stability evaluation under stress conditions. The short-term study has been completed and the data obtained at 40° C./75% RH are presented in Tables 8 and 9.

TABLE 8

Three months R&D stability data of ST-246 Forms I and III.

| | 40° C./75% RH Open | | | |
|---|---|---|---|---|
| Test | Initial | 1 Month | 2 Month | 3 Month |
| Batch #14KM46B (Form I) | | | | |
| Assay (HPLC) | 97.38% | Not Done | Not Done | 98.53% |
| Related Substances | 0.06% isomer, <0.05% unknown RRT = 1.4 | Not Done | Not Done | 0.07% isomer, <0.05% unknown RRT = 1.4 |
| Moisture (by KF) | 4.7% | 5.1% | 5.0% | 5.2% |
| XRD | Form I | Form I | Form I | Form I |
| Melting Point (by DSC) | 197.15° C. | 196.39° C. | 196.21° C. | Not done |
| Batch #14KM49B (Form III) | | | | |
| Assay (HPLC) | 100.64% | Not Done | Not Done | 99.95% |
| Related Substances | 0.02% isomer, <0.05% unknown RRT = 1.4 | Not Done | Not Done | 0.03% isomer, <0.05% unknown RRT = 1.4 |
| Moisture (by KF) | 4.5% | 5.2% | 5.1% | 4.9% |
| XRD | Form III | Form III | Form III | Form III |
| Melting Point (by DSC) | 196.92° C. | 195.85° C. | 196.24° C. | Not done |

TABLE 9

R&D Stability Data of ST-246 Forms I and III (Micronized lot).

| | | 25° C./60% RH | | 40° C./75% RH | |
|---|---|---|---|---|---|
| Test | T = 0 | 1 Month | 2 Month | 1 Month | 2 Month |
| Lot # 14KM75B-4724 (Form I) | | | | | |
| Assay (HPLC) % | 97.36 | 101.15 | 99.68 | 102.33 | 99.71 |
| Related Substances (%) | | | | | |
| RRT 1.08 | 0.11 | 0.07 | <0.05 | 0.06 | 0.08 |
| RRT 1.37 | <0.05 | <0.05 | <0.05 | <0.05 | <0.05 |
| RRT 1.39 | <0.05 | <0.05 | <0.05 | <0.05 | <0.05 |
| Moisture (by TGA) % | 4.8 | 4.7 | 5.09 | 4.7 | 5.26 |
| XRD | Form I | Form I | Form I | Form I | Form I |
| Melting Point (by DSC) | 196.33° C. | Not Done | 196.03° C. | Not Done | 196.06° C. |
| Lot # 14KM84-4724 (Form III) | | | | | |
| Assay (HPLC) % | 97.87 | 101.6 | 99.48 | 102.1 | 99.38 |
| Related Substances (%) | | | | | |
| RRT 1.08 | 0.07 | 0.10 | <0.05 | 0.07 | 0.05 |
| RRT 1.37 | <0.05 | <0.05 | <0.05 | <0.71 | <0.05 |
| RRT 1.39 | <0.05 | <0.05 | <0.05 | <0.09 | <0.05 |
| Moisture (by TGA) % | 4.8 | 4.7 | 4.78 | 5.2 | 5.32 |
| XRD | Form III | Form III | Form III | Form III | Form III |
| Melting Point (by DSC) | 194.44° C. | Not Done | Not Done | Not Done | Not Done |

The data on both micronized and unmicronized drug substance indicates no change in physical form of both I and III with respect to Purity, Related Substances, Moisture, XRPD and DSC.

The long-term study has also been completed and the data obtained are presented in Table 10.

TABLE 10

Long-Term Stability Testing Results - Lot # SG-08B01-M (Form-I).

| Interval month | Description | Water Content | HPLC Assay | HPLC Related Substances RRt ~1.08 | HPLC Related Substances Total | SG1 & SG1 Exo Isomer | Hydrazine By HPLC | SG2 Dimer |
|---|---|---|---|---|---|---|---|---|
| 0 | conforms | 4.40% | 99.7% | 0.06% | 0.06% | na | na | na |
| 3 | conforms | 4.66% | 99.7% | 0.06% | 0.06% | na | na | na |
| 6 | conforms | 4.71% | 99.7% | <0.05% | <0.05% | na | na | na |
| 9 | conforms | 4.47% | 97.4% | <0.05% | <0.05% | na | na | na |
| 12 | conforms | 4.67% | 98.5% | 0.05% | 0.05% | na | na | na |
| 18 | conforms | 4.79% | 99.8% | 0.05% | 0.05% | na | na | na |
| 24 | conforms | 4.81% | 100.2% | 0.05% | 0.05% | <0.05% | <0.1 ppm | <0.01% |

Static Sorption of Forms I, III and V

Hygroscopicity testing was done on Forms I, III and V at various humidity conditions to understand sorption/desorption properties. Approximately 1 g of each form was ground with a mortar and pestle. Water content was determined by TGA. Approximately 100 mg of each powder was placed in static humidity chambers at 11 and 97% RH at approximately 25° C. for ~10 days. The only sample that exhibited a change in weight loss from Day 0 was the Form V sample stored at 97% RH. The data is summarized in Table 11 below:

TABLE 11

Hygroscopicity data of Forms I, III and V at 11% RH and 97% RH.

| Sample | % RH | Day 12 wt loss | Day 0 wt loss |
|---|---|---|---|
| Form I | 11 | 4.8% to 117.5° C. | 4.8% to 117° C. |
| Form III | 11 | 4.8% to 97.5° C. | 4.8% 97.3° C. |
| Form V | 11 | 2.2% to 109.8° C. | 2.2% to 97.8° C. |
| Form I | 97.6 | 4.7% to 119° C. | 4.8% to 117° C. |
| Form III | 97.6 | 4.8% to 100.2° C. | 4.8% 97.3° C. |
| Form V | 97.6 | 3.4% to 112.2° C. | 2.2% to 111° C. |

Example 8.—Analysis of the Effect of ST-246 API Particle Size on Dissolution Profiles of ST-246 Hard Gelatin Capsules The effect of the particle size of drugs on their dissolution profile has been extensively reviewed (see Fincher et al., 1968) and it had been hypothesized that a decrease in particle size of sparingly soluble drugs results in increased dissolution rates owing to the increased surface area of the drug exposed to the solvent.

Table 12 summarizes micronized and unmicronized ST-246 API particle size in microns, wherein micronization done for further testing the effect of particle size on the dissolution profiles of ST-246.

TABLE 12

Micronized and unmicronized ST-246 API particle size in microns.

| ST-246 API Lot# | Particle size of ST-246 API in microns | | |
|---|---|---|---|
| | D10 | D50 | D90 |
| Micronized | | | |
| SG-08G02-M | 1.008 | 3.243 | 8.097 |
| SG-08H05-M | 0.918 | 2.517 | 5.987 |
| SG-08H06-M | 1.007 | 2.602 | 5.627 |
| SG-08K07-M | 0.909 | 2.450 | 5.563 |
| SG-08L08-M | 1.032 | 2.479 | 4.999 |
| SG-08-09-M-Trial 1 | 1.233 | 2.166 | 4.617 |
| SG-08-09-M-Trial 2 | 1.587 | 4.802 | 13.601 |
| SG-08-09-M-Trial 3 | 1.723 | 5.846 | 17.698 |
| SG-08-09-M-Trial 4 | 1.888 | 7.111 | 22.806 |
| Un micronized | | | |
| SG-08-09-M unmicronized | 17.4 | 111.8 | 281.2 |

In order to evaluate the effect of particle of API on dissolution of ST-246 capsules, the following formulation comprising ST-246 polymorph Form I was evaluated. For these experiments, ST-246 (Form-I), 200 mg capsules were prepared using drug substance with different particle size distributions, such as d90% less than 10 μm, d90% 16 um, d90% 25 um, d90% less than 254 μm and d90% less than 75 μm. The composition of the ST-246 gelatin capsules are shown in the Table 13 below.

TABLE 13

Composition of capsules used for discriminating dissolution medium experiments.

| ST-246 Composition Ingredient | Lot# 0801637 mg/Capsule [d90% 5.3 μm] | SJI091023-API-Trial #3 mg/Capsule [d90% 16.6 μm] | SJI091023-API-Trial #4 mg/Capsule [d90% 26.6 μm] | SG-09K10-Q-API-40 um mg/Capsule Particle size distribution d90% 40.85 μm] | SG-09K10-Q-API-60 um mg/Capsule d90% 58.20 μm] | Lot# WW386-89 mg/Capsule [d90% 75 m] | Lot# DN401-93 mg/Capsule [d90% 254 μm] |
|---|---|---|---|---|---|---|---|
| ST-246 (Form-I) Monohydrate | 200 | 200 | 200 | 200 | 200 | 200 | 200 |
| Microcrystalline cellulose, NF | 88.60 | 88.60 | 88.60 | 88.60 | 88.60 | 88.60 | 88.60 |
| Lactose monohydrate, NF | 33.15 | 33.15 | 33.15 | 33.15 | 33.15 | 33.15 | 33.15 |
| Croscarmellose sodium, NF | 42.90 | 42.90 | 42.90 | 42.90 | 42.90 | 42.90 | 42.90 |
| Colloidal silicon dioxide, NF | 1.95 | 1.95 | 1.95 | 1.95 | 1.95 | 1.95 | 1.95 |
| Hydroxypropyl methylcellulose, USP | 13.65 | 13.65 | 13.65 | 13.65 | 13.65 | 13.65 | 13.65 |
| Sodium lauryl sulfate, NF | 7.80 | 7.80 | 7.80 | 7.80 | 7.80 | 7.80 | 7.80 |
| Magnesium stearate NF | 1.95 | 1.95 | 1.95 | 1.95 | 1.95 | 1.95 | 1.95 |
| Capsule weight | 390 | 390 | 390 | 390 | 390 | 390 | 390 |

For these experiments, ST-246 (Form I) dissolution profiles are determined in an USP apparatus 2 (paddle) which runs at 75 rpm. The dissolution profiles are determined at 37° C., in a 900 ml dissolution medium, containing 0.05 M Phosphate buffer pH 7.5, containing 3% HDTMA. Cumulative drug release over time is represented as a percent of ST-246% dissolved and is plotted as a function of dissolution medium sampling time.

As summarized in Table 14 and FIG. 16-20, ST-246 (Form I) with a D90 particle size (d90%) of 5.3 microns and 16.6 microns achieved almost 100% dissolution at approximately 22 minutes, whereas ST-246 (Form I) with a D90 particle size (d90%) of 26.6 achieved almost 100% dissolution at 30 minutes. Also, ST-246 (Form I) with a D90 particle size of 40.85 and 58.2 microns achieves almost 85 to 86% dissolution in 30 minutes. Further, ST-246 (Form I) with a D90 particle size of 75 microns achieves almost 86% dissolution in 30 minutes and ST-246 (Form I) with D90 particle size of 254 microns achieves only 44% dissolution in 60 minutes. Table 14 shows dissolution profiles using an alternate dissolution method (1% HDTMA in 900 mL of 0.05 M Phosphate buffer pH 7.5 at 37° C. in an USP apparatus 2 (paddle) which runs at 50 rpm) for the capsules made with ST-246 (Form I) with a D90 particle size (d90%) of 5.3 microns, 16.6 microns, and 26.6 microns.

TABLE 14

The % Dissolution of ST-246 (Form I) Capsules with API of Various Particle Sizes in 3% HDTMA in 900 ml of 0.05M Phosphate buffer, pH 7.5, using dissolution apparatus USP 2 with a paddle speed of 75 RPM at 37° C.

| | % Dissolution | | | | | | |
|---|---|---|---|---|---|---|---|
| Time in Minutes | Lot# 0801637 d90% 5.3 μm | SJI091023-API-Trial #3 d90% 16.6 μm | SJI091023-API-Trial #4 d90% 26.6 μm | SG-09K10-Q-API-40 um d90% 40.85 μm | SG-09K10-Q-API-60 um d90% 58.20 μm | Lot# WW386-89 d90% 75 μm | Lot# DN401-93 d90% 254 μm |
| 15 | 88 | 85 | 76 | 70 | 67 | 69 | 22 |
| 30 | 98 | 96 | 91 | 82 | 80 | 81 | 31 |
| 45 | 99 | 98 | 95 | 86 | 85 | 87 | 39 |
| 60 | 101 | 99 | 97 | 89 | 88 | 94 | 44 |

| | % RSD | | | | | | |
|---|---|---|---|---|---|---|---|
| Time in Minutes | Lot# 0801637 d90% 5.3 μm | SJI091023-API-Trial #3 d90% 16.6 μm | SJI091023-API-Trial #4 d90% 26.6 μm | SG-09K10-Q-API-40 um d90% 40.85 μm | SG-09K10-Q-API-60 um d90% 58.20 μm | Lot# WW386-89 d90% 75 μm | Lot# DN401-93 d90% 254 μm |
| 15 | 5 | 5 | 13 | 2.8 | 4.8 | 3 | 2 |
| 30 | 4 | 1 | 4 | 2.6 | 3.9 | 5 | 3 |
| 45 | 3 | 1 | 3 | 2.5 | 2.8 | 4 | 3 |
| 60 | 2 | 2 | 2 | 2.5 | 3.2 | 3 | 3 |

TABLE 15

The % Dissolution of ST-246 (Form I) Capsules with API of Various Particle Sizes in 1% HDTMA in 900 ml of 0.05M Phosphate buffer, pH 7.5, using dissolution apparatus USP 2 with a paddle speed of 50 RPM at 37° C.

| | % Dissolution | | | % RSD | | |
|---|---|---|---|---|---|---|
| Time in Minutes | Lot# 0801637 d90% 5.3 μm | SJI091023-API-Trial #3 d90% 16.6 μm | SJI091023-API-Trial #4 d90% 26.6 μm | Lot# 0801637 d90% 5.3 μm | SJI091023-API-Trial #3 d90% 16.6 μm | SJI091023-API-Trial #4 d90% 26.6 μm |
| 15 | 44 | 55 | 56 | 22 | 12 | 11 |
| 30 | 75 | 70 | 71 | 11 | 9 | 7 |
| 45 | 87 | 77 | 77 | 3 | 8 | 7 |
| 60 | 94 | 81 | 81 | 3 | 8 | 7 |

Further, ST-246, Form I, can be formulated for oral administration in capsules comprising 200 mg of ST-246. For these experiments, ST-246 (Form I) with a D90 particle size of between about 5.3 to 75 microns may be used. All inactive ingredients may be GRAS and USPLNF excipients. The manufacturing process may include wet granulation using a high shear mixer/granulator and filling into hard gelatin capsules.

Suitable dosage forms can include capsules containing various amounts of active ingredient. The quantitative composition of exemplary dosage form containing 200 mg of ST-246 monohydrate, micronized with a D90 particle size of less than about 10 microns, is summarized in Table 15 below:

TABLE 16

Quantitative Composition of ST-246 Drug Product

| | | 200 mg Strength | |
|---|---|---|---|
| Ingredient | Function | mg/Capsule | % w/w |
| ST-246 monohydrate[a] (micronized, $D_{90}$ <10 microns) monohydrate, based on anhydrous basis. | Active Ingredient; white to off-white powder | 200.00 | 51.28 |
| Microcrystalline cellulose, NF[b] | Water Insoluble Diluent | 88.60 | 22.72 |
| Lactose monohydrate, NF | Water soluble Diluent | 33.15 | 8.50 |
| Croscarmellose sodium, NF[b] | Disintegrant | 42.90 | 11.00 |
| Colloidal silicon dioxide, NF | Glidant | 1.95 | 0.50 |
| Hypromellose, USP | Binder | 13.65 | 3.50 |
| Sodium lauryl sulfate, NF | Wetting Agent/Solubilizer | 7.80 | 2.00 |
| Magnesium stearate NF | Lubricant | 1.95 | 0.50 |
| Water USP[c] | Granulating Agent | | |
| Hard Gelatin Capsule shell, orange/black, Size 0 | Encapsulation | 1 capsule | — |
| Capsule weight, mgs | | 390 | 100 |

[a]The quantity of ST-246 monohydrate may be adjusted based on the drug substance assay, which is calculated to reflect the purity and water content. The amount of Lactose will be adjusted to maintain the same capsule weight.
[b]Microcrystalline cellulose and croscarmellose sodium are added as intra granular and extra granular excipients.
[c]Removed during processing.

Other examples of compositions are summarized in Table 17.

TABLE 17

Quantitative Composition of ST-246 Drug Product

| Ingredient | Function | 200 mg Strength mg/Capsule |
|---|---|---|
| ST-246 monohydrate[a] (micronized, $D_{90}$ <10 microns) monohydrate, based on anhydrous basis. | Active Ingredient; white to off-white powder | 200.00 |
| Microcrystalline cellulose, NF[b] | Water Insoluble Diluent | 88.60 |
| Lactose monohydrate, NF | Water soluble Diluent | 40.95 |
| Croscarmellose sodium, NF[b] | Disintegrant | 42.90 |
| Colloidal silicon dioxide, NF | Glidant | 1.95 |
| Hypromellose, USP | Binder | 13.65 |
| Magnesium stearate NF | Lubricant | 1.95 |
| Water USP[c] | Granulating Agent | |
| Hard Gelatin Capsule shell, orange/black, Size 0 | Encapsulation | 1 capsule |
| Capsule weight, mgs | | 390 |

Example 9—Inhibition of Orthopox Viral Replication

The ability of the Form I of ST-246 to inhibit Vaccinia virus is established by the following experimental procedure:

Preparation of Virus Stock

Virus stocks of Vaccinia virus (NYCBH) are prepared in Vero cells infected at low multiplicity (0.01 plaque forming units (PFU)/cell) and harvested when cytopathic effects were complete (4+CPE). The samples are frozen and thawed and then sonicated to release cell-associated virus. The cell debris are removed by low-speed centrifugation, and the resulting virus suspension is stored in 1 mL aliquots at −80.degree. C. The PFU/mL of the virus suspension is quantified by standard plaque assay on Vero and BSC-40 cells.

Vaccinia CPE Assay

To determine the amount of vaccinia virus stock required to produce complete CPE in 3 days, Vero cell monolayers are seeded on to 96-well plates and infected with 2-fold serial dilutions of the vaccinia virus stock. At 3 days post-infection, the cultures are fixed with 5% glutaraldehyde and stained with 0.1% crystal violet. Virus-induced CPE is quantified spectrophotometrically at OD.sub.570. From this analysis, a 1:800 dilution of vaccinia virus stock is chosen for use in the HTS assay. This amount of vaccinia virus represents a multiplicity of infection of approximately 0.1 PFU/cell.

To establish the signal-to-noise ratio (S/N) of the 96-well assay and evaluate the well-to-well and assay-to-assay variability, six independent experiments are performed. Vero cell monolayers are infected with 1:800 dilution of vaccinia virus stock.

Each plate contains the following controls: quadruplicate virus-infected wells, quadruplicate uninfected cell wells and a dose response curve in duplicate for cidofovir (CDV) added at 300, 100, 30 and 10 DAM, or phosphonoacetic acid (PAA) added at 2100, 714, 210, and 71 M as reference standards. At day 3 post-infection, the plates are processed as described above. The results of these experiments indicate that the 96-well assay format is robust and reproducible.

Form I Testing

ST-246, Form I is tested in the vaccinia virus CPE assay. Form I is dissolved in DMSO and diluted in medium such that the final concentration in each well is 5 pM compound and 0.5% DMSO. Form I is added robotically to the culture medium using the Biomek® FX robot system.

Following compound addition, the cultures are infected with vaccinia virus. After 3 days, plates are processed and CPE quantified as described. ST-246 Form I of the invention inhibited vaccinia virus-induced CPE by greater than 50% at the test concentration (5 .mu.M). Form I is further evaluated for potency ($EC_{50}$) in the CPE assay and cytotoxicity (CC.sub.50) in an MTT assay. The MTT assay measures mitochondrial dehydrogenase activity in dividing cells. The absorbance of the formazin at 490 nm can be measured directly from 96-well assay plates following solubilization of the formazin in 50% ethanol. The quantity of formazin product is directly proportional to the number of living cells in culture. The $EC_{50}$ values are determined by comparing compound-treated and compound-untreated cells using a computer program. Thus, the $EC_{50}$ value of ST-246 Form I in the CPE assay is 50 nM.

The specificity of ST-246, Form I, for orthopox virus inhibition is reflected in the fact that they do not inhibit the replication of unrelated viruses, including Pichinde virus, Rift Valley fever virus (strain MP12), respiratory syncytial virus and cytomegalovirus.

Example 10—ST-246, Form I In Vivo Studies

Study Design

The study is designed as a randomized, placebo-controlled, parallel-group, longitudinal study of oral ST-246, Form I, in cynomolgus monkeys (Macaca fascicularis). For these experiments, 15 NHPs are infected with $5\times10^7$ PFU of the Zaire 79 strain of MPX by i.v. injection and are randomized into five treatment arms of three NHP each. The vehicle or ST-246, Form I, are administered at 3 mg/kg, 10 mg/kg, 30 mg/kg, and 100 mg/kg orally once per day followed by 5 ml/kg of a 30% suspension of hydrated homogenized monkey biscuits.

Treatment starts on day 3 post-infection and has continued once daily for 14 days. The infected animals are observed at least twice each day for up to 33 days to examine them for signs of illness. Blood samples are collected from the infected animals for virological, hematological, immunological, and chemical analyses. A full necropsy is performed on animals that died during the study to collect tissues for pathological examination. To determine the extent of infection, three animals are euthanized on day 3 and their tissues are processed to determine the virus levels in tissues. The organs are freeze-thawed, and a 10% tissue homogenate is produced and analyzed by quantitative PCR. The number of MPX genomes per milliliter of blood is determined by the extraction of DNA with a Qiagen QIAmp DNA minikit and quantitative TaqMan-MGB PCR, as described previously. Monkeypox lesions are enumerated daily.

Pharmacokinetic Analysis of ST-246, Form I, in Cynomolgus Monkeys (NHP).

The NHP are administered ST-246 at 10, 20, and 30 mg/kg by oral gavage under fed conditions. On the dosing days, all animals are administered a primate biscuit slurry immediately prior to dose administration. The biscuit slurry contained one can (8 oz) of Ensure or other liquid diet, approximately 36 g of fluid and electrolyte replacement formula (Prang), approximately 94 g of infant formula, 1 jar (2.5 oz) of strained fruit, five monkey chow biscuits, and approximately 2 oz of water blended together to achieve a uniform consistency. The biscuit slurry is administered via oral gavage at a dose volume of 10 ml/kg. After each dose of the test article is administered and prior to the removal of the gavage tube, the tube is flushed with 10 ml of tap water. The dosing formulations are stirred with a magnetic stir bar and stir plate prior to and throughout the administration. Individual doses are based on the most recent body weights. With the exception of the 20-mg/kg dose group, each dose group contains three male and three female NHP; the 20-mg/kg dose group contained four male and four female NHP. The NHP in the 10- and 30-mg/kg dose groups received ST-246, Form I, for 14 consecutive days, and those in the 20-mg/kg dose group received a single dose of ST-246. Blood samples are collected from the femoral artery/vein pretesting (0 h) (prior to dosing) and at 0.5, 1, 2, 3, 4, 6, 8, 12, and 24 h postdosing on days 1, 7, and 14 for determination of the plasma concentrations of ST-246, Form I.

Evaluation of ST-246, Form I, Efficacy in Cynomolgus Monkey Model of Monkeypox.

The study described here is randomized, placebo-controlled, parallel-group, longitudinal study of oral ST-246, Form I, in NHP infected i.v. with MPX. The animals exhibit extensive MPX infection of major tissues, as demonstrated by the level of virus in tissues' At the time of ST-246, Form I, treatment, one-third of the NHP has viral lesions. All animals receiving vehicle alone either die or require euthanasia because they are moribund during the study period of 33 days, while all animals receiving ST-246, Form I, survive. Each of the animals receiving ST-246, Form I, survive the full study.

For these experiments, viral load and lesion development are quantified daily. All doses of ST-246, Form I, significantly decrease the amount of viral DNA present compared to that in the vehicle-treated animals beginning on 5 dpi. At the end of the 14-day treatment, the viral loads in the ST-246, Form I,—treated groups show a linear dose-response, with all treatment groups showing a significant reduction in the level of virus replication of more than 1,000-fold compared to that in the vehicle-treated group.

Example 11—Pharmacokinetic Comparison of a Single Oral Dose of Form I Versus Form V Capsules of the Anti-Orthopoxvirus Compound ST-246 in Healthy Human Volunteers Study Design This was a Phase I, randomized, double-blind, crossover, exploratory study to compare the pharmacokinetics (PK; AUC variables and $C_{max}$) of a single 400 mg (2×200 mg) oral dose of ST-246 Form I (the test) with ST-246 Form V (the reference), and to evaluate the safety and tolerability of both Forms in fed normal healthy volunteers. Twelve of sixty-three screened individuals (males and non-pregnant females, 18 to 50 years old inclusive) were accepted into the study, and were randomized to one of the following sequences: Form I then Form V, or Form V then Form I.

To determine the PK of ST-246, a urine and baseline (0 hour) venous blood sample were obtained on Day 1, followed by serial blood draws after medication administration. All subjects received a single, 400-mg dose (2×200 mg) of either Form I or Form V of ST-246, orally administered within 30 minutes after a standard light meal. Post-dose (Treatment 1) blood samples for PK analyses were taken at 0.5, 1, 2, 3, 4, 8, 12, 24, 36, 48, and 72 hours. A post-dose urine sample was obtained on Day 2. A Washout Period occurred during study Days 2-10, so Treatment 2 occurred on Day 11. At this time, those subjects originally receiving Form I of ST-246, now received a single, 400 mg dose (2×200 mg) of Form V, and vice versa. Blood sampling for PK analyses following Treatment, 2, occurred as for post-Treatment 1, and urine sampling occurred on Day 14. Plasma samples were collected and stored at −70° C. until analyzed for maximum drug concentration [Cmax], time to maximum drug concentration [Tmax], terminal half-life [t½], area under the concentration-time curve [AUC], and renal clearance [Clr]. Urine samples were immediately centrifuged at 4° C. for 10 min at 2,000×g, and evaluated for urinary excretion. ST-246 was quantified from human plasma specimens by a validated liquid chromatography and tandem mass spectrometry method using an analog of ST-246 as an internal standard.

The study compared the pharmacokinetic (PK) profiles of ST-246 Form 1 and Form V capsules following a single oral dose administration. This objective was achieved through the collection and analysis of plasma samples for PK assessment of Form I from 12 of 12 subjects and of Form V from 11 of 12 subjects. Pharmacokinetic parameters, peak plasma concentration (Cmax), time at which Cmax is attained post dose administration (Tmax), plasma exposure (AUC0-τ, AUC0-∞) and elimination half-life (t½) were estimated for ST-246 by applying non-compartmental analysis using WinNonlin professional edition software (Pharsight Corporation, Version 5.2).

The pharmacokinetic parameters for ST-246, Form I and Form V, are summarized in Table 18 below:

TABLE 18

Pharmacokinetic parameters for ST-246, Form I and Form V.

| Form Group | Statistics | $AUC_{0-\tau}$ (hr*ng/mL) | $AUC_{0-\infty}$ (hr*ng/mL) | $AUC_{(extrap)}$ (%) | $t_{1/2}$ (hr) | $C_{max}$ (ng/mL) | $T_{max}$ (hr) |
|---|---|---|---|---|---|---|---|
| Form I | N | 12 | 11 | 11 | 11 | 12 | 12 |
| | Mean | 15624.5 | 19922.02 | 17.444 | 27.446 | 1068.9 | 3.8 |
| | SD | 5449.188 | 6543.563 | 7.84 | 13.109 | 294.3 | 1.5 |
| | CV % | 34.876 | 32.846 | 44.947 | 47.763 | 27.5 | 39.6 |
| | Geometric Mean | 14816.26 | 19049.63 | 15.748 | 24.746 | 1026.9 | 3.5 |
| | Median | 14151.15 | 17201.75 | 13.214 | 25.12 | 1170 | 3.5 |
| | Minimum | 8053.5 | 13959.18 | 5.7 | 10.94 | 525 | 2 |
| | Maximum | 26596.58 | 31058.8 | 30.4 | 56.48 | 1590 | 8 |
| | Missing | 0 | 1 | 1 | 1 | 0 | 0 |
| Form V | N | 11 | 8 | 8 | 8 | 11 | 11 |
| | Mean | 20065.32 | 21982.71 | 15.275 | 29.18 | 1230.2 | 3.8 |
| | SD | 6744.974 | 9330.953 | 10.811 | 21.992 | 348.6 | 1.6 |
| | CV % | 33.615 | 42.447 | 70.78 | 75.365 | 28.3 | 41.9 |
| | Geometric Mean | 19020.83 | 20409.17 | 12.369 | 23.083 | 1185 | 3.6 |
| | Median | 19398.5 | 19465.47 | 12.465 | 16.647 | 1180 | 4 |
| | Minimum | 10398.53 | 11946.95 | 4.53 | 11.48 | 732 | 2 |

TABLE 18-continued Pharmacokinetic parameters for ST-246, Form I and Form V.

| Form Group | Statistics | $AUC_{0-\tau}$ (hr*ng/mL) | $AUC_{0-\infty}$ (hr*ng/mL) | $AUC_{(extrap)}$ (%) | $t_{1/2}$ (hr) | $C_{max}$ (ng/mL) | $T_{max}$ (hr) |
|---|---|---|---|---|---|---|---|
| | Maximum | 30974 | 39058.28 | 37.51 | 69.45 | 1940 | 8 |
| | Missing | 0 | 3 | 3 | 3 | 0 | 0 |

Figure 24:
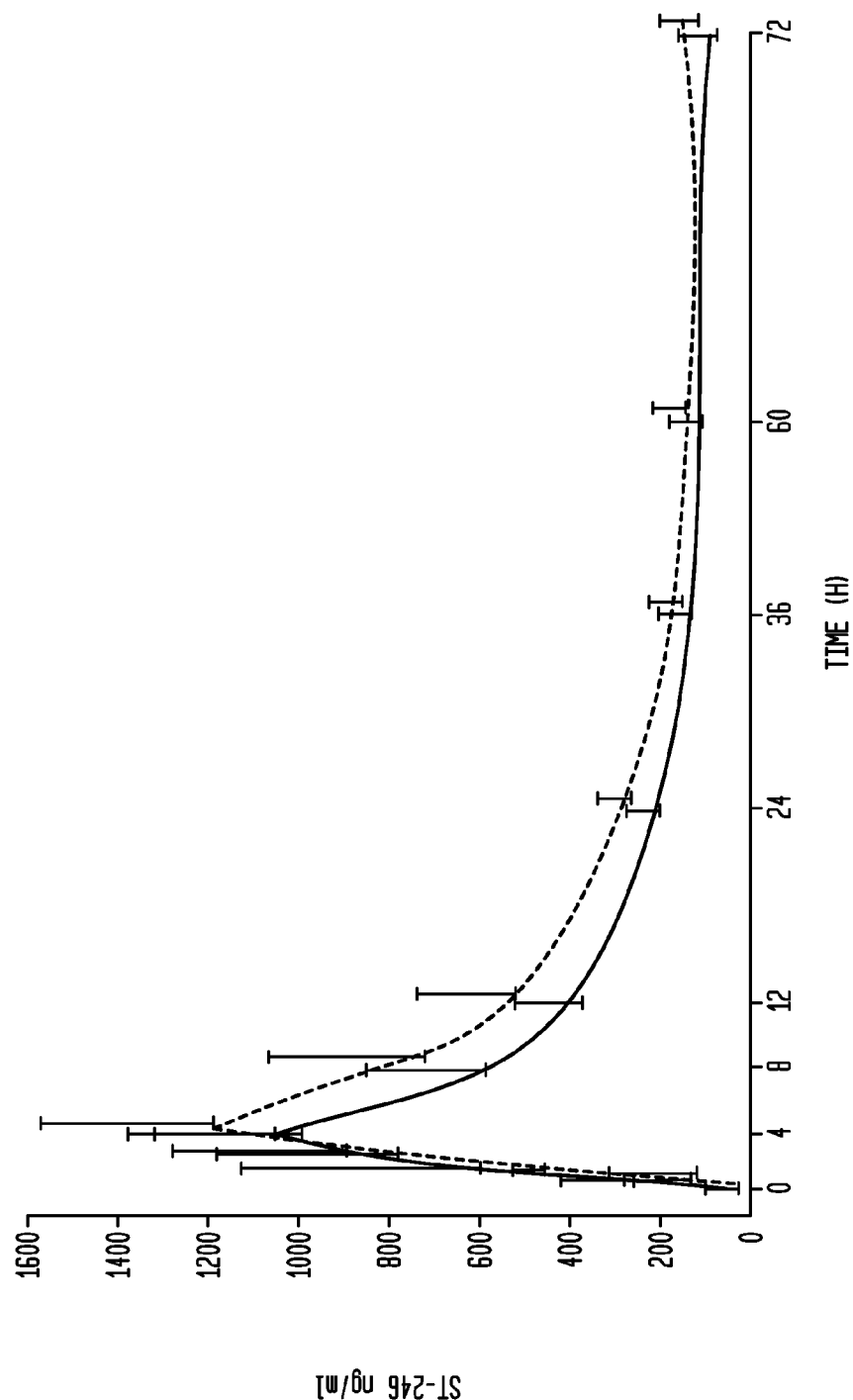
FIG. 24 depicts the mean (SD) ST-246 plasma concentrations over time (PK population) after a single oral administration.

NOTE:
For a given variable and drug form, geometric mean was not calculated if any of the values were 0
KEY:
$AUC_{0-\infty}$ = Area under the plasma concentration-time curve from time zero to infinity;
$AUC_{0-\tau}$ = Area under the drug concentration-time curve from time zero to time t where t is the last time-point with a drug concentration ≥ lowest obtainable quantification;
$AUC_{(extrap)}$ = Area under the curve extrapolated;
$t_{1/2}$ = Terminal half-life;
$C_{max}$ = maximum plasma concentration;
CV % = Coefficient of variance;
h = hours;
N = Number of subjects;
PK = Pharmacokinetics;
SD = Standard deviation;
$T_{max}$ = Time to maximum plasma concentration The mean (SD) ST-246 plasma concentrations over time (PK population) are shown in FIG. 24 after a single oral administration.

What is claimed is:

1. A method of treating Orthopoxvirus infections comprising administering to a subject in need thereof a therapeutically effective amount of a polymorph Form I of 4-trifluoromethyl-N-(3,3a,4,4a,5,5a,6,6a-octahydro-1,3-dioxo-4,6-ethenocycloprop[f]isoindol-2(1H)-benzamide (ST-246) which shows an X-ray powder diffraction pattern having characteristic peaks at a reflection angle 2θ of about 7.63, 10.04, 11.47, 14.73, 15.21, 15.47, 16.06, 16.67, 16.98, 18.93, 19.96, 20.52, 20.79, 22.80, 25.16, 26.53, 27.20, 27.60, 29.60, 30.23, 30.49, 30.68, 31.14, 33.65, 34.33, 35.29, 35.56, 36.30, 37.36, 38.42, 38.66 degrees.

2. The method of claim 1, wherein the polymorph Form I is at least about 70% free of other forms.

3. The method of claim 1, wherein the polymorph Form I is at least about 80% free of other forms.

4. The method of claim 1, wherein the polymorph Form I is at least about 90% free of other forms.

5. The method of claim 1, wherein the polymorph Form I is at least about 95% free of other forms.

6. The method of claim 1, wherein the polymorph Form I is at least about 99% free of other forms.

7. The method of claim 1, wherein the polymorph Form I is administered orally.

8. A method of treating eczema vaccinatum comprising administering to a patient in need thereof a therapeutically effective amount of a polymorph Form I of 4-trifluoromethyl-N-(3,3a,4,4a,5,5a,6,6a-octahydro-1,3-dioxo-4,6-ethenocycloprop[f]isoindol-2(1H)-benzamide (ST-246) which shows an X-ray powder diffraction pattern having characteristic peaks at a reflection angle 2θ of about 7.63, 10.04, 11.47, 14.73, 15.21, 15.47, 16.06, 16.67, 16.98, 18.93, 19.96, 20.52, 20.79, 22.80, 25.16, 26.53, 27.20, 27.60, 29.60, 30.23, 30.49, 30.68, 31.14, 33.65, 34.33, 35.29, 35.56, 36.30, 37.36, 38.42, 38.66 degrees.

* * * * *